(12) United States Patent
Kim et al.

(10) Patent No.: US 11,969,463 B2
(45) Date of Patent: Apr. 30, 2024

(54) METHOD FOR ACTIVATING T CELLS FOR CANCER TREATMENT

(71) Applicant: GOOD T CELLS, INC., Seoul (KR)

(72) Inventors: Jung Ho Kim, Seoul (KR); Beom Seok Kim, Seoul (KR)

(73) Assignee: GOOD T CELLS, INC., Seoul (KR)

( * ) Notice: Subject to any disclaimer, the term of this patent is extended or adjusted under 35 U.S.C. 154(b) by 523 days.

(21) Appl. No.: 16/637,927

(22) PCT Filed: Aug. 10, 2018

(86) PCT No.: PCT/KR2018/009225
§ 371 (c)(1),
(2) Date: May 22, 2020

(87) PCT Pub. No.: WO2019/031939
PCT Pub. Date: Feb. 14, 2019

(65) Prior Publication Data
US 2020/0289630 A1    Sep. 17, 2020

(30) Foreign Application Priority Data

Aug. 10, 2017 (KR) ........................ 10-2017-0101800

(51) Int. Cl.
| | |
|---|---|
| C07K 14/435 | (2006.01) |
| A61K 35/17 | (2015.01) |
| A61K 38/16 | (2006.01) |
| A61K 38/17 | (2006.01) |
| A61K 39/00 | (2006.01) |
| C12N 5/0783 | (2010.01) |
| C12N 15/869 | (2006.01) |

(52) U.S. Cl.
CPC .......... *A61K 39/0011* (2013.01); *A61K 35/17* (2013.01); *A61K 38/162* (2013.01); *A61K 38/1774* (2013.01); *C12N 5/0636* (2013.01); *C12N 15/869* (2013.01); *C12N 2501/22* (2013.01); *C12N 2501/2302* (2013.01); *C12N 2501/2304* (2013.01); *C12N 2501/2307* (2013.01); *C12N 2501/2312* (2013.01); *C12N 2501/2315* (2013.01); *C12N 2501/2321* (2013.01); *C12N 2501/24* (2013.01); *C12N 2501/25* (2013.01); *C12N 2502/1107* (2013.01); *C12N 2502/1114* (2013.01); *C12N 2502/1121* (2013.01); *C12N 2502/1157* (2013.01)

(58) Field of Classification Search
None
See application file for complete search history.

(56) References Cited

U.S. PATENT DOCUMENTS

| 6,037,135 A | 3/2000 | Kubo et al. |
|---|---|---|
| 2010/0135994 A1 | 6/2010 | Banchereau et al. |
| 2018/0141998 A1* | 5/2018 | Nguyen ............... C07K 16/005 |
| 2018/0153975 A1* | 6/2018 | Fritsch ............... C07K 14/4748 |
| 2019/0189241 A1* | 6/2019 | Tadmor .......... A61K 39/001102 |

FOREIGN PATENT DOCUMENTS

| JP | 2005-530493 A | 10/2005 |
|---|---|---|
| JP | 2007-117023 A | 5/2007 |
| JP | 2013-502235 A | 1/2013 |
| WO | WO-2003/088995 A2 | 10/2003 |
| WO | WO-2012/123755 A1 | 9/2012 |
| WO | WO-2016/044530 A1 | 3/2016 |
| WO | WO-2016/172722 A1 | 10/2016 |
| WO | WO-2016/187508 A2 | 11/2016 |
| WO | WO-2016/203577 A1 | 12/2016 |

OTHER PUBLICATIONS

Brennick et al. Neoepitopes as cancer immunotherapy targets: key challenges and opportunities. Immunotherapy (2017) 9(4), 361-371. Published Online: Mar. 17, 2017.*
Kiessling et al., Identification of an HLA-A*0201-restricted T-cell epitope derived from the prostate cancer-associated protein prostein, Brit. J. Can., 90:1034-40 (2004).
Carr et al., "CD27 mediates interleukin-2-independent clonal expansion of the CD8+ T cell without effector differentiation", PNAS, 103(51): 19454-19459 (2006).
Extended European Search Report in European Application No. 18843560.6 dated Jul. 30, 2021.
Fu et al., "Critical role of EBNA1-specific CD4+ T cells in the control of mouse Burkitt lymphoma in vivo", The Journal of Clinical Investigation, 114(4): 542-550 (2004).
Gupta et al., "A platform for designing genome-based personalized immunotherapy or vaccine against cancer", PLoS One, 11(11): e0166372 (2016).
Tschochner et al., "Identifying patient-specific Epstein-barr nuclear antigen-1 genetic variation and potential autoreactive targets relevant to multiple sclerosis pathogenesis", PLOS One, 11(2): e0147567 (2016).
Office Action in Korean Application No. 10-2018-0093987 dated Jul. 3, 2020.

(Continued)

*Primary Examiner* — Nianxiang Zou
(74) *Attorney, Agent, or Firm* — MARSHALL, GERSTEIN & BORUN LLP

(57) ABSTRACT

The present invention relates to a cancer-specific tumor antigen neoepitope represented by any one of SEQ ID NOs: 1 to 214, an antigen-presenting cell loaded with the neoepitope, and a method for activating T cells for cancer treatment using the antigen-presenting cell. An antigen-presenting cell, that is, a dendritic cell, loaded with a cancer-specific tumor antigen epitope provided in the present invention enables rapid and effective induction of differentiation and proliferation of cancer antigen-specific T cells, preferably memory T cells, and the memory T cells thus activated can treat a cancerous or neoplastic condition or prevent recurrence, progression, or metastasis of cancer while avoiding the defense mechanism of cancer cells.

7 Claims, 4 Drawing Sheets

Specification includes a Sequence Listing.

(56) References Cited

OTHER PUBLICATIONS

Office Action in Korean Application No. 10-2020-0170517 dated Nov. 10, 2021.
Office Action in Japanese Application No. 2020-507103 dated Jun. 22, 2022.

* cited by examiner

[FIG. 1]
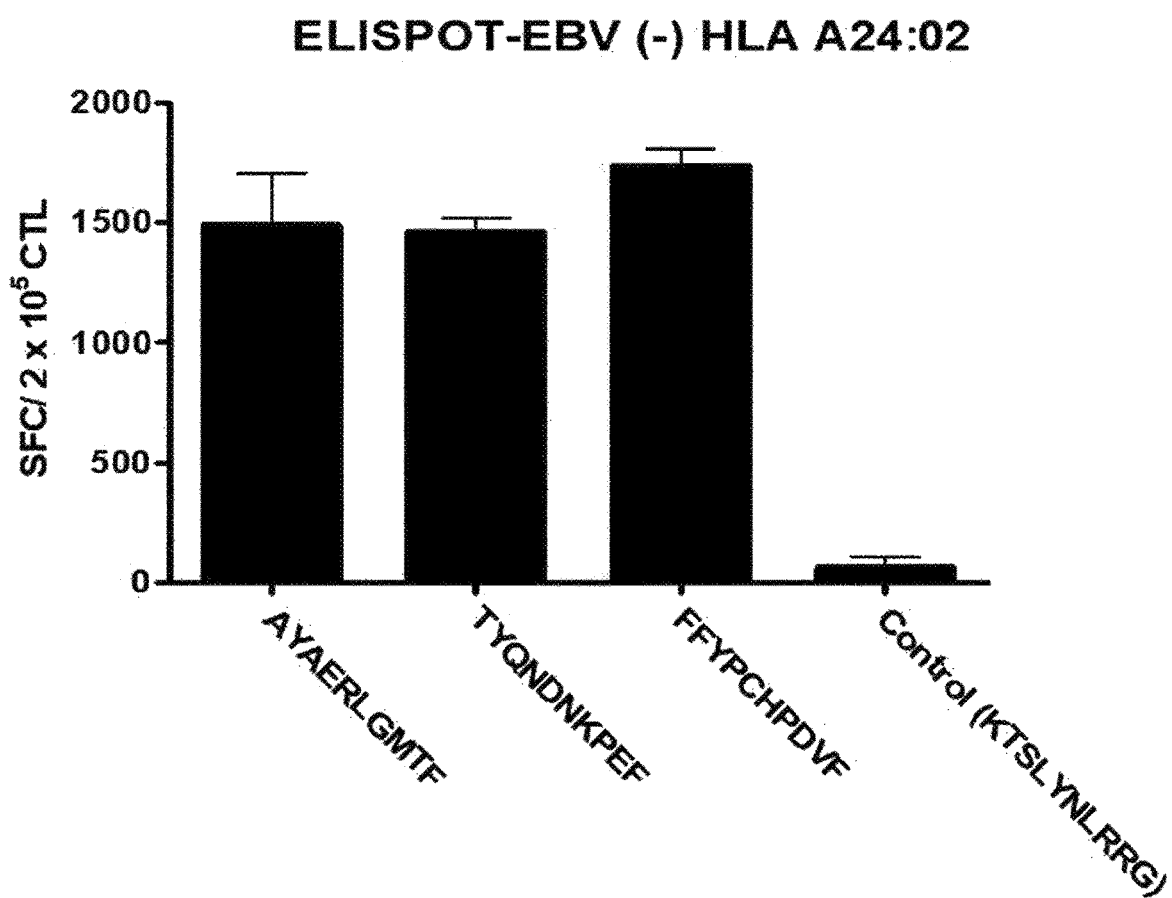

[FIG. 2]
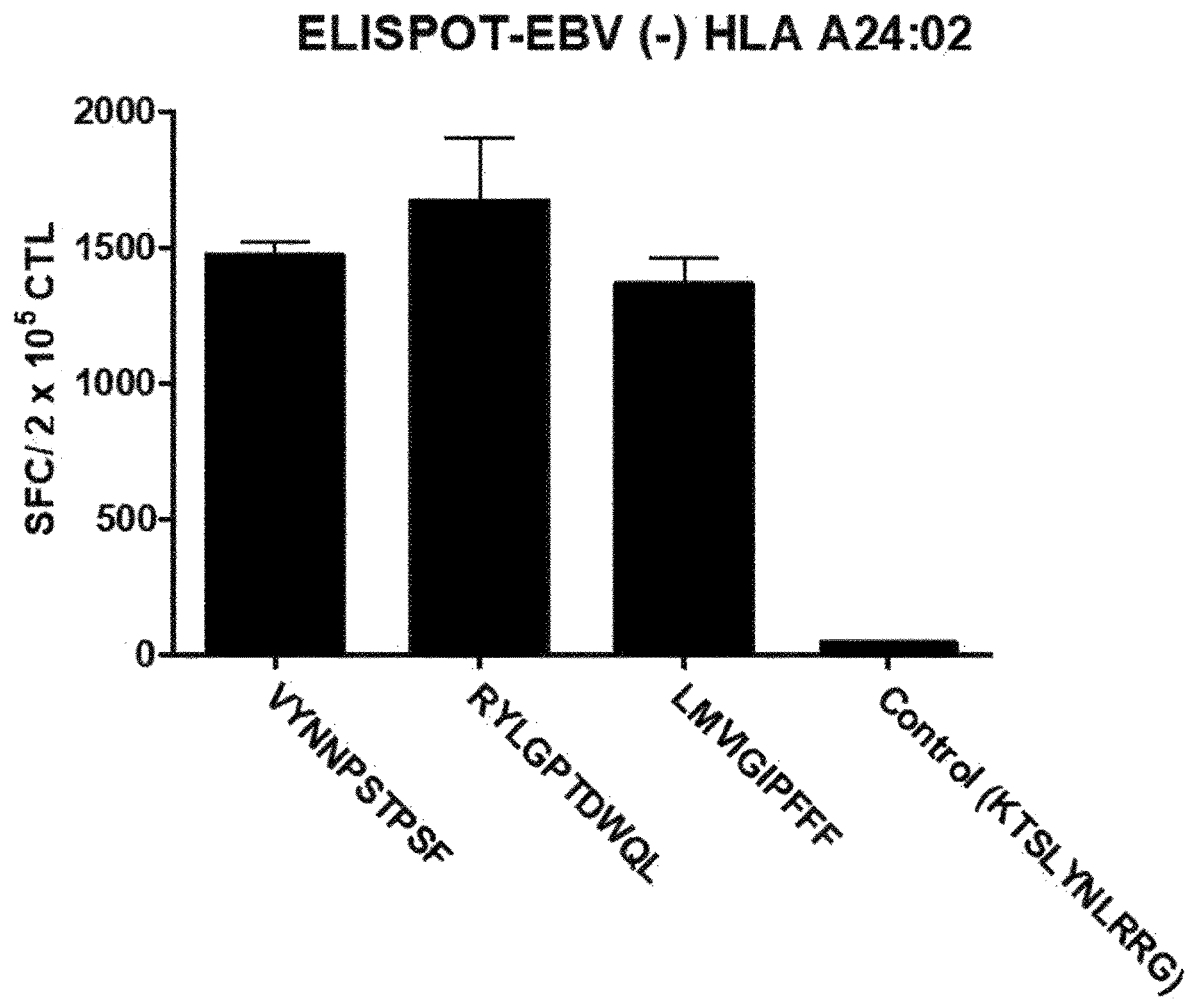

[FIG. 3]
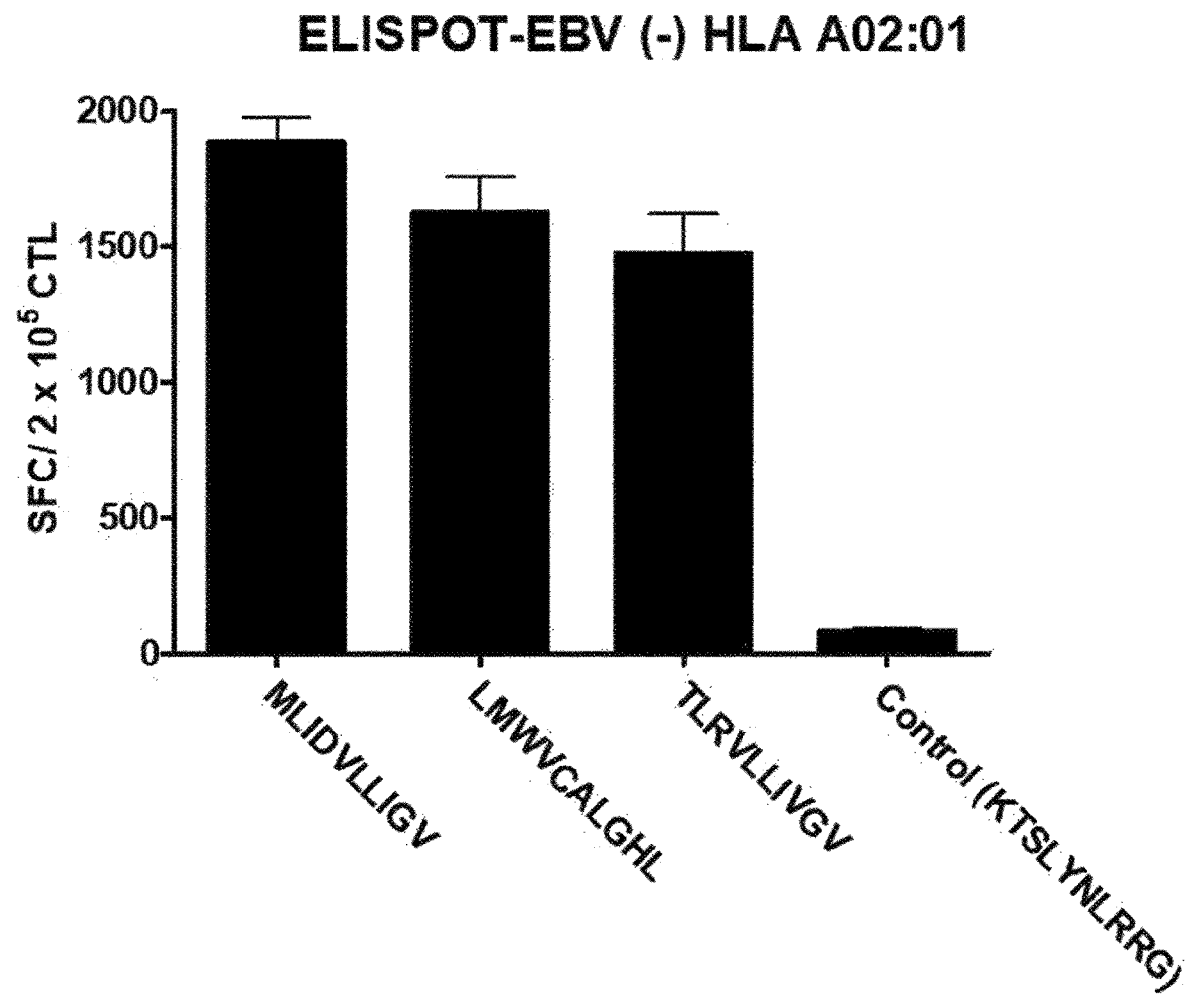

[FIG. 4]
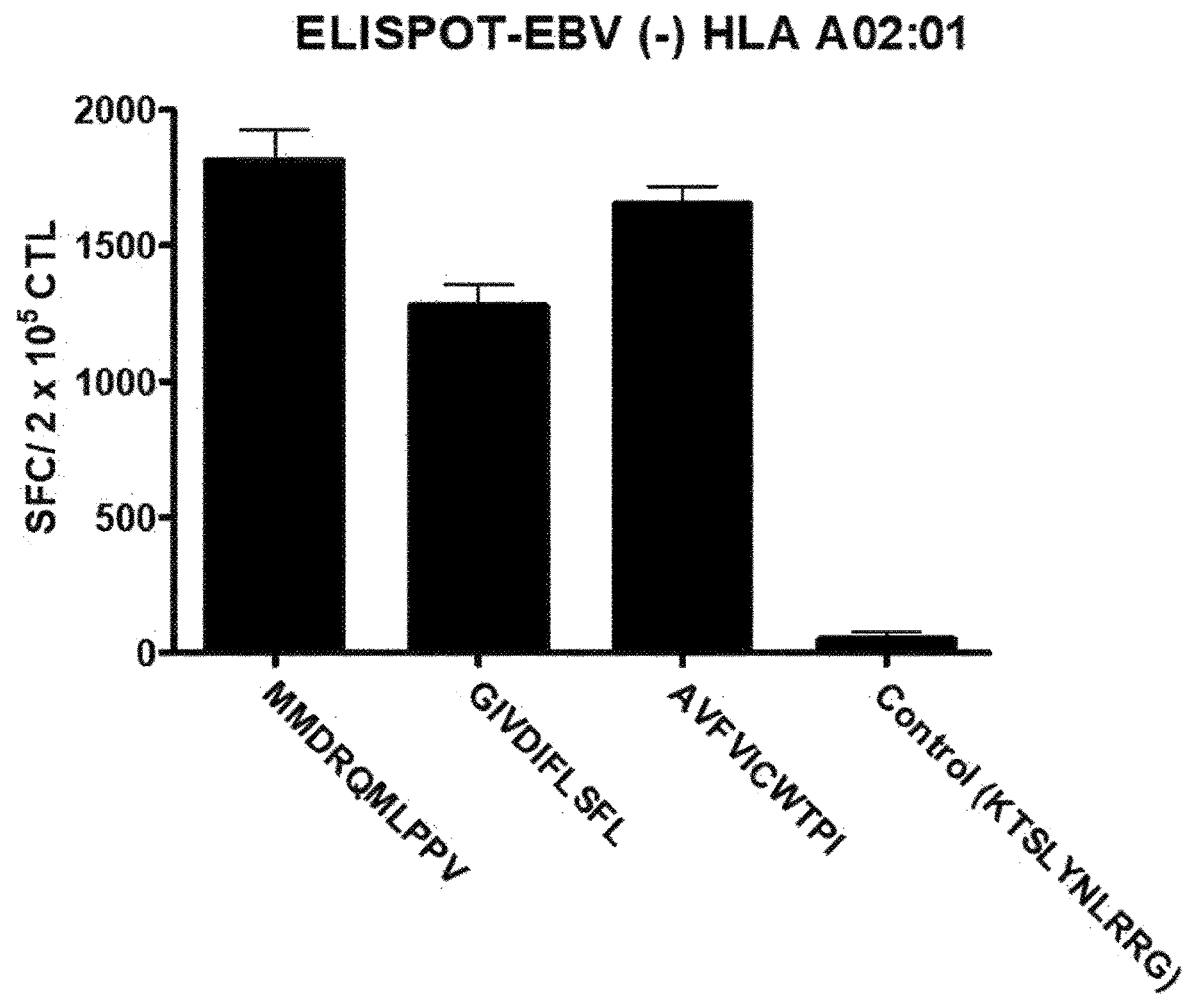

METHOD FOR ACTIVATING T CELLS FOR CANCER TREATMENT

CROSS REFERENCE TO RELATED APPLICATIONS

This application is a U.S. National Stage of International Application No. PCT/KR2018/009225, filed Aug. 10, 2018, which claims the benefit of priority from Korean Patent Application No. 10-2017-0101800, filed Aug. 10, 2017. The entire contents of these applications are incorporated herein by reference in their entirety.

INCORPORATION BY REFERENCE OF MATERIAL SUBMITTED ELECTRONICALLY

Incorporated by reference in its entirety is a computer-readable nucleotide/amino acid sequence listing submitted concurrently herewith and identified as follows: ASCII (text) file named " 55300_SubSeglisting.txt," 42,582 bytes, created on May 22, 2020.

TECHNICAL FIELD

The present invention relates to a cancer-specific tumor antigen neoepitope, an antigen-presenting cell loaded with the neoepitope, and a method for activating T cells for cancer treatment using the antigen-presenting cell.

BACKGROUND ART

Gastric cancer is known as a malignancy with a high incidence in the world, especially in Asia. There have been many known causes of development of gastric cancer; however, gastric cancer may be typically classified into EBV-associated gastric cancer, which is caused by infection with Epstein-Barr virus (EBV), and gastric cancer cell antigen-associated gastric cancer, which is caused by accumulation of genetic mutations in gastrointestinal cells. For current treatment for gastric cancer, excision of cancerous tissue has long been known to be the most effective, and chemotherapy and radiation therapy are also performed. However, it appears that gastric cancer is a hard-to-cure disease when not found early. In addition, although clinical trials have been conducted through several biological agents (antibodies, small molecules), therapeutic agents with good clinical effects have not yet been reported.

Recently, cancer cell-specific targeted therapy using patient-derived autologous T cells has been studied in several institutions, and clinical trials have been conducted for lymphoma using chimeric antigen receptor (CAR) T cells in several institutions. As a result, due to good clinical effects and low side effects, such therapy has attracted much attention as a new field of anticancer therapy.

Use of patient-derived T cells decreases induction of immune responses which is the biggest side effect of cell therapeutic agents, and removes restrictions on the donor's HLA type. Thus, such T cells have been known as therapeutic agents which are effective and have no side effects. To date, CD8+ T cells, CD4+ T cells, NK cells, dendritic cells, and CAR T cells are known as types of cell therapeutic agents which are most widely used in the field of anticancer therapy. NK cells have cell-killing efficacy, and have several side effects due to not having antigen specificity. Dendritic cells are therapeutic agents belonging to the vaccine concept in that they have no function of directly killing cells, and are capable of delivering antigen specificity to T cells in the patient's body so that cancer cell specificity is imparted to T cells with high efficiency. In addition, CD4+ T cells play a role in helping other cells through antigen specificity, and CD8+ T cells are known to have the best antigen specificity and cell-killing effect.

However, most cell therapeutic agents, which have been used or developed to date, have limitations and thus have no clinical effect. Taking a look at the limitations, cancer cells, on their own, secrete substances that suppress immune responses in the human body, or do not present antigens necessary for production of antibodies against such cancer cells, thereby preventing an appropriate immune response from occurring.

Meanwhile, dendritic cells not only act as surveillants to detect antigens that come from the outside of the human body or are produced internally, but also quickly travel to the secondary lymphoid organs with such recognized and absorbed antigen, thereby acting as specialized antigen-presenting cells that present the antigens to immune cells, including T cells, which react with the antigens. Anti-cancer immunotherapeutic vaccines using dendritic cells have been developed through several methods, and may be largely divided into ex vivo generated dendritic cell vaccines and in vivo dendritic cell vaccines. The in vivo dendritic cell vaccine works in a manner of directly delivering an antigen to dendritic cells present in the body. In addition, a method using the ex vivo generated dendritic cell vaccine is in such a manner that dendritic cells are isolated from the patient's PBMCs and an antigen to be presented is delivered to the isolated dendritic cells, through which the dendritic cells are activated and then injected back into the patient so that the antigen is delivered from the injected dendritic cells to T cells. In the latter, ex vivo dendritic cell culture method and antigen delivery method are important, and currently used antigen presentation methods include transfection of DNA of an antigen to be presented using virus or nucleofection, or antigen delivery targeting dendritic cells in which an antigen is bound to an antibody targeting the dendritic cells.

Currently, the biggest problems in dendritic cell vaccines are that severe chronic inflammatory phenomena in the body and the Warburg effect are exhibited, and it is considered very difficult to achieve effective activation of anticancer immune cells under the cancer microenvironment in which immunosuppressive cytokines, immunosuppressive T cells, dendritic cells, and the like are present.

TECHNICAL PROBLEM

An object of the present invention is to provide an Epstein-Barr virus (EBV)-negative cancer-specific tumor antigen neoepitope, and a composition for activating T cells which comprises the same.

Another object of the present invention is to provide an antigen-presenting cell loaded with a neoepitope of the present invention, the antigen-presenting cell being capable of activating T cells for cancer treatment.

Yet another object of the present invention is to provide a T cell, activated by the antigen-presenting cell loaded with a neoepitope of the present invention.

Still yet another object of the present invention is to provide a method for activating T cells for cancer treatment.

However, the technical problem to be solved by the present invention is not limited to the above-mentioned problems, and other problems which are not mentioned will be clearly understood by those skilled in the art from the following description.

SOLUTION TO PROBLEM

According to an embodiment of the present invention, there is provided a cancer-specific tumor antigen epitope.

In the present invention, the "cancer-specific tumor antigen epitope" is derived from a mutant protein antigen which is present only in cancer cells and is not present in normal cells. In the present invention, the cancer-specific tumor antigen epitope includes at least one epitope recognized by T cell receptors; and such an epitope may preferably include neoepitopes of autologous cancer antigens that appear due to mutation of cancer genes in Epstein-Barr virus (EBV)-negative cancer.

In the present invention, the "neoepitope" refers to an epitope that is not present in a reference such as normal, non-cancerous cells or germline cells and is found in cancer cells. This includes, in particular, a situation where a corresponding epitope is found in normal, non-cancer cells or germline cells, but one or more mutations in cancer cells cause the epitope to be changed to a neoepitope. Regarding neoepitopes, it may be considered that the neoepitopes express random mutations in tumor cells that produce unique and tumor-specific antigens. Therefore, viewed from a different perspective, the neoepitopes may be identified considering the type (for example, deletion, insertion, transversion, transition, translocation) and effect (for example, non-sense, mis sense, frame shift, and the like) of mutation, which may serve as a first content filter through which silent and other non-relevant mutations are eliminated. In addition, it should be appreciated that neoepitope sequences can be defined as sequence stretches with relatively short length (for example, 7- to 11-mer), in which such stretches will include change(s) in the amino acid sequence. Most typically, the changed amino acid will be at or near the central amino acid position. For example, a typical neoepitope may have a structure of A4-N-A4, or A3-N-A5, or A2-N-A7, or A5-N-A3, or A7-N-A2, where A is a proteinogenic amino acid and N is a changed amino acid (relative to wild type or relative to matched normal). For example, neoepitope sequences as contemplated herein include sequence stretches with relatively short length (for example, 5- to 30-mer, more typically 7- to 11-mer, or 12- to 25-mer), in which such stretches include change(s) in the amino acid sequence. Thus, it should be appreciated that a single amino acid change may be presented in numerous neoepitope sequences that include the changed amino acid, depending on the position of the changed amino acid. Advantageously, such sequence variability allows for multiple choices of neoepitopes, and thus increases the number of potentially useful targets that can then be selected on the basis of one or more desirable traits (for example, highest affinity to the patient's HLA-type, highest structural stability, and the like). Most typically, such a neoepitope will be calculated to have a length of between 2 to 50 amino acids, more typically between 5 to 30 amino acids, and most typically between 9 to 15 amino acids, with a changed amino acid preferably centrally located or otherwise situated in such a manner as to improve its binding to MHC. For example, in a case where the epitope is to be presented by MHC-I complex, a neoepitope will be typically about 8 to 11 amino acids in length, while the neoepitope presented via MHC-II complex will typically have about 13 to 17 amino acids in length. As will be readily appreciated, since the position of the changed amino acid in the neoepitope may be other than central, the actual peptide sequence and with that actual topology of the neoepitope may vary considerably.

In the present invention, the neoepitope may exhibit binding affinity with at least one of HLA-A, HLA-B, HLA-C, HLA-E, HLA-F, HLA-G, f32-microglobulin, HLA-DPA1, HLA-DPB1, HLA-DQA1, HLA-DQB1, HLA-DRA1, HLA-DRB1, HLA-DRB3, HLA-DRB4, HLA-DRB5, HLA-DM, HLA-DOA, and HLA-DOB loci so that T cells, preferably memory T cells, extracted from human blood can have efficacy. Among these, the neoepitope may include those exhibiting high binding affinity with at least one of the HLA types that are most expressed by Koreans, for example, HLA-A*2402, HLA-A*0201, HLA-A*3303, HLA-A*1101, HLA-A*0206, HLA-A*3101, HLA-B*5101, HLA-B*4403, HLA-B*5401, HLA-B*5801, and HLA-B*3501, and preferably with HLA-A*2402 or HLA-A*0201.

Preferably, in the present invention, the neoepitope has high binding affinity for HLA-A*2402 and may be a neoepitope represented by any one of SEQ ID NOs: 1 to 49; or has high binding affinity for HLA-A*0201 and may be a neoepitope represented by any one of SEQ ID NOs: 50 to 214.

Here, in the present invention, for a method of measuring neoepitope-HLA affinity, NetMHC 3.4 (URL: www.cbs.dtu.dk/services/NetMHC-3.4/) may be used to predict whether a neoepitope binds to a specific HLA allele. However, the present invention is not limited thereto.

In the present invention, the "HLA" or "human leukocyte antigen" refers to human gene that encodes a major histocompatibility complex (MHC) protein on the surface of cells that are responsible for regulation of the immune system. "HLA-I" or "HLA class I" refers to human MHC class I gene including HLA-A, HLA-B, HLA-C, HLA-E, HLA-F, HLA-G, and β2-microglobulin loci. "HLA-II" or "HLA class II" refers to human MHC class II gene including HLA-DPA1, HLA-DPB1, HLA-DQA1, HLA-DQB1, HLA-DRA1, HLA-DRB1, HLA-DRB3, HLA-DRB4, HLA-DRB5, HLA-DM, HLA-DOA, and HLA-DOB loci.

In the present invention, the cancer may be Epstein-Barr virus (EBV)-negative cancer, and may include, without limitation, any cancer species as long as it expresses a neoepitope represented by any one of SEQ ID NOs: 1 to 214 of the present invention. Thus, the type thereof is not particularly limited, and examples thereof may include colorectal cancer, pancreatic cancer, gastric cancer, liver cancer, breast cancer, cervical cancer, thyroid cancer, parathyroid cancer, lung cancer, non-small cell lung cancer, prostate cancer, gallbladder cancer, biliary tract cancer, non-Hodgkin lymphoma, Hodgkin lymphoma, blood cancer, bladder cancer, kidney cancer, ovarian cancer, melanoma, colon cancer, bone cancer, skin cancer, head cancer, uterine cancer, rectal cancer, brain tumor, perianal cancer, fallopian tube carcinoma, endometrial carcinoma, vaginal cancer, vulvar carcinoma, esophageal cancer, small intestine cancer, endocrine adenocarcinoma, adrenal cancer, soft tissue sarcoma, urethral cancer, penile cancer, ureteral cancer, renal cell carcinoma, renal pelvic carcinoma, central nervous system (CNS) tumor, primary CNS lymphoma, spinal cord tumor, brain stem glioma, or pituitary adenoma, with gastric cancer being preferred.

According to another embodiment of the present invention, there is provided a nucleic acid molecule, encoding a cancer-specific tumor antigen epitope provided in the present invention, preferably, a neoepitope of Epstein-Barr virus (EBV)-negative cancer antigen represented by any one of SEQ ID NOs: 1 to 214.

The nucleic acid molecule of the present invention includes any nucleic acid molecule obtained by converting an amino acid sequence of a polypeptide provided in the present invention into a polynucleotide sequence as known to those skilled in the art. Thus, various polynucleotide sequences may be prepared due to open reading frame (ORF), all of which are also included in the nucleic acid molecule of the present invention.

According to yet another embodiment of the present invention, there is provided an expression vector, into which the isolated nucleic acid molecule provided in the present invention is inserted.

In the present invention, the "vector" is a nucleic acid molecule which is capable of transporting another nucleic acid linked thereto. One type of vector is a "plasmid," which refers to circular double-stranded DNA into which an additional DNA segment can be ligated. Another type of vector is a phage vector. Yet another type of vector is a viral vector, where an additional DNA segment can be ligated into the viral genome. Certain vectors are capable of autonomous replication in a host cell into which they are introduced (for example, bacterial vectors having a bacterial origin of replication and episomal mammalian vectors). Other vectors (for example, non-episomal mammalian vectors) can be integrated into the genome of a host cell upon introduction into the host cell, and thus are replicated along with the host genome. In addition, certain vectors are capable of directing expression of genes to which they are operatively linked. Such vectors are referred to herein as "recombinant expression vectors" or simply "expression vectors." In general, expression vectors useful in recombinant DNA techniques are often in the form of plasmids. In the present specification, "plasmid" and "vector" may be used interchangeably as the plasmid is the most commonly used form among vectors.

Specific examples of the expression vector in the present invention may be selected from, but are not limited to, the group consisting of commercially widely used pCDNA vectors, F, R1, RP1, Col, pBR322, ToL, Ti vectors; cosmids; phages such as lambda, lambdoid, M13, Mu, p1 P22, Qµ, T-even, T2, T3, T7; plant viruses. Any expression vector known, to those skilled in the art, as expression vectors can be used in the present invention, and the expression vector is selected depending on the nature of the target host cell. Introduction of a vector into a host cell may be performed by calcium phosphate transfection, viral infection, DEAE-dextran-mediated transfection, lipofectamine transfection, or electroporation. However, the present invention is not limited thereto, and those skilled in the art may adopt and use an introduction method appropriate for the expression vector and the host cell which are used. The vector may preferably contain at least one selection marker. However, the present invention is not limited thereto, and selection can be made using the vector that contains no selection marker, depending on whether or not a product is produced. The selection marker is selected depending on the target host cell, which is done using methods already known to those skilled in the art, and thus the present invention has no limitation thereon.

In order to facilitate purification of the nucleic acid molecule of the present invention, a tag sequence may be inserted into and fused to an expression vector. The tag includes, but is not limited to, hexa-histidine tag, hemagglutinin tag, myc tag, or flag tag, and any tag known to those skilled in the art which facilitates purification can be used in the present invention.

According to still yet another embodiment of the present invention, there is provided a host cell, transfected with the expression vector provided in the present invention.

In the present invention, the "host cell" includes individual cells or cell cultures which may be or have been recipients of the vector(s) for incorporation of a polypeptide insert. The host cell includes progeny of a single host cell, and the progeny may not necessarily be completely identical (in morphology or in genomic DNA complement) to the original parent cell due to natural, accidental, or intentional mutation. The host cell includes cells transfected in vivo with the polynucleotide(s) herein.

In the present invention, the host cell may include cells of mammalian, plant, insect, fungal, or cellular origin, and may be, for example, bacterial cells such as *E. coli, Streptomyces, Salmonella typhimurium;* fungal cells such as yeast cells and *Pichia pastoris;* insect cells such as Drosophila and Spodoptera Sf9 cells; animal cells such as Chinese hamster ovary (CHO) cells, SP2/0 (mouse myeloma), human lymphoblastoid, COS, NSO (mouse myeloma), 293T, Bowes melanoma cells, HT-1080, baby hamster kidney (BHK) cells, human embryonic kidney (HEK) cells, or PERC.6 (human retinal cells); or plant cells. However, the host cell is not limited thereto, and any cell known to those skilled in the art which can be used as a host cell is available.

According to still yet another embodiment of the present invention, there is provided a composition for activating T cells, comprising a cancer-specific tumor antigen epitope provided in the present invention, a nucleic acid molecule encoding the same, an expression vector into which the nucleic acid molecule is inserted, or a host cell transformed with the expression vector.

As used herein, the term "activation of T cells" refers to a population of monoclonal (for example, encoding the same TCR) or polyclonal (for example, having clones encoding different TCRs) T cells that have T cell receptors recognizing at least one tumor antigen peptide. Activated T cells may include one or more subtypes of T cells, including, but not limited to, one or more selected from the group consisting of cytotoxic T cells, helper T cells, natural killer T cells, γδ T cells, regulatory T cells, and memory T cells, with memory T cells being preferred.

In the present invention, the activated T cells can treat a cancerous or neoplastic condition or prevent recurrence, progression, or metastasis of cancer while avoiding the defense mechanism of cancer cells.

According to still yet another embodiment of the present invention, there may be provided an antigen-presenting cell (APC) loaded with a cancer-specific tumor antigen epitope provided in the present invention.

In the present invention, the antigen-presenting cells may include at least one of dendritic cell (DC), B cell, and macrophage, with dendritic cell being preferred.

In the present invention, the "dendritic cell" refers to any member of a diverse population of morphologically similar cell types found in lymphoid or non-lymphoid tissues. These cells are characterized by their distinctive morphology and high expression levels of surface class I and class II MHC molecules, which are proteins that present antigenic peptides to T cells. DCs, other APCs, and T cells may be isolated or derived (such as differentiated) from a number of tissue sources, and conveniently from peripheral blood, such as peripheral blood mononuclear cells (PBMCs) derived from peripheral blood.

In the present invention, the antigen-presenting cell can induce differentiation and proliferation of cancer antigen-specific T cells, preferably memory T cells, thereby treating a cancerous or neoplastic condition or preventing recurrence, progression, or metastasis of cancer while avoiding the defense mechanism of cancer cells.

According to still yet another embodiment of the present invention, there is provided a fusion protein, comprising: a cancer-specific tumor antigen epitope provided in the present invention; and a dendritic cell-specific antibody or a fragment thereof.

The fusion protein provided in the present invention enables the cancer-specific tumor antigen epitope provided in the present invention to be loaded on dendritic cells.

In the present invention, the dendritic cell-specific antibody may include, but is not limited to, antibodies specific for DCIR, MHC class I, MHC class II, CD1, CD2, CD3, CD4, CD8, CD11b, CD14, CD15, CD16, CD19, CD20, CD29, CD31, CD40, CD43, CD44, CD45, CD54, CD56, CD57, CD58, CD83, CD86, CMRF-44, CMRF-56, DCIR, DC-ASPGR, CLEC-6, CD40, BDCA-2, MARCO, DEC-205, Clec9A, 33D1, mannose receptor, Langerin, DECTIN-1, B7-1, B7-2, IFN-γ receptor, IL-2 receptor, ICAM-1, Fcγ receptor, LOX-1, or ASPGR, which is on dendritic cells.

The cancer-specific tumor antigen epitope in the fusion protein of the present invention may be conjugated to the dendritic cell-specific antibody or a fragment thereof. Here, the term "conjugate" refers to any material formed by joining two parts together. A representative conjugate according to the present invention includes those formed by joining an antigen together with an antibody and a TLR agonist. The term "conjugation" refers to a process of forming a conjugate and generally indicates physical coupling, for example, covalent bond, co-coordinate covalent bond, or second binding force, for example, Van der Waals binding force. The process of linking the antigen to the antibody may also be done via a non-covalent association such as a dockerin-cohesin association (as described in U.S. Patent Publication No. 20100135994, Banchereau et al. relevant portions incorporated herein by reference) or via a direct chemical linkage by forming a peptide or chemical bond.

According to another embodiment of the present invention, there is provided a method for producing an antigen-presenting cell (APC), in which the antigen-presenting cell is loaded with a cancer-specific tumor antigen epitope provided in the present invention.

In the present invention, the antigen-presenting cell may include one or more of dendritic cell, B cell, and macrophage, with dendritic cell being preferred.

In the present invention, the dendritic cells (such as immature dendritic cells) may be obtained from a variety of sources including autologous sources, that is, derived from a target individual. The dendritic cells may preferably be obtained from peripheral blood mononuclear cells (PBMCs) derived from peripheral blood, and more preferably be obtained by isolating monocytes from individual-derived PBMCs and contacting the monocytes with a plurality of cytokines. Here, the type of cytokine that induces differentiation of the monocytes into dendritic cells is not particularly limited, and may include, for example, one or more of GM-CSF and IL-4.

In the present invention, the "target individual" means an individual who has or is at high risk of developing cancer.

In the present invention, once antigen-presenting cells are prepared as described above, the antigen-presenting cells may be loaded with a cancer-specific tumor antigen epitope of the present invention. In general, immature dendritic cells capture an antigen through phagocytosis or receptor-mediated endocytosis, process the antigen through a series of intracellular processes and then cause an antigenic peptide to be loaded on MHC and presented to T lymphocytes. With the process of processing an antigen, the dendritic cells become more mature, which makes them lose receptors used for phagocytosis and endocytosis, exhibit increased expression of MHC class I, II, costimulatory molecules, and adhesion molecules, and express new chemokine receptors. This allows the dendritic cells to migrate to T lymphocyte-rich areas of the surrounding lymph nodes, and to present the antigen to T lymphocytes, thereby causing a T lymphocyte immune response.

In an example of the present invention, in order for the cancer-specific tumor antigen epitope to be loaded on the antigen-presenting cell, the antigen-presenting cell may be contacted with the cancer-specific tumor antigen epitope of the present invention, and preferably, a step of pulsing, with the cancer-specific tumor antigen epitope of the present invention, the antigen-presenting cells, for example, immature dendritic cells, or antigen-presenting cells (such as dendritic cells) contained in or derived (for example, differentiated) from PBMCs may be performed. As known in the art, pulsing refers to a process of mixing cells, such as dendritic cells, with a solution containing an antigenic peptide of the present invention, and then optionally removing the antigenic peptide from the mixture. In the present invention, when the immature dendritic cells are contacted with the cancer-specific tumor antigen epitope, treatment with toll-like receptor agonists may be performed to further induce maturation of a population of immature dendritic cells. Here, exemplary TLR agonists include, but are not limited to, polyIC, MALP, and R848.

In another example of the present invention, in order for the cancer-specific tumor antigen epitope to be loaded on the antigen-presenting cell, it is possible to perform nucleofection of the antigen-presenting cell with an expression vector, preferably a plasmid, into which a nucleic acid molecule encoding the cancer-specific tumor antigen epitope is inserted. Here, the nucleofection may be performed by any useful means in the art, including, for example, Amaxa® nucleofection system or InVitrogen® nucleofection system.

In yet another example of the present invention, in order for the cancer-specific tumor antigen epitope to be loaded on the antigen-presenting cell, such loading may be performed using a fusion protein that contains the cancer-specific tumor antigen epitope provided in the present invention; and a dendritic cell-specific antibody or a fragment thereof.

According to still yet another embodiment of the present invention, there is provided a T cell activated by an antigen-presenting cell provided in the present invention.

In the present invention, the T cells refer to a population of monoclonal (for example, encoding the same TCR) or polyclonal (for example, having clones encoding different TCRs) T cells that have T cell receptors recognizing a tumor antigen peptide, and may include one or more subtypes of T cells, including, but not limited to, one or more selected from the group consisting of cytotoxic T cells, helper T cells, natural killer T cells, γδ T cells, regulatory T cells, and memory T cells, with memory T cells being preferred.

In the present invention, the "memory T cells" are T cells that have previously encountered and responded to their specific antigen, or T cells that have differentiated from activated T cells. Although tumor-specific memory T cells make up a small portion of the total T cell amount, they play an important function in surveillance of tumor cells during a person's entire lifespan. In a case where tumor-specific memory T cells encounter tumor cells that express their specific tumor antigen, the memory T cells are immediately activated and clonally expanded. The activated and expanded T cells differentiate into effector T cells to kill tumor cells with high efficiency. Memory T cells are important for establishing and maintaining long-term tumor antigen-specific responses of T cells. In the present invention, activated T cells, preferably activated memory T cells, specifically recognize antigens on cancer cells, so that such T cells can treat a cancerous or neoplastic condition or prevent recurrence, progression, or metastasis of cancer while avoiding the defense mechanism of cancer cells.

According to still yet another embodiment of the present invention, there is provided a method for activating T cells using an antigen-presenting cell (APC) provided in the present invention.

In the present invention, for activation of the T cells, the T cells may be co-cultured with antigen-presenting cells loaded with a cancer-specific tumor antigen epitope of the present invention.

In the present invention, the T cells may be obtained from various sources including autologous sources, that is, derived from a target individual, may preferably be obtained from peripheral blood mononuclear cells (PBMCs) derived from peripheral blood, and may more preferably be obtained from non-adherent portions of the peripheral blood mononuclear cells. In an example of the present invention, the non-adherent portions of the PBMCs may be obtained by density gradient centrifugation of a peripheral blood sample, or may be obtained by performing culture with at least one cytokine (such as IL-2) in the presence or absence of an anti-CD3 antibody (such as OKT3).

In the present invention, the T cells refer to a population of monoclonal (for example, encoding the same TCR) or polyclonal (for example, having clones encoding different TCRs) T cells that have T cell receptors recognizing a tumor antigen peptide, and may include one or more subtypes of T cells, including, but not limited to, one or more selected from the group consisting of cytotoxic T cells, helper T cells, natural killer T cells, γδ T cells, regulatory T cells, and memory T cells, with memory T cells being preferred.

In addition, in the present invention, the T cells and the antigen-presenting cells may be derived from the same individual, such as an individual suffering from cancer (for example, low to medium grade cancer). However, the present invention is not limited thereto.

In the present invention, for activation of the T cells, the T cells may be co-cultured with antigen-presenting cells of the present invention for any one or more time periods of 1, 2, 3, 4, 6, 8, 10, 12, 14, 16, 18, 20, 22, 24, 26, 28, or 30 days, and preferably for 1 to 21 days, 1 to 14 days, 2 to 10 days, 2 to 5 days, 2 to 5 days, 3 days, 5 days, 7 days, 10 days, 14 days, 16 days, 18 days, or 21 days. However, the present invention is not limited thereto.

In the present invention, during the co-culture of the T cells with antigen-presenting cells of the present invention, one or more cytokines may be added to prime the T cells so that activation, maturation and/or proliferation of the T cells are promoted and the T cells subsequently differentiate into memory T cells. Exemplary cytokines that may be used at this stage include, but are not limited to, interleukin-2 (IL-2), interleukin-4 (IL-4), interleukin-7 (IL-7), interleukin-15 (IL-15), interleukin-21 (IL-21), or combinations thereof, and the like.

In addition, in the present invention, during the co-culture of the T cells with antigen-presenting cells of the present invention, a fusion protein comprising a cytokine and an immunoglobulin heavy chain constant region may be added to prime the T cells so that activation, maturation and/or proliferation of the T cells are promoted and the T cells subsequently differentiate into memory T cells. Here, the cytokine may include, but is not limited to, interferon-γ (IFN-γ), interleukin-2 (IL-2), interleukin-4 (IL-4), interleukin-12 (IL-12), interleukin-18 (IL-18), and tumor necrosis factor (TNF), or granulocyte macrophage colony stimulating factor (GMCSF). The immunoglobulin heavy chain constant region may also be, but is not limited to, an immunoglobulin hinge region, and an immunoglobulin heavy chain constant region optionally selected from the group consisting of CH2 domain, CH3 domain, and CH4 domain, or combinations thereof. In addition, the immunoglobulin heavy chain constant region may be derived from immunoglobulins belonging to any of five immunoglobulin classes called in the art as IgA (Igα), IgD (Igδ), IgE (Igε), IgG (Igγ), and IgM (Igμ), and may preferably be an immunoglobulin heavy chain constant region derived from the IgG class.

In addition, in the present invention, during the co-culture of the T cells with antigen-presenting cells of the present invention, a fusion protein that contains ligand binding to a cell surface protein which is highly expressed in memory T cells; and an immunoglobulin heavy chain constant region, may be added to prime the T cells so that activation, maturation and/or proliferation of the T cells are promoted and the T cells subsequently differentiate into memory T cells. Here, the cell surface protein which is highly expressed in memory T cells may be CD27, CXCR3, or CD62L. The ligand capable of binding to CD27 may be CD70; the ligand capable of binding to CXCR3 may be CXCR9 or CXCR10; and the ligand capable of binding to CD62L may be GlyCAM-1, CD34, MadCAM-1, or PSGL-1. However, the present invention is not limited thereto. In addition, the immunoglobulin heavy chain constant region may be derived from immunoglobulins belonging to any of five immunoglobulin classes called in the art as IgA (Igα), IgD (Igδ), IgE (Igε), IgG (Igγ), and IgM (Igμ), and may preferably be an immunoglobulin heavy chain constant region derived from the IgG class.

According to still yet another embodiment of the present invention, there is provided an immunotherapeutic agent, comprising, as an active ingredient, an antigen-presenting cell loaded with a cancer-specific tumor antigen epitope provided in the present invention. The immunotherapeutic agent according to the present invention can increase immune responses or may selectively increase some of immune responses desired for treatment or prevention of a certain disease, for example, cancer.

According to still yet another embodiment of the present invention, there is provided an anticancer vaccine or a pharmaceutical composition for preventing or treating cancer, comprising, as an active ingredient, an antigen-presenting cell loaded with a cancer-specific tumor antigen epitope provided in the present invention; and/or an activated T cell.

The antigen-presenting cell provided in the present invention enables induction of differentiation and proliferation of cancer antigen-specific T cells, preferably memory T cells, and the memory T cells thus activated can treat a cancerous or neoplastic condition or prevent recurrence, progression, or metastasis of cancer while avoiding the defense mechanism of cancer cells.

As used herein, the term "cancer" refers to or indicates a physiological condition characterized by cell growth in mammals which is not regulated in a typical manner. The cancer to be prevented, ameliorated, or treated in the present invention may be Epstein-Barr virus (EBV)-negative cancer, including, without limitation, any cancer species as long as it expresses a neoepitope represented by any one of SEQ ID NOs: 1 to 214 of the present invention. Thus, the type thereof is not particularly limited, and examples thereof may include, but are not limited to, colorectal cancer, pancreatic cancer, gastric cancer, liver cancer, breast cancer, cervical cancer, thyroid cancer, parathyroid cancer, lung cancer, non-small cell lung cancer, prostate cancer, gallbladder cancer, biliary tract cancer, non-Hodgkin lymphoma, Hodgkin lymphoma, blood cancer, bladder cancer, kidney cancer, ovarian cancer, melanoma, colon cancer, bone cancer, skin cancer, head cancer, uterine cancer, rectal cancer, brain tumor, perianal cancer, fallopian tube carcinoma, endometrial carcinoma, vaginal cancer, vulvar carcinoma, esophageal cancer, small intestine cancer, endocrine adenocarcinoma, adrenal cancer, soft tissue sarcoma, urethral cancer, penile cancer, ureteral cancer, renal cell carcinoma, renal pelvic carcinoma, central nervous system (CNS) tumor, primary CNS lymphoma, spinal cord tumor, brain stem glioma, or pituitary adenoma, with gastric cancer being preferred.

In the present invention, the "prevention" may include, without limitation, any act of blocking symptoms of cancer, or suppressing or delaying the symptoms, using the pharmaceutical composition of the present invention.

In addition, in the present invention, the "treatment" may include, without limitation, any act of ameliorating or beneficially altering symptoms of cancer, using the pharmaceutical composition of the present invention.

In the present invention, the pharmaceutical composition may be characterized by being in the form of capsules, tablets, granules, injections, ointments, powders, or beverages, and the pharmaceutical composition may be characterized by being targeted to humans.

In the present invention, the pharmaceutical composition may be formulated in the form of oral preparations such as powders, granules, capsules, tablets, and aqueous suspensions, preparations for external use, suppositories, and sterile injectable solutions, respectively, according to conventional methods, and used. However, the pharmaceutical composition is not limited thereto. The pharmaceutical composition of the present invention may further comprise a pharmaceutically acceptable carrier. As the pharmaceutically acceptable carrier, a binder, a glidant, a disintegrant, an excipient, a solubilizer, a dispersant, a stabilizer, a suspending agent, a pigment, a flavor, and the like may be used for oral administration; a buffer, a preserving agent, a pain-relieving agent, a solubilizer, an isotonic agent, a stabilizer, and the like may be used in admixture for injections; and a base, an excipient, a lubricant, a preserving agent, and the like may be used for topical administration. The preparations of the pharmaceutical composition of the present invention may be prepared in various ways by being mixed with the pharmaceutically acceptable carrier as described above. For example, for oral administration, the pharmaceutical composition may be formulated in the form of tablets, troches, capsules, elixirs, suspensions, syrups, wafers, or the like. For injections, the pharmaceutical composition may be formulated in the form of unit dosage ampoules or multiple dosage forms. Alternatively, the pharmaceutical composition may be formulated into solutions, suspensions, tablets, capsules, sustained-release preparations, or the like.

Meanwhile, as examples of carriers, diluents, or excipients suitable for making preparations, lactose, dextrose, sucrose, sorbitol, mannitol, xylitol, erythritol, maltitol, starch, gum acacia, alginate, gelatin, calcium phosphate, calcium silicate, cellulose, methyl cellulose, microcrystalline cellulose, polyvinylpyrrolidone, water, methyl hydroxybenzoate, propyl hydroxybenzoate, talc, magnesium stearate, mineral oil, or the like may be used. In addition, a filler, an anti-coagulant, a lubricant, a wetting agent, a fragrance, an emulsifier, a preservative, and the like may further be included.

The route of administration of the pharmaceutical composition of the present invention includes, but is not limited to, oral, intravenous, intramuscular, intraarterial, intramedullary, intradural, intracardiac, transdermal, subcutaneous, intraperitoneal, intranasal, intestinal, topical, sublingual, or rectal route. Oral or parenteral administration is preferred.

As used herein, the term "parenteral" includes subcutaneous, intradermal, intravenous, intramuscular, intraarticular, intrabursal, intrasternal, intradural, intralesional, and intracranial injection or infusion techniques. The pharmaceutical composition of the present invention may also be administered in the form of suppositories for rectal administration.

The pharmaceutical composition of the present invention may vary depending on a variety of factors, including activity of a certain compound used, the patient's age, body weight, general health status, sex, diet, time of administration, route of administration, rate of excretion, drug combination, and severity of a certain disease to be prevented or treated. A dose of the pharmaceutical composition may vary depending on the patient's condition, body weight, severity of disease, drug form, route of administration, and duration, and may be appropriately selected by those skilled in the art. The pharmaceutical composition may be administered in an amount of 0.0001 to 50 mg/kg or 0.001 to 50 mg/kg, per day. Administration may be made once a day or several times a day. The dose is not intended to limit the scope of the present invention in any way. The pharmaceutical composition according to the present invention may be formulated in the form of pills, sugar-coated tablets, capsules, liquids, gels, syrups, slurries, or suspensions.

According to still yet another embodiment of the present invention, there is provided a method for preventing or treating cancer, comprising a step of administering, to a target individual, an antigen-presenting cell loaded with a cancer-specific tumor antigen epitope provided in the present invention; and/or an activated T cell.

Dose, schedule, and route of administration of the antigen-presenting cell loaded with a cancer-specific tumor antigen epitope provided in the present invention or the activated T cell may be determined depending on the size and condition of an individual, and in accordance with standard pharmaceutical practice. Exemplary routes of administration include intravenous, intraarterial, intraperitoneal, intrapulmonary, intravascular, intramuscular, intratracheal, subcutaneous, intraocular, intrathecal, or transdermal route.

A dose of cells administered to an individual may vary depending, for example, on the particular type of cells being administered, the route of administration, and the particular type and stage of cancer being treated. The amount should be sufficient to produce a desirable response, such as a therapeutic response against cancer, but without severe toxicity or adverse events. In some embodiments, the amount of activated T cells or antigen-presenting cells (such as dendritic cells) to be administered is a therapeutically effective amount. In some embodiments, the amount of cells (such as dendritic cells loaded with a cancer-specific tumor antigen epitope or activated T cells) is an amount sufficient to decrease the size of a tumor, decrease the number of cancer cells, or decrease the growth rate of a tumor by any one of at least about 10%, 20%, 30%, 40%, 50%, 60%, 70%, 80%, 90%, 95%, or 100%, as compared with the corresponding tumor size, number of cancer cells, or tumor growth rate in the same individual prior to treatment or as compared with the corresponding activity in other individuals having not received the treatment. The magnitude of effects may be measured using standard methods, such as in vitro assays with purified enzymes, cell-based assays, animal models, or experiments using humans.

In an embodiment of the present invention, the antigen-presenting cells (such as dendritic cells) loaded with a cancer-specific tumor antigen epitope of the present invention may be administrated at a dose of any of $1 \times 10^5$ to $5 \times 10^5$, $5 \times 10^5$ to $1 \times 10^6$, $1 \times 10^6$ to $2 \times 10^6$, $2 \times 10^6$ to $3 \times 10^6$, $3 \times 10^6$ to $4 \times 10^6$, $4 \times 10^6$ to $5 \times 10^6$, $5 \times 10^6$ to $6 \times 10^6$, $6 \times 10^6$ to $7 \times 10^6$, $7 \times 10^6$ to $8 \times 10^6$, $8 \times 10^6$ to $1 \times 10^8$, $1 \times 10^6$ to $3 \times 10^6$, $3 \times 10^6$ to $5 \times 10^6$, $5 \times 10^6$ to $7 \times 10^6$, $2 \times 10^6$ to $4 \times 10^6$, $1 \times 10^6$ to $5 \times 10^6$, or $5 \times 10^6$ to $1 \times 10^7$ cells/individual. However, the present invention is not limited thereto.

In another embodiment of the present invention, the antigen-presenting cells (e.g., dendritic cells) loaded with a cancer-specific tumor antigen epitope of the present invention may be administrated at a dose of any of $1 \times 10^4$ to $5 \times 10^4$, $5 \times 10^4$ to $1 \times 10^5$, $1 \times 10^5$ to $2 \times 10^5$, $2 \times 10^5$ to $4 \times 10^5$, $4 \times 10^5$ to $6 \times 10^5$, $6 \times 10^5$ to $8 \times 10^5$, $8 \times 10^5$ to $1 \times 10^6$, $1 \times 10^6$ to $2 \times 10^6$, $2 \times 10^6$ to $1 \times 10^7$, $1 \times 10^4$ to $1 \times 10^5$, $1 \times 10^5$ to $1 \times 10^6$, $1 \times 10^6$ to $1 \times 10$, $1 \times 10^4$ to $1 \times 10^6$, or $1 \times 10^5$ to $1 \times 10^7$ cells/kg. However, the present invention is not limited thereto.

In addition, in an embodiment of the present invention, the activated T cells of the present invention may be administrated at a dose of any of $1 \times 10^8$ to $5 \times 10^8$, $5 \times 10^8$ to $9 \times 10^8$, $9 \times 10^8$ to $1 \times 10^9$, $1 \times 10^9$ to $2 \times 10^9$, $2 \times 10^9$ to $3 \times 10^9$, $3 \times 10^9$ to $4 \times 10^9$, $4 \times 10^9$ to $5 \times 10^9$, $5 \times 10^9$ to $6 \times 10^9$, $6 \times 10^9$ to $1 \times 10^{10}$, $1 \times 10^9$ to $3 \times 10^9$, $3 \times 10^9$ to $5 \times 10^9$, $5 \times 10^9$ to $7 \times 10^9$, $7 \times 10^9$ to $1 \times 10^{10}$, $1 \times 10^9$ to $5 \times 10^9$, $5 \times 10^9$ to $1 \times 10^{10}$, $3 \times 10^9$ to $7 \times 10^9$, $1 \times 10^{10}$ to $1.5 \times 10^{10}$, $1 \times 10^{10}$ to $2 \times 10^{10}$, or $1 \times 10^9$ to $1 \times 10^{10}$ cells/individual. However, the present invention is not limited thereto.

In another embodiment of the present invention, the activated T cells of the present invention may be administrated at a dose of any of $1 \times 10^7$ to $1 \times 10^8$, $1 \times 10^8$ to $2 \times 10^8$, $2 \times 10^8$ to $4 \times 10^8$, $4 \times 10^8$ to $6 \times 10^8$, $6 \times 10^8$ to $8 \times 10^8$, $8 \times 10^8$ to $1 \times 10^9$, $1 \times 10^9$ to $2 \times 10^9$, $2 \times 10^9$ to $4 \times 10^9$, $4 \times 10^9$ to $1 \times 10^{10}$, $2 \times 10^8$ to $6 \times 10^8$, $6 \times 10^8$ to $1 \times 10^9$, $1 \times 10^8$ to $2 \times 10^8$, $2 \times 10^8$ to $2 \times 10^9$, $1 \times 10^7$ to $1 \times 10^8$, $1 \times 10^8$ to $1 \times 10^9$, $1 \times 10^9$ to $1 \times 10^{10}$, or $1 \times 10^7$ to $1 \times 10^9$ cells/kg. However, the present invention is not limited thereto.

In the present invention, a stabilizer or excipient such as human albumin may be used together with administration of the antigen-presenting cells (such as dendritic cells) loaded with a cancer-specific tumor antigen epitope and/or the activated T cells.

In the present invention, dose and dosing schedule of the antigen-presenting cells (such as dendritic cells) loaded with a cancer-specific tumor antigen epitope and/or the activated T cells may be adjusted over the course of treatment based on the judgment of the administering physician. In some embodiments, the activated T cells may be administered at any time point of about 1 day, 2 days, 3 days, 4 days, 5 days, 6 days, 7 days, 8 days, 9 days, 10 days, 11 days, 12 days, 13 days, 14 days, 15 days, 16 days, 17 days, 18 days, 19 days, 20 days, 21 days, or 1 month after the antigen-presenting cells loaded with a tumor antigen peptide are administered, or may be administered simultaneously with the antigen-presenting cells. However, the present invention is not limited thereto.

In the present invention, administration of the antigen-presenting cells (such as dendritic cells) loaded with a cancer-specific tumor antigen epitope and/or the activated T cell may be done alone or in combination with other therapies, such as surgery, radiation therapy, gene therapy, immunotherapy, bone marrow transplantation, stem cell transplantation, hormone therapy, targeted therapy, cryotherapy, ultrasound therapy, photodynamic therapy, chemotherapy, or the like. Additionally, a person having a greater risk of developing a proliferative disease may receive treatments to inhibit and/or delay development of the disease.

ADVANTAGEOUS EFFECTS OF INVENTION

The antigen-presenting cell, that is, dendritic cell, loaded with a cancer-specific tumor antigen epitope provided in the present invention enables rapid and effective induction of differentiation and proliferation of cancer antigen-specific T cells, preferably memory T cells, and the memory T cells thus activated can treat cancerous or neoplastic condition or prevent recurrence, progression, or metastasis of cancer while avoiding the defense mechanism of cancer cells.

In the conventional adoptive T cell therapies, it takes a long time of 3 to 6 months to produce a large number of T cells for treatment of cancer patients, which poses a big problem in the cell production process in immune cell therapy. However, according to the present invention, $10^9$ autologous memory T cells, which should be used for patient treatment, can be produced within three weeks, and cost reduction and minimized infection risk factors to external contaminants can be achieved. Accordingly, according to the present invention, there is provided a technique that can be applied to terminal cancer patients because such a technique makes rapid therapeutic approaches available for a larger number of solid cancer patients.

BRIEF DESCRIPTION OF DRAWINGS

FIG. 1 illustrates results obtained by identifying, through IFN-γ ELISPOT, a proportion of cells that secrete IFN-γ, in T cells stimulated with dendritic cells loaded with a neoepitope (10-mer) of EBV-negative gastric cancer antigen, and unstimulated control cells, to identify antigen specificity of EBV-negative gastric cancer-specific autologous memory T cells (HLA-A2402) produced according to an embodiment of the present invention. In the FIG. 1, the first bar indicates the result of EBV-negative neoepitope represented by SEQ ID NO: 45 and the second bar indicates the result of EBV- negative neoepitope represented by SEQ ID NO: 42 and the third bar indicates the result of EBV-negative neoepitope represented by SEQ ID NO: 49 and the fourth bar indicates the result of control represented by SEQ ID NO: 215.

FIG. 2 illustrates results obtained by identifying, through IFN-γ ELISPOT, a proportion of cells that secrete IFN-γ, in T cells stimulated with dendritic cells loaded with a neoepitope (10-mer) of EBV-negative gastric cancer antigen, and unstimulated control cells, to identify antigen specificity of EBV-negative gastric cancer-specific autologous memory T cells (HLA-A2402) produced according to an embodiment of the present invention. In the FIG. 2, the first bar indicates the result of EBV-negative neoepitope represented by SEQ ID NO: 32 and the second bar indicates the result of EBV- negative neoepitope represented by SEQ ID NO: 41 and the third bar indicates the result of EBV-negative neoepitope represented by SEQ ID NO: 48 and the fourth bar indicates the result of control represented by SEQ ID NO: 215.

FIG. 3 illustrates results obtained by identifying, through IFN-γ ELISPOT, a proportion of cells that secrete IFN-γ, in T cells stimulated with dendritic cells loaded with a neoepitope (10-mer) of EBV-negative gastric cancer antigen, and unstimulated control cells, to identify antigen specificity of EBV-negative gastric cancer-specific autologous memory T cells (HLA-A0201) produced according to an embodiment of the present invention. In the FIG. 3, the first bar in indicates the result of EBV-negative neoepitope represented by SEQ ID NO: 122 and the second bar indicates the result of EBV-negative neoepitope represented by SEQ ID NO: 173 and the third bar indicates the result of EBV-negative neoepitope represented by SEQ ID NO: 214 and the fourth bar indicates the result of control represented by SEQ ID NO: 215.

FIG. 4 illustrates results obtained by identifying, through IFN-γ ELISPOT, a proportion of cells that secrete IFN-γ, in T cells stimulated with dendritic cells loaded with a neoepitope (10-mer) of EBV-negative gastric cancer antigen, and unstimulated control cells, to identify antigen specificity of EBV-negative gastric cancer-specific autologous memory T cells (HLA-A0201) produced according to an embodiment of the present invention. In the FIG. 4, the first bar indicates the result of EBV-negative neoepitope represented by SEQ ID NO: 123 and the second bar indicates the result of EBV-negative neoepitope represented by SEQ ID NO: 174 and the third bar indicates the result of EBV-negative neoepitope represented by SEQ ID NO: 213 and the fourth bar indicates the result of control represented by SEQ ID NO: 215.

DETAILED DESCRIPTION OF INVENTION

According to an embodiment of the present invention, there is provided an Epstein-Barr virus (EBV)-negative cancer-specific tumor antigen neoepitope, represented by any one of SEQ ID NOs: 1 to 214.

According to another embodiment of the present invention, there is provided an antigen-presenting cell (APC) loaded with a cancer-specific tumor antigen neoepitope provided in the present invention.

According to yet another embodiment of the present invention, there is provided a T cell activated by an antigen-presenting cell provided in the present invention.

According to still yet another embodiment of the present invention, there is provided an anticancer vaccine or a pharmaceutical composition for preventing or treating cancer, comprising, as an active ingredient, an antigen-presenting cell loaded with a cancer-specific tumor antigen epitope provided in the present invention; and/or an activated T cell.

Hereinafter, the present invention will be described in more detail by way of examples. These examples are only for describing the present invention in more detail, and it will be apparent to those skilled in the art that according to the gist of the present invention, the scope of the present invention is not limited by these examples.

EXAMPLES

Example 1

Production Method of Autologous Memory T Cells Specific to EBV-Negative Gastric Cancer Cells and Clinical Application Thereof 1. Selection of EBV-Negative Gastric Cancer Cell Antigen Neoepitopes Algorithms for predicting the most important sequence with accumulation of genetic mutations in gastric cancer cells and for predicting epitopes of this sequence which bind to HLA of T cells were developed using Neopepsee. Here, using the neoepitope prediction algorithms, peptide sequences were identified which are expected to have high binding affinity with HLA types (HLA-A2402, HLA-A0201) that Koreans express the most. To this end, missense mutations expressed into mRNAs were predicted through whole-exome sequencing and RNAseq data analysis of all EBV-negative gastric cancer patients currently present in TCGA. For binding affinity between each HLA type and the identified neoepitope, Neopepsee final scores were calculated considering both $IC_{50}$ values (nM) obtained from NetMHC and rank-based predictive values of MHC-peptide binding obtained from NetCTLpan, and further considering all of protein cleavage, hydrophobicity of amino acids in TCR contact residues, polarity and charged values of amino acids, and molecular size and peptide entropy. In this way, possibility of cancer-specific neoantigens was finally predicted, so that neoepitopes were identified.

Tables 1 to 6 below show sequences that are expected to be neoepitopes, corresponding genes expressing the sequences, and normal sequences, obtained by analysis of RNAseq data of patients expressing HLA-A2402 and HLA-A0201 which are known to be most expressed in Koreans, which provides prediction of binding affinity between each of the present sequences and HLA, and thus provides prediction of types of neoepitopes that can be used when producing actual cell therapeutic agents.

TABLE 1

| Neoepitope (8-mer) with high binding affinity for HLA-A2402 | | | | | | | | | | | |
|---|---|---|---|---|---|---|---|---|---|---|---|
| transcript | gene | chr | pos | ref | alt | expr (RPKM) | WT_AA | MT_AA | MTpep | MT_ic50 | Score level |
| hg19_knownGene_uc002hhp.1, hg19_knownGene_uc002hho.1, hg19_knownGene_uc010wcb.2 | MYO1D | chr17 | 31087632 | C | T | 0 | FAKAIYERLFCWIVT | FAKAIYEHLFCWIVT | SEQ ID NO: 1 IYEHLFCW | 379 | medium |

TABLE 2

Neoepitopes (9-mer) with high binding affinity for HLA-A2402

| transcript | gene | chr | pos | ref | alt | expr (RPKM) | WT_AA | MT_AA | MTpep | MT_ic50 | Score level |
|---|---|---|---|---|---|---|---|---|---|---|---|
| hg19_knownGene_uc011koz.2, hg19_knownGene_uc003vow.3, hg19_knownGene_uc011koy.2 | STRIP2 | chr7 | 1.29E+08 | C | T | 0 | MSAIYQKVRHRMNDDWA | MSAIYQKVCHRMNDDWA | SEQ ID NO: 2 IYQKVCHRM | 35 | high |
| hg19_knownGene_uc002xjc.3 | SLC32A1 | chr20 | 37357184 | G | A | 0 | LWHQVFFDVAIFVIGGI | LWHQVFFDIAIFVIGGI | SEQ ID NO: 3 LWHQVFFDI | 70 | high |
| hg19_knownGene_uc010egi.2, hg19_knownGene_uc002ojt.2, hg19_knownGene_uc002ojv.2, hg19_knownGene_uc002ojs.2, hg19_knownGene_uc002oju.2, hg19_knownGene_uc010egh.2 | SIRT2 | chr19 | 39380364 | C | T | 0 | KKHPEPFFALAKELYPG | KKHPEPFFTLAKELYPG | SEQ ID NO: 4 KHPEPFFTL | 132 | high |
| hg19_knownGene_uc002hso.3, hg19_knownGene_uc010cwa.3, hg19_knownGene_uc002hsp.3, hg19_knownGene_uc010cwb.3, hg19_knownGene_uc002hsm.3, hg19_knownGene_uc010wek.2 | ERBB2 | chr17 | 37881332 | G | A | 0 | SYLEDVRLVHRDLAARN | SYLEDVRLIHRDLAARN | SEQ ID NO: 5 SYLEDVRLI | 54 | high |
| hg19_knownGene_uc002hue.3, hg19_knownGene_uc010cwt.1 | CASC3 | chr17 | 38325584 | C | T | 0 | LYPNTQAPSQVYGGVTY | LYPNTQAPLQVYGGVTY | SEQ ID NO: 6 LYPNTQAPL | 184 | high |
| hg19_knownGene_uc002bxi.3, hg19_knownGene_c002bxh.3, hg19_knownGene_uc002bxj.3 | TM2D3 | chr15 | 1.02E+08 | G | A | 0 | SFGGLGIWTLIDVLLIG | SFGGLGIWMLIDVLLIG | SEQ ID NO: 7 IWMLIDVLL | 394 | high |

TABLE 2-continued

Neoepitopes (9-mer) with high binding affinity for HLA-A2402

| transcript | gene | chr | pos | ref | alt | expr (RPKM) | WT_AA | MT_AA | MTpep | | MT_ic50 | Score level |
|---|---|---|---|---|---|---|---|---|---|---|---|---|
| hg19_knownGene_uc001ypu.1, hg19_knownGene_uc010tyl.1 | PLD4 | chr14 | 1.05E+08 | G | A | 0 | QNFSSHFNRFQPFHGLF | QNFSSHFNHFQPFHGLF | SEQ ID NO: 8 | NFSSHFNHF | 83 | medium |
| hg19_knownGene_uc001ypu.1, hg19_knownGene_uc010tyl.1 | PLD4 | chr14 | 1.05E+08 | G | A | 0 | QNFSSHFNRFQPFHGLF | QNFSSHFNHFQPFHGLF | SEQ ID NO: 9 | HFQPFHGLF | 89 | high |
| hg19_knownGene_uc003lir.3 | PCDHB6 | chr5 | 1.41E+08 | C | T | 0 | INAITGEIRLRKALDFE | INAITGEIWLRKALDFE | SEQ ID NO: 10 | IWLRKALDF | 36 | high |
| hg19_knownGene_uc002wto.1 | CST4 | chr20 | 23669411 | G | A | 0 | ATEDEYYRRPLQVLRAR | ATEDEYYRCPLQVLRAR | SEQ ID NO: 11 | YYRCPLQVL | 159 | high |
| hg19_knownGene_uc003jml.2, hg19_knownGene_uc003jmk.3 | C6 | chr5 | 41149516 | T | G | 0 | DYFTSPACKFLAEKCLN | DYFTSPACTFLAEKCLN | SEQ ID NO: 12 | YFTSPACTF | 127 | high |
| hg19_knownGene_uc003lqh.3, hg19_knownGene_uc010jgy.3, hg19_knownGene_uc003lqg.4 | AFAP1L1 | chr5 | 1.49E+08 | C | T | 0 | CRICAFLLRKKRFGQWA | CRICAFLLWKKRFGQWA | SEQ ID NO: 13 | AFLLWKKRF | 325 | medium |
| hg19_knownGene_uc021qya.1, hg19_knownGene_uc001rzn.3, hg19_knownGene_uc010snn.2 | ACVR1B | chr12 | 52387827 | G | A | 0 | CWYANGAARLTALRIKK | CWYANGAAHLTALRIKK | SEQ ID NO: 14 | WYANGAAHL | 219 | medium |
| hg19_knownGene_uc010epz.3, hg19_knownGene_uc021uyx.1, hg19_knownGene_uc010epx.3, hg19_knownGene_uc010epy.3, hg19_knownGene_uc010eps.3, hg19_knownGene_uc010epv.3, hg19_knownGene_uc010epw.3, | ZNF83 | chr19 | 53116566 | A | G | 0 | FSQNSYLAYHWRIHTGE | FSQNSYLAHHWRIHTGE | SEQ ID NO: 15 | SYLAHHWRI | 10 | high |

TABLE 2-continued

Neoepitopes (9-mer) with high binding affinity for HLA-A2402

| transcript | gene | chr | pos | ref | alt | expr (RPKM) | WT_AA | MT_AA | MTpep | | MT_ic50 | Score level |
|---|---|---|---|---|---|---|---|---|---|---|---|---|
| hg19_knownGene_uc010eqb.2, hg19_knownGene_uc002pzu.4, hg19_knownGene_uc002pzv.4, hg19_knownGene_uc031rmq.1, hg19_knownGene_uc031rmp.1, hg19_knownGene_uc031rmm.1, hg19_knownGene_uc031rmn.1, hg19_knownGene_uc031rml.1, hg19_knownGene_uc031rmo.1, hg19_knownGene_uc010epu.3, hg19_knownGene_uc010ept.3 | | | | | | | | | | | | |
| hg19_knownGene_bnm.4, hg19_knownGene_uc001bnn.3 | SLC9A1 | chr1 | 27436202 | C | T | 0 | VGIVDIFLGFLSFFVVA | VGIVDIFLSFLSFFVVA | SEQ ID NO: 16 | IFLSFLSSFF | 59 | high |
| hg19_knownGene_su1.3 | SLC6A15 | chr12 | 85279797 | G | A | 0 | MVIGIPLFFLELSVG | MVIGIPFFFLELSVG | SEQ ID NO: 17 | MVIGIPFFF | 216 | high |
| hg19_knownGene_uc001szy.4, hg19_knownGene_uc001szv.4 | SLC6A15 | chr12 | 85279797 | G | A | 0 | LLMVIGIPLFFLELSVG | LLMVIGIPFFFLELSVG | SEQ ID NO: 18 | MVIGIPFFF | 216 | high |
| hg19_knownGene_uc011mdo.2 | SARDH | chr9 | 1.37E+08 | G | A | 0 | MSLGKAYGVESHVL | MSLGKVYGVESHVL | SEQ ID NO: 19 | VYGVESHVL | 161 | high |
| hg19_knownGene_uc004cep.4, hg19_knownGene_uc004ceo.3, hg19_knownGene_uc011mdn.2 | SARDH | chr9 | 1.37E+08 | G | A | 0 | KRLMSLGKAYGVESHVL | KRLMSLGKVYGVESHVL | SEQ ID NO: 20 | VYGVESHVL | 161 | high |

TABLE 2-continued

Neoepitopes (9-mer) with high binding affinity for HLA-A2402

| transcript | gene | chr | pos | ref | alt | expr (RPKM) | WT_AA | MT_AA | MTpep | | MT_ic50 | Score level |
|---|---|---|---|---|---|---|---|---|---|---|---|---|
| hg19_knownGene_uc003xrh.12, hg19_knownGene_uc022aup.1, hg19_knownGene_uc010lyc.1, hg19_knownGene_uc003xri.1 | OPRK1 | chr8 | 54142147 | C | T | 0 | LVVVAVFVVCWTPIHIF | LVVVAVFVICWTPIHIF | SEQ ID NO: 21 | VFVICWTPI | 297 | high |
| hg19_knownGene_uc002hhp.1 hg19_knownGene_uc002hho.1, hg19_knownGene_uc010wcb.2 | MYO1D | chr17 | 31087632 | C | T | 0 | AFAKAIYERLFCWIVTR | AFAKAIYEHLFCWIVTR | SEQ ID NO: 22 | IYEHLFCWI | 195 | high |
| hg19_knownGene_uc002puu.1, hg19_knownGene_uc002puq.1, hg19_knownGene_uc002pur.1 | KLK8 | chr19 | 51503767 | G | A | 0 | QPHSQPWQAALFQGQQL | QPHSQPWQVALFQGQQL | SEQ ID NO: 23 | SQPWQVALF | 132 | high |
| hg19_knownGene_uc003bve.1 | IRAK2 | chr3 | 10264468 | C | T | 0 | AYLPEDFIRVGQLTKRV | AYLPEDFIWVGQLTKRV | SEQ ID NO: 24 | AYLPEDFIW | 364 | high |
| hg19_knownGene_uc002dli.3 | HS3ST2 | chr16 | 22926539 | G | A | 0 | NAIRIGMYVLHLESWLQ | NAIRIGMYMLHLESWLQ | SEQ ID NO: 25 | MYMLHLESW | 23 | high |
| hg19_knownGene_uc003sys.3 | HOXA7 | chr7 | 27194754 | G | A | 0 | EFHFNRYLTRRRRIEIA | EFHFNRYLMRRRRIEIA | SEQ ID NO: 26 | RYLMRRRRI | 73 | medium |
| hg19_knownGene_uc003xeg.3, hg19_knownGene_uc003xef.3 | DOCK5 | chr8 | 25158099 | T | C | 0 | QSTFISENYLIRWGSNG | QSTFISENHLIRWGSNG | SEQ ID NO: 27 | TFISENHLI | 63 | high |
| hg19_knownGene_uc011dzr.2, hg19_knownGene_uc011dzt.2, hg19_knownGene_uc010kbz.3, hg19_knownGene_uc010kca.3, hg19_knownGene_uc003pmq.4, hg19_knownGene_uc011dzs.2, | CNR1 | chr6 | 88853864 | G | A | 0 | GKMNKLIKTVFAFCSML | GKMNKLIKMVFAFCSML | SEQ ID NO: 28 | KLIKMVFAF | 208 | high |

TABLE 2-continued

Neoepitopes (9-mer) with high binding affinity for HLA-A2402

| transcript | gene | chr | pos | ref | alt | expr (RPKM) | WT_AA | MT_AA | MTpep | | MT_ic50 | Score level |
|---|---|---|---|---|---|---|---|---|---|---|---|---|
| hg19_knownGene_uc021zco.1 | | | | | | | | | | | | |
| hg19_knownGene_uc003smv.3 | CARD11 | chr7 | 2956965 | G | A | 0 | TSDPRVSPRLSRASFLF | TSDPRVSPCLSRASFLF | SEQ ID NO: 29 | CLSRASFLF | 35 | high |
| hg19_knownGene_uc003suw.4, hg19_knownGene_uc010kuh.3 | ABCB5 | chr7 | 20782555 | G | A | 0 | EVSFFYPCRPDVFILRG | EVSFFYPCHPDVFILRG | SEQ ID NO: 30 | FYPCHPDVF | 51 | medium |

TABLE 3

Neoepitopes (10-mer) with high binding affinity for HLA-A2402

| transcript | gene | chr | pos | ref | alt | expr (RPKM) | WT_AA | MT_AA | MTpep | | MT_ic50 | Score level |
|---|---|---|---|---|---|---|---|---|---|---|---|---|
| hg19_knownGene_uc002kft.3 | RAB40B | chr17 | 80616484 | C | T | 0 | AQAYAERLGVTFFEVSPLC | AQAYAERLGMTFFEVSPLC | SEQ ID NO: 31 | AYAERLGMTF | 19 | high |
| hg19_knownGene_uc010ppd.2, hg19_knownGene_uc009wza.3, hg19_knownGene_uc001gtz.3, hg19_knownGene_uc010ppb.2, hg19_knownGene_uc010poz.2, hg19_knownGene_uc001gub.1 | CRB1 | chr1 | 1.97E+08 | T | G | 0 | TSNGVALLNFYNMPSTPSF | TSNGVALLNVYNMPSTPSF | SEQ ID NO: 32 | VYNMPSTPSF | 38 | high |
| hg19_knownGene_uc003vsp.2 | WDR91 | chr7 | 1.35E+08 | C | T | 0 | LRDYWSYLERRLFSRLEDI | LRDYWSYLEHRLFSRLEDI | SEQ ID NO: 33 | YWSYLEHRLF | 40 | high |
| hg19_knownGene_uc002bxi.3, hg19_knownGene_uc002bxh.3, hg19_knownGene_uc002bxj.3 | TM2D3 | chr15 | 1.02E+08 | G | A | 0 | FSFGGLGIWTLIDVLLIGV | FSFGGLGIWMLIDVLLIGV | SEQ ID NO: 34 | IWMLIDVLLI | 47 | high |
| hg19_knownGene_uc003jml.2, hg19_knownGene_uc003jmk.3 | C6 | chr5 | 41149516 | T | G | 0 | NDYFTSPACKFLAEKCLNN | NDYFTSPACTFLAEKCLNN | SEQ ID NO: 35 | DYFTSPACTF | 60 | medium |

TABLE 3-continued

Neoepitopes (10-mer) with high binding affinity for HLA-A2402

| transcript | gene | chr | pos | ref | alt | expr (RPKM) | WT_AA | MT_AA | MTpep | MT_ic50 | Score level |
|---|---|---|---|---|---|---|---|---|---|---|---|
| hg19_knownGene_uc002jig.2, hg19_knownGene_uc002jid.2, hg19_knownGene_uc002jib.2, hg19_knownGene_uc002jic2, hg19_knownGene_uc002jif.2 | ABCA5 | chr17 | 67257696 | G | A | 0 | FWSFIYSVAALACIAITEI | FWSFIYSVAVLACIAITEI | SEQ ID NO: 36 | IYSVAVLACI | 64 | high |
| hg19_knownGene_uc003ahl.3, hg19_knownGene_uc021wnt.1 | SF3A1 | chr22 | 30730630 | C | T | 0 | LAYYNMANGAVIHLALKER | LAYYNMANGTVIHLALKER | SEQ ID NO: 37 | YYNMANGTVI | 80 | medium |
| hg19_knownGene_uc002baw.3 | CSPG4 | chr15 | 75974714 | G | A | 0 | PQLLLYRVVRGPQLGRLFH | PQLLLYRVVWGPQLGRLFH | SEQ ID NO: 38 | VWGPQLGRLF | 110 | high |
| hg19_knownGene_uc003suw.4, knownGene_uc010kuh.3 | ABCB5 | chr7 | 20782555 | G | A | 0 | REVSFFYPCRPDVFILRGL | REVSFFYPCHPDVFILRGL | SEQ ID NO: 39 | FYPCHPDVFI | 111 | high |
| hg19_knownGene_uc003fje.3, hg19_knownGene_uc031scj.1, hg19_knownGene_uc003fjd.3, hg19_knownGene_uc003fjf.3 | KCNMB2 | chr3 | 1.79E+08 | T | G | 0 | CSYIPKCGKNFEESMSLVN | CSYIPKCGKKFEESMSLVN | SEQ ID NO: 40 | SYIPKCGKKF | 133 | medium |
| hg19_knownGene_uc011eao.2, hg19_knownGene_uc003pss.4 | ARMC2 | chr6 | 1.09E+08 | G | T | 0 | IKKLVDCLRDLGPTDWQLA | IKKLVDCLRYLGPTDWQLA | SEQ ID NO: 41 | RYLGPTDWQL | 159 | high |
| hg19_knownGene_uc002ewg.1, hg19_knownGene_uc010cfg.1 | CDH1 | chr16 | 68844172 | G | T | 0 | PMEILITVTDQNDNKPEFT | PMEILITVTYQNDNKPEFT | SEQ ID NO: 42 | TYQNDNKPEF | 187 | high |
| hg19_knownGene_uc002dli.3 | HS3ST2 | chr16 | 22926539 | G | A | 0 | WNAIRIGMYVLHLESWLQY | WNAIRIGMYMLHLESWLQY | SEQ ID NO: 43 | MYMLHLESWL | 203 | high |
| hg19_knownGene_uc002xjc.3 | SLC32A1 | chr20 | 37357184 | G | A | 0 | LLWHQVFFDVAIFVIGGIC | LLWHQVFFDIAIFVIGGIC | SEQ ID NO: 44 | VFFDIAIFVI | 269 | high |

TABLE 3-continued

Neoepitopes (10-mer) with high binding affinity for HLA-A2402

| transcript | gene | chr | pos | ref | alt | expr (RPKM) | WT_AA | MT_AA | MTpep | | MT_ic50 | Score level |
|---|---|---|---|---|---|---|---|---|---|---|---|---|
| hg19_knownGene_uc001iwr.4, hg19_knownGene_uc001iwt.4, hg19_knownGene_uc001iws.4 | ITGB1 | chr10 | 33209310 | G | T | 0 | QLIIDAYNSLSSEVILENG | QLIIDAYNSISSEVILENG | SEQ ID NO: 45 | AYNSISSEVI | 274 | medium |
| hg19_knownGene_uc010zzf.1, hg19_knownGene_uc002xxt.2, hg19_knownGene_uc002xxu.2 | RTFDC1 | chr20 | 55059189 | G | A | 0 | HRFCFLRCCGCVFSERALK | HRFCFLRCCSCVFSERALK | SEQ ID NO: 46 | CFLRCCSCVF | 316 | high |
| hg19_knownGene_uc002wto.1 | CST4 | chr20 | 23669411 | G | A | 0 | KATEDEYYRRPLQVLRARE | KATEDEYYRCPLQVLRARE | SEQ ID NO: 47 | EYYRCPLQVL | 370 | medium |
| hg19_knownGene_uc001szy.4, hg19_knownGene_uc001szv.4 | SLC6A15 | chr12 | 85279797 | G | A | 0 | ILLMVIGIPLFFLELSVGQ | ILLMVIGIPFFFLELSVGQ | SEQ ID NO: 48 | LMVIGIPFFF | 404 | high |
| hg19_knownGene_uc003suw.4, hg19_knownGene_uc010kuh.3 | ABCB5 | chr7 | 20782555 | G | A | 0 | REVSFFYPCRPDVFILRGL | REVSFFYPCHPDVFILRGL | SEQ ID NO: 49 | FFYPCHPDVF | 436 | medium |

TABLE 4

Neoepitopes (8-mer) with high binding affinity for HLA-A0201

| transcript | gene | chr | pos | ref | alt | expr (RPKM) | WT_AA | MT_AA | MTpep | | MT_ic50 | Score level |
|---|---|---|---|---|---|---|---|---|---|---|---|---|
| hg19_knownGene_uc002bxi.3, hg19_knownGene_uc002bxh.3, hg19_knownGene_uc002bxj.3 | TM2D3 | chr15 | 1.02E+08 | G | A | 0 | FGGLGIWTLIDVLLI | FGGLGIWMLIDVLLI | SEQ ID NO: 50 | MLIDVLLI | 52 | high |
| hg19_knownGene_uc002kdu.3 | FASN | chr17 | 80049217 | G | A | 0 | LSMLNDIAAVPATAM | LSMLNDIVAVPATAM | SEQ ID NO: 51 | MLNDIVAV | 70 | high |
| hg19_knownGene_uc011mdo.2 | SARDH | chr9 | 1.37E+08 | G | A | 0 | MSLGKAYGVESHV | MSLGKVYGVESHV | SEQ ID NO: 52 | SLGKVYGV | 105 | high |

TABLE 4-continued

Neoepitopes (8-mer) with high binding affinity for HLA-A0201

| transcript | gene | chr | pos | ref | alt | expr (RPKM) | WT_AA | MT_AA | MTpep | MT_ic50 | Score level |
|---|---|---|---|---|---|---|---|---|---|---|---|
| hg19_knownGene_uc004cep.4, hg19_knownGene_uc004ceo.3, hg19_knownGene_uc011mdn.2 | SARDH | chr9 | 1.37E+08 | G | A | 0 | RLMSLGKAYGVESHV | RLMSLGKVYGVESHV | SEQ ID NO: 53 SLGKVYGV | 105 | high |
| hg19_knownGene_uc002pxe.4 | SIGLEC5 | chr19 | 52131128 | G | A | 0 | FTCRAQHPLGFLQIF | FTCRAQHLLGFLQIF | SEQ ID NO: 54 HLLGFLQI | 219 | high |
| hg19_knownGene_uc002lkw.3, hg19_knownGene_uc002lky.2 | NETO1 | chr18 | 70451000 | G | A | 0 | VANDVMLRTGLGVIR | VANDVMLCTGLGVIR | SEQ ID NO: 55 MLCTGLGV | 247 | high |
| hg19_knownGene_uc002bxi.3, hg19_knownGene_uc002bxh.3, hg19_knownGene_uc002bxj.3 | TM2D3 | chr15 | 1.02E+08 | G | A | 0 | FGGLGIWTLIDVLLI | FGGLGIWMLIDVLLI | SEQ ID NO: 56 GLGIWMLI | 329 | high |

TABLE 5

Neoepitopes (9-mer) with high binding affinity for HLA-A0201

| transcript | gene | chr | pos | ref | alt | expr (RPKM) | WT_AA | MT_AA | MTpep | MT_ic50 | Score level |
|---|---|---|---|---|---|---|---|---|---|---|---|
| hg19_knownGene_uc001bnm.4, hg19_knownGene_uc001bnn.3 | SLC9A1 | chr1 | 27436202 | C | T | 0 | VGIVDIFLGFLSFFVVA | VGIVDIFLSFLSFFVVA | SEQ ID NO: 57 FLSFLSFFV | 2 | high |
| hg19_knownGene_uc003bve.1 | IRAK2 | chr3 | 10264468 | C | T | 0 | AYLPEDFIRVGQLTKRV | AYLPEDFIWVGQLTKRV | SEQ ID NO: 58 YLPEDFIWV | 3 | high |
| hg19_knownGene_uc002kdu.3 | FASN | chr17 | 80049217 | G | A | 0 | FLSMLNDIAAVPATAMP | FLSMLNDIVAVPATAMP | SEQ ID NO: 59 SMLNDIVAV | 6 | high |
| hg19_knownGene_uc001aqh.3, hg19_knownGene_uc001aqi.3, hg19_knownGene_uc010oag.2 | CLSTN1 | chr1 | 9795564 | G | A | 0 | YLNSRQFPTPGIRRLKI | YLNSRQFPMPGIRRLKI | SEQ ID NO: 60 YLNSRQFPM | 7 | high |
| hg19_knownGene_uc002viv.3, hg19_knownGene_uc002viu.3 | STK36 | chr2 | 219558685 | G | A | 0 | YFLSLLVFRLQNLPCGM | YFLSLLVFQLQNLPCGM | SEQ ID NO: 61 FLSLLVFQL | 8 | high |

TABLE 5-continued

Neoepitopes (9-mer) with high binding affinity for HLA-A0201

| transcript | gene | chr | pos | ref | alt | expr (RPKM) | WT_AA | MT_AA | MTpep | MT_ic50 | Score level |
|---|---|---|---|---|---|---|---|---|---|---|---|
| hg19_knownGene_uc002dli.3 | HS3ST2 | chr16 | 22926539 | G | A | 0 | NAIRIGMYVLHLESWLQ | NAIRIGMYMLHLESWLQ | SEQ ID NO: 62 | YMLHLESWL | 8 | high |
| hg19_knownGene_uc011eao.2, hg19_knownGene_uc003pss.4 | ARMC2 | chr6 | 109286202 | G | T | 0 | KKLVDCLRDLGPTDWQL | KKLVDCLRDYLGPTDWQL | SEQ ID NO: 63 | KLVDCLRYL | 8 | high |
| 6hg19_knownGene_uc002pcc.4, hg19_knownGene_uc002pcb.4 | RTN2 | chr19 | 45997462 | G | A | 0 | VRGQCLDSTDQLEFTVE | VRGQCLDSMDQLEFTVE | SEQ ID NO: 64 | SMDQLEFTV | 9 | high |
| hg19_knownGene_uc002kft.3 | RAB40B | chr17 | 80616484 | C | T | 0 | QAYAERLGVTFFEVSPL | QAYAERLGMTFFEVSPL | SEQ ID NO: 65 | RLGMTFFEV | 13 | high |
| hg19_knownGene_uc011eao.2, hg19_knownGene_uc003pss.4 | ARMC2 | chr6 | 109286202 | G | T | 0 | KKLVDCLRDLGPTDWQL | KKLVDCLRDYLGPTDWQL | SEQ ID NO: 66 | YLGPTDWQL | 15 | high |
| hg19_knownGene_uc010dfa.1, hg19_knownGene_uc010dfb.1 | ABCA10 | chr17 | 67178331 | G | A | 0 | ALMGIFNFTELIQMEST | ALMGIFNFMELIQMEST | SEQ ID NO: 67 | ALMGIFNFM | 16 | high |
| hg19_knownGene_uc001cqs.3, hg19_knownGene_uc001cqr.3, hg19_knownGene_uc001cqt.3 | CYP4X1 | chr1 | 47512210 | C | T | 0 | TCRLIPAVPSISRDLSK | TCRLIPAVLSISRDLSK | SEQ ID NO: 68 | RLIPAVLSI | 16 | high |
| hg19_knownGene_uc003pue.3, hg19_knownGene_uc003puf.3 | SLC22A16 | chr6 | 110746270 | C | T | 0 | PQLFVGTMALLSGVLTL | PQLFVGTMTLLSGVLTL | SEQ ID NO: 69 | TLLSGVLTL | 20 | high |
| hg19_knownGene_uc002kdu.3 | FASN | chr17 | 80049217 | G | A | 0 | FLSMLNDIAAVPATAMP | FLSMLNDIVAVPATAMP | SEQ ID NO: 70 | FLSMLNDIV | 20 | high |
| hg19_knownGene_uc010joz.2, hg19_knownGene_uc031sms.1, hg19_knownGene_uc003mzv.2, hg19_knownGene_uc003mzw.3 | NEDD9 | chr6 | 11185718 | C | T | 0 | ISLLNAIDALFSCVSSA | ISLLNAIDTLFSCVSSA | SEQ ID NO: 71 | TLFSCVSSA | 21 | high |

US 11,969,463 B2

TABLE 5-continued

Neoepitopes (9-mer) with high binding affinity for HLA-A0201

| transcript | gene | chr | pos | ref | alt | expr (RPKM) | WT_AA | MT_AA | MTpep | MT_ic50 | Score level |
|---|---|---|---|---|---|---|---|---|---|---|---|
| hg19_knownGene_uc002lkw.3, hg19_knownGene_uc002lky.2 | NETO1 | chr18 | 70451000 | G | A | 0 | TVANDVMLRTGLGVIRM | TVANDVMLCTGLGVIRM | SEQ ID NO: 72 VMLCTGLGV | 26 | high |
| hg19_knownGene_uc010hiq.3, hg19_knownGene_uc003cnx.4 | KIF15 | chr3 | 44828026 | C | T | 0 | KKGVFVVGAVEQVVTSA | KKGVFVVGVVEQVVTSA | SEQ ID NO: 73 FVVGVVEQV | 29 | high |
| hg19_knownGene_uc002fjl.3 | FOXF1 | chr16 | 86545019 | G | A | 0 | ASAALNSGASYIKQQPL | ASAALNSGTSYIKQPL | SEQ ID NO: 74 ALNSGTSYI | 29 | high |
| hg19_knownGene_uc010joz.2, hg19_knownGene_uc031sms1, hg19_knownGene_uc003mzv.2, hg19_knownGene_uc003mzw.3 | NEDD9 | chr6 | 11185718 | C | T | 0 | ISLLNAIDALFSCVSSA | ISLLNAIDTLFSCVSSA | SEQ ID NO: 75 SLLNAIDTL | 30 | high |
| hg19_knownGene_uc001hzh.3, hg19_knownGene_uc021plk.1, hg19_knownGene_uc009xgq.3, hg19_knownGene_uc021plj.1 | EXO1 | chr1 | 242035442 | T | C | 0 | KSLSFSEVFVPDLVNGP | KSLSFSEVSVPDLVNGP | SEQ ID NO: 76 SLSFSEVSV | 32 | high |
| hg19_knownGene_uc003lmh4, hg19_knownGene_uc010jgh.3, hg19_knownGene_uc003lmf.4, hg19_knownGene_uc003lmg.4 | GNPDA1 | chr5 | 141384531 | G | A | 0 | TKVPTMALTVGVGTVMD | TKVPTMALMVGVGTVMD | SEQ ID NO: 77 ALMVGVGTV | 33 | high |
| hg19_knownGene_uc002jig.2, knownGene_uc002jid.2, hg19_knownGene_uc002jib.2, hg19_knownGene_uc002jic.2, hg19_knownGene_uc002jif.2 | ABCA5 | chr17 | 67257396 | G | A | 0 | WSFIYSVAALACIAITE | WSFIYSVAAVLACIAITE | SEQ ID NO: 78 FIYSVLA | 38 | high |

TABLE 5-continued

Neoepitopes (9-mer) with high binding affinity for HLA-A0201

| transcript | gene | chr | pos | ref | alt | expr (RPKM) | WT_AA | MT_AA | MTpep | | MT_ic50 | Score level |
|---|---|---|---|---|---|---|---|---|---|---|---|---|
| hg19_knownGene_uc002bxi.3, hg19_knownGene_uc002bxh.3, hg19_knownGene_uc002bxj.3 | TM2D3 | chr15 | 102182749 | G | A | 0 | SFGGLGIWTLIDVLLIG | SFGGLGIWMLIDVLLIG | SEQ ID NO: 79 | WMLIDVLLI | 41 | high |
| hg19_knownGene_uc001mmg.3, hg19_knownGene_uc001mme.3 | SOX6 | chr11 | 16077437 | G | A | 0 | HKQIEQLYAAQLASMQV | HKQIEQLYVAQLASMQV | SEQ ID NO: 80 | KQIEQLYVA | 45 | high |
| hg19_knownGene_uc022cbc.1, hg19_knownGene_uc004ejj.4, hg19_knownGene_uc022cbd.1, hg19_knownGene_uc004eji.4, hg19_knownGene_uc010nod.3 | GPRASP1 | chrX | 101912464 | C | T | 0 | LIETLLNYPSSRVRTSF | LIETLLNYLSSRVRTSF | SEQ ID NO: 81 | LLNYLSSRV | 47 | high |
| hg19_knownGene_uc003pue.3, hg19_knownGene_uc003puf.3 | SLC22A16 | chr16 | 110746270 | C | T | 0 | PQLFVGTMALLSGVLTL | PQLFVGTMTLLSGVLTL | SEQ ID NO: 82 | GTMTLLSGV | 50 | high |
| hg19_knownGene_uc011dzr.2, hg19_knownGene_uc011dzt.2, hg19_knownGene_uc010kbz.3, hg19_knownGene_uc010kca.3, hg19_knownGene_uc003pmq.4, hg19_knownGene_uc011dzs.2, hg19_knownGene_uc021zco.1 | CNR1 | chr6 | 88853864 | G | A | 0 | GKMNKLIKTVFAFCSML | GKMNKLIKMVFAFCSML | SEQ ID NO: 83 | MVFAFCSML | 50 | high |
| hg19_knownGene_uc011kis.2, hg19_knownGene_uc003upp.3, hg19_knownGene_uc003upr.3 | TRRAP | chr7 | 98519385 | C | T | 0 | AELMQALWRTLRNPADS | AELMQALWCTLRNPADS | SEQ ID NO: 84 | LMQALWCTL | 53 | high |

TABLE 5-continued

Neoepitopes (9-mer) with high binding affinity for HLA-A0201

| transcript | gene | chr | pos | ref | alt | expr (RPKM) | WT_AA | MT_AA | MTpep | MT_ic50 | Score level |
|---|---|---|---|---|---|---|---|---|---|---|---|
| hg19_knownGene_uc011mdo.2 | SARDH | chr9 | 136596596 | G | A | 0 | MSLGKAYGVESHVL | MSLGKVYGVESHVL | SEQ ID NO: 85 MSLGKVYGV | 54 | high |
| hg19_knownGene_uc004cep.4, hg19_knownGene_uc004ceo.3, hg19_knownGene_uc011mdn.2 | SARDH | chr9 | 136596596 | G | A | 0 | KRLMSLGKAYGVESHVL | KRLMSLGKVYGVESHVL | SEQ ID NO: 86 MSLGKVYGV | 54 | high |
| hg19_knownGene_uc002pxe.4 | SIGLEC5 | chr19 | 52131128 | G | A | 0 | GFTCRAQHPLGFLQIFL | GFTCRAQHLLGFLQIFL | SEQ ID NO: 87 LLGFLQIFL | 55 | high |
| hg19_knownGene_uc002hue.3, hg19_knownGene_uc010cwt.1 | CASC3 | chr17 | 38324513 | C | T | 0 | PNPGLYPPPVSMSPGQP | PNPGLYPPLVSMSPGQP | SEQ ID NO: 88 GLYPPLVSM | 60 | high |
| hg19_knownGene_uc002kft.3 | RAB40B | chr17 | 80616484 | C | T | 0 | QAYAERLGVTFFEVSPL | QAYAERLGMTFFEVSPL | SEQ ID NO: 89 MTFFEVSPL | 66 | high |
| hg19_knownGene_uc002xwa.4, hg19_knownGene_uc002xwb.3 | KCNG1 | chr20 | 49626482 | G | A | 0 | FGTILTFLRAGKLRLLR | FGTILTFLCAGKLRLLR | SEQ ID NO: 90 FLCAGKLRL | 73 | high |
| hg19_knownGene_uc011dzr.2, hg19_knownGene_uc011dzt.2, hg19_knownGene_uc010kbz.3, hg19_knownGene_uc010kca.3, hg19_knownGene_uc003pmq.4, hg19_knownGene_uc011dzs.2, hg19_knownGene_uc021zco.1 | CNR1 | chr6 | 88853864 | G | A | 0 | GKMNKLIKTVFAFCSML | GKMNKLIKMVFAFCSML | SEQ ID NO: 91 KMNKLIKMV | 79 | medium |
| hg19_knownGene_uc003pue.3, hg19_knownGene_uc003puf.3 | SLC22A16 | chr6 | 110746270 | C | T | 0 | PQLFVGTMALLSGVLTL | PQLFVGTMTLLSGVLTL | SEQ ID NO: 92 QLFVGTMTL | 84 | high |
| hg19_knownGene_uc003fjk.3 | PIK3CA | chr3 | 178916891 | G | A | 0 | ETTRLCDLRLFQPFLKV | ETRRLCDLQLFQPFLKV | SEQ ID NO: 93 QLFQPFLKV | 84 | high |

TABLE 5-continued

Neoepitopes (9-mer) with high binding affinity for HLA-A0201

| transcript | gene | chr | pos | ref | alt | expr (RPKM) | WT_AA | MT_AA | MTpep | MT_ic50 | Score level |
|---|---|---|---|---|---|---|---|---|---|---|---|
| hg19_knownGene_uc002hue.3, hg19_knownGene_uc010cwt.1 | CASC3 | chr17 | 38324639 | C | T | 0 | YAPGLPPPPPPHLYPN | YAPGALPPLPPPHLYPN | SEQ ID NO: 94 | YAPGALPPL | 93 | high |
| hg19_knownGene_uc011bai.2, hg19_knownGene_uc011baj.2 | SLC6A20 | chr3 | 45817323 | G | A | 0 | NGGVQWEPALCLLLAWL | NGGVQWEPVLCLLLAWL | SEQ ID NO: 95 | VQWEPVL | 95 | high |
| hg19_knownGene_uc010dfa.1, hg19_knownGene_uc010dfb.1 | ABCA10 | chr17 | 67178331 | G | A | 0 | ALMGIFNFTELIQMEST | ALMGIFNFMELIQMEST | SEQ ID NO: 96 | GIFNFMELI | 105 | high |
| hg19_knownGene_uc001qsy.3, hg19_knownGene_uc010sge.2 | CD163L1 | chr12 | 7531888 | G | A | 0 | VGVICSDASDMELRLVG | VGVICSDALDMELRLVG | SEQ ID NO: 97 | ALDMELRLV | 120 | high |
| hg19_knownGene_uc001vow.1, hg19_knownGene_uc001vov.1 | TMTC4 | chr13 | 101277794 | G | A | 0 | PDCYYNLGPLVSAGCPV | PDCYYNLGCLVSAGCPV | SEQ ID NO: 98 | CLVSAGCPV | 122 | high |
| hg19_knownGene_uc004agr.3 | PGM5 | chr9 | 70993145 | A | G | 0 | RLIIGQNGILSTPAVSC | RLIIGQNGVLSTPAVSC | SEQ ID NO: 99 | RLIIGQNGV | 124 | high |
| hg19_knownGene_uc001vpa.2, hg19_knownGene_uc001voz.2, hg19_knownGene_uc001vox.1 | NALCN | chr13 | 102029355 | C | T | 0 | QMSPWGMLRIPRPLIMI | QMSPWGMLQIPRPLIMI | SEQ ID NO: 100 | GMLQIPRPL | 134 | medium |
| hg19_knownGene_uc001tml.1, hg19_knownGene_uc001tmk.1, hg19_knownGene_uc001tmj.3, hg19_knownGene_uc009zut.1 | BTBD11 | chr12 | 108004005 | C | T | 0 | FCASRKLDAVAIEAKFK | FCASRKLDVVAIEAKFK | SEQ ID NO: 101 | KLDVVAIEA | 148 | high |
| hg19_knownGene_uc011mdo.2 | SARDH | chr9 | 136596596 | G | A | 0 | MSLGKAYGVESHVESHVL | MSLGKVYGVESHVESHVL | SEQ ID NO: 102 | KVYGVESHV | 148 | high |

TABLE 5-continued

Neoepitopes (9-mer) with high binding affinity for HLA-A0201

| transcript | gene | chr | pos | ref | alt | expr (RPKM) | WT_AA | MT_AA | MTpep | MT_ic50 | Score level |
|---|---|---|---|---|---|---|---|---|---|---|---|
| hg19_knownGene_uc004cep.4, hg19_knownGene_uc004ceo.3, hg19_knownGene_uc011mdn.2 | SARDH | chr9 | 136596596 | G | A | 0 | KRLMSLGKAYGVESHVL | KRLMSLGKVYGVESHVL | SEQ ID NO: 103 | KVYGVESHV | 148 | high |
| hg19_knownGene_uc003qtl.3 | LPA | chr6 | 161006078 | G | A | 0 | RIPLYYPNAGLTRNYCR | RIPLYYPNVGLTRNYCR | SEQ ID NO: 104 | RIPLYYPNV | 153 | high |
| hg19_knownGene_uc001iwr.4, hg19_knownGene_uc001iwt.4, hg19_knownGene_uc001iws.4 | ITGB1 | chr10 | 33209310 | G | T | 0 | LIIDAYNSLSSEVILEN | LIIDAYNSISSEVILEN | SEQ ID NO: 105 | LIIDAYNSI | 164 | medium |
| hg19_knownGene_uc003eki.3 | EEFSEC | chr3 | 127965789 | G | A | 0 | QIACQKLVVVLNKIDLL | QIACQKLVMVLNKIDLL | SEQ ID NO: 106 | MVLNKIDLL | 170 | high |
| hg19_knownGene_uc002viv.3, hg19_knownGene_uc002viu.3 | STK36 | chr2 | 219558685 | G | A | 0 | YFLSLLVFRLQNLPCGM | YFLSLLVFQLQNLPCGM | SEQ ID NO: 107 | LLVFQLQNL | 172 | high |
| hg19_knownGene_uc011bai.2, hg19_knownGene_uc011baj.2 | SLC6A20 | chr3 | 45817323 | G | A | 0 | NGGVQWEPALCLLLAWL | NGGVQWEPVLCLLLAWL | SEQ ID NO: 108 | VLCLLLAWL | 173 | high |
| hg19_knownGene_uc003jml.2, hg19_knownGene_uc003jmk.3 | C6 | chr5 | 41149516 | T | G | 0 | DYFTSPACKFLAEKCLN | DYFTSPACTFLAEKCLN | SEQ ID NO: 109 | FTSPACTFL | 212 | high |
| hg19_knownGene_uc003eki3 | EEFSEC | chr3 | 127965789 | G | A | 0 | QIACQKLVVVLNKIDLL | QIACQKLVMVLNKIDLL | SEQ ID NO: 110 | KLVMVLNKI | 214 | medium |
| hg19_knownGene_uc002xjc.3 | SLC32A1 | chr20 | 37357184 | G | A | 0 | LWHQVFFDVAIFVIGGI | LWHQVFFDIAIFVIGGI | SEQ ID NO: 111 | VFFDIAIFV | 225 | high |
| hg19_knownGene_uc003xed.4, hg19_knownGene_uc011lac.1 | NEFM | chr8 | 24771944 | C | T | 0 | ALRKDIEEASLVKVELD | ALRKDIEEVSLVKVELD | SEQ ID NO: 112 | ALRKDIEEV | 256 | high |

TABLE 5-continued

Neoepitopes (9-mer) with high binding affinity for HLA-A0201

| transcript | gene | chr | pos | ref | alt | expr (RPKM) | WT_AA | MT_AA | MTpep | | MT_ic50 | Score level |
|---|---|---|---|---|---|---|---|---|---|---|---|---|
| hg19_knownGene_uc001hyf.2, hg19_knownGene_uc001hyg.2, hg19_knownGene_uc009xgi.1 | ACTN2 | chr1 | 236902618 | G | A | 0 | ASELLEWIRRTIPWLEN | ASELLEWIHRTIPWLEN | SEQ ID NO: 113 | ELLEWIHRT | 262 | medium |
| hg19_knownGene_uc010joz.2, hg19_knownGene_uc031sms1, hg19_knownGene_uc003mzv.2, hg19_knownGene_uc003mzw.3 | NEDD9 | chr6 | 11185718 | C | T | 0 | ISLLNAIDALFSCVSSA | ISLLNAIDTLFSCVSSA | SEQ ID NO: 114 | AIDTLFSCV | 272 | medium |
| hg19_knownGene_uc003thb.2, hg19_knownGene_c022acb.1 | POU6F2 | chr7 | 39503921 | C | T | 0 | KLDITPKSAQKIKPVLE | KLDITPKSVQKIKPVLE | SEQ ID NO: 115 | KLDITPKSV | 274 | medium |
| hg19_knownGene_uc001bnm.4, hg19_knownGene_uc001bnn.3 | SLC9A1 | chr1 | 27436202 | C | T | 0 | VGIVDIFLGFLSFFVVA | VGIVDIFLSFLSFFVVA | SEQ ID NO: 116 | IVDIFLSFL | 284 | high |
| hg19_knownGene_uc002hbi.3, hg19_knownGene_uc002hbh.3, hg19_knownGene_uc010wal.1, hg19_knownGene_uc010wam.2 hg19_knownGene_uc010wan.2 | SLC13A2 | chr17 | 26817568 | G | A | 0 | HWNLHKRIALRVLLIVG | HWNLHKRITLRVLLIVG | SEQ ID NO: 117 | ITLRVLLIV | 304 | high |
| hg19_knownGene_uc011dzr.2, hg19_knownGene_uc011dzt.2, hg19_knownGene_uc010kbz.3, hg19_knownGene_uc010kca.3, hg19_knownGene_uc003pmq.4, hg19_knownGene_uc011dzs.2, hg19_knownGene_uc021zco.1 | CNR1 | chr6 | 88853864 | G | A | 0 | GKMNKLIKTVFAFCSML | GKMNKLIKMVFAFCSML | SEQ ID NO: 118 | KLIKMVFAF | 312 | medium |

TABLE 5-continued

Neoepitopes (9-mer) with high binding affinity for HLA-A0201

| transcript | gene | chr | pos | ref | alt | expr (RPKM) | WT_AA | MT_AA | MTpep | | MT_ic50 | Score level |
|---|---|---|---|---|---|---|---|---|---|---|---|---|
| hg19_knownGene_uc011dzr.2, hg19_knownGene_uc011dzt.2, hg19_knownGene_uc010kbz.3, hg19_knownGene_uc010kca.3, hg19_knownGene_uc003pmq.4, hg19_knownGene_uc011dzs.2, hg19_knownGene_uc021zco.1 | CNR1 | chr6 | 88853864 | G | A | 0 | GKMNKLIKTVFAFCSML | GKMNKLIKMNFAFCSML | SEQ ID NO: 119 | KMVFAFCSM | 313 | high |
| hg19_knownGene_vkp.1, hg19_knownGene_uc001vkq.1, hg19_knownGene_uc001vko.2, hg19_knownGene_uc010aez.1 | EDNRB | chr13 | 78492668 | G | A | 0 | SLCGRALVALVLACGLS | SLCGRALVVLVLACGLS | SEQ ID NO: 120 | SLCGRALVV | 325 | high |
| hg19_knownGene_uc002bxi.3, hg19_knownGene_uc002bxh.3, hg19_knownGene_uc002bxj.3 | TM2D3 | chr15 | 102182749 | G | A | 0 | SFGGLGIWTLIDVLLIG | SFGGLGIWMLIDVLLIG | SEQ ID NO: 121 | MLIDVLLIG | 343 | medium |

TABLE 6

Neoepitopes (10-mer) with high binding affinity for HLA-A0201

| transcript | gene | chr | pos | ref | alt | expr (RPKM) | WT_AA | MT_AA | MTpep | | MT_ic50 | Score level |
|---|---|---|---|---|---|---|---|---|---|---|---|---|
| hg19_knownGene_uc002bxi.3, hg19_knownGene_uc002bxh.3, hg19_knownGene_uc002bxj.3 | TM2D3 | chr15 | 102182749 | G | A | 0 | FSFGGLGIWTLIDVLLIGV | FSFGGLGIWMLIDVLLIGV | SEQ ID NO: 122 | MLIDVLLIGV | 4 | high |
| hg19_knownGene_uc003pkl.2 | TBX18 | chr6 | 85446536 | G | A | 0 | LGSSPSGTMTDRQMLPPVE | LGSSPSGTMMDRQMLPPVE | SEQ ID NO: 123 | MMDRQMLPPV | 6 | high |

TABLE 6-continued

Neoepitopes (10-mer) with high binding affinity for HLA-A0201

| transcript | gene | chr | pos | ref | alt | expr (RPKM) | WT_AA | MT_AA | MTpep | MT_ic50 | Score level |
|---|---|---|---|---|---|---|---|---|---|---|---|
| hg19_knownGene_uc001bnm.4, hg19_knownGene_uc001bnn.3 | SLC9A1 | chr1 | 27436202 | C | T | 0 | HVGIVDIFLGFLSFFVVAL | HVGIVDIFLSFLSFFVVAL | SEQ ID NO: 124 | FLSFLSFFVV | 6 | high |
| hg19_knownGene_uc022cbc.1, hg19_knownGene_uc004ejj.4, hg19_knownGene_uc022cbd.1, hg19_knownGene_uc004eji.4, hg19_knownGene_uc010nod.3 | GPRASP1 | chrX | 101912464 | C | T | 0 | SLIETLLNYPSSRVRTSFL | SLIETLLNYLSSRVRTSFL | SEQ ID NO: 125 | SLIETLLNYL | 10 | high |
| hg19_knownGene_uc010bid.2, hg19_knownGene_uc002arr.2, hg19_knownGene_uc002ars.2, hg19_knownGene_uc002arq.2, hg19_knownGene_uc010bie.2, hg19_knownGene_uc002arp.2 | NOX5 | chr15 | 69329504 | G | A | 0 | EKAIGLAVSRMAAVCIMEV | EKAIGLAVSHMAAVCIMEV | SEQ ID NO: 126 | HMAAVCIMEV | 13 | high |
| hg19_knownGene_uc022cbc.1, hg19_knownGene_uc004ejj.4, hg19_knownGene_uc022cbd.1, hg19_knownGene_uc004eji.4, hg19_knownGene_uc010nod.3 | GPRASP1 | chrX | 101912464 | C | T | 0 | SLIETLLNYPSSRVRTSFL | SLIETLLNYLSSRVRTSFL | SEQ ID NO: 127 | TLLNYLSSRV | 16 | high |
| hg19_knownGene_uc002pxe.4 | SIGLEC5 | chr19 | 52131128 | G | A | 0 | GGFTCRAQHPLGFLQIFLN | GGFTCRAQHLLGFLQIFLN | SEQ ID NO: 128 | HLLGFLQIFL | 19 | high high |
| hg19_knownGene_uc001tml.1, hg19_knownGene_uc001tmk.1, hg19_knownGene_uc0014tmm.1 | BTBD11 | chr12 | 108045467 | A | C | 0 | EIMELLSAAKFFQLEALQR | EIMELLSAATFFQLEFFQLEALQR | SEQ ID NO: 129 | LLSAATFFQL | 22 | high |

TABLE 6-continued

Neoepitopes (10-mer) with high binding affinity for HLA-A0201

| transcript | gene | chr | pos | ref | alt | expr (RPKM) | WT_AA | MT_AA | MTpep | MT_ic50 | Score level |
|---|---|---|---|---|---|---|---|---|---|---|---|
| hg19_knownGene_uc004cep.4, hg19_knownGene_uc004ceo.3, hg19_knownGene_uc011mdn.2 | SARDH | chr9 | 136596596 | G | A | 0 | YKRLMSLGKAYGVESHVLS | YKRLMSLGKVYGVESHVLS | SEQ ID NO: 130 | LMSLGKVYGV | 22 | high |
| hg19_knownGene_uc001szy.4, hg19_knownGene_uc001szv.4 | SLC6A15 | chr12 | 85279797 | G | A | 0 | ILLMVIGILFFLELSVGQ | ILLMVIGIPFFFLELSVGQ | SEQ ID NO: 131 | MVIGIPFFFL | 28 | high |
| hg19_knownGene_uc010sul.3 | SLC6A15 | chr12 | 85279797 | G | A | 0 | MVIGIPLFFLELSVGQ | MVIGIPFFFLELSVGQ | SEQ ID NO: 132 | MVIGIPFFFL | 28 | high |
| hg19_knownGene_uc003xrh.1, hg19_knownGene_uc022aup.1, hg19_knownGene_uc010lyc.1, hg19_knownGene_uc003xri.1 | OPRK1 | chr8 | 54142147 | C | T | 0 | VLVVVAVFVVCWTPIHIFI | VLVVVAVFVICWTPIHIFI | SEQ ID NO: 133 | FVICWTPIHI | 33 | high |
| hg19_knownGene_uc002kdu.3 | FASN | chr17 | 80049217 | G | A | 0 | AFLSMLNDIAAVPATAMPF | AFLSMLNDIVAVPATAMPF | SEQ ID NO: 134 | MLNDIVAVPA | 35 | high |
| hg19_knownGene_uc002xjc.3 | SLC32A1 | chr20 | 37357184 | G | A | 0 | LLWHQVFFDVAIFVIGGIC | LLWHQVFFDIAIFVIGGIC | SEQ ID NO: 135 | LLWHQVFFDI | 35 | high |
| hg19_knownGene_uc003jqw.4 | MAP3K1 | chr5 | 56181765 | C | T | 0 | LFIEWMAGGSVAHLLSKYG | LFIEWMAGGLVAHLLSKYG | SEQ ID NO: 136 | WMAGGLVAHL | 37 | high |
| hg19_knownGene_uc010vlm.2, hg19_knwonGene_uc002exu.2, hg19_knownGene_uc031qwu.1, hg19_knownGene_uc002exv.2 | WWP2 | chr16 | 69942692 | C | T | 0 | WEQRELPNGRVYYVDHNTK | WEQRELPNGCVYYVDHNTK | SEQ ID NO: 137 | ELPNGCVYYV | 38 | high |
| hg19_knownGene_uc002hhp.1, hg19_knownGene_uc002hho.1, hg19_knownGene_uc010wcb.2 | MYO1D | chr17 | 31087632 | C | T | 0 | DAFAKAIYERLFCWIVTRI | DAFAKAIYEHLFCWIVTRI | SEQ ID NO: 138 | HLFCWIVTRI | 39 | high |

TABLE 6-continued

Neoepitopes (10-mer) with high binding affinity for HLA-A0201

| transcript | gene | chr | pos | ref | alt | expr (RPKM) | WT_AA | MT_AA | MTpep | MT_ic50 | Score level |
|---|---|---|---|---|---|---|---|---|---|---|---|
| hg19_knownGene_uc011bai.2, hg19_knownGene_uc011baj.2 | SLC6A20 | chr3 | 45817323 | G | A | 0 | ENGGVQWEPALCLLLAWLV | ENGGVQWEPVLCLLLAWLV | SEQ ID NO: 139 VNCLLLAWLV | 40 | high |
| hg19_knownGene_uc001szj.1 | LIN7A | chr12 | 81283099 | T | G | 0 | LLEKLQESGEVPVHKLQSL | LLEKLQESGDVPVHKLQSL | SEQ ID NO: 140 KLQESGDVPV | 41 | medium |
| hg19_knownGene_uc010rxb.2, hg19_knownGene_uc010rxa.2, hg19_knownGene_uc010rxc.2 | HTR3A | chr11 | 113853876 | G | A | 0 | VGKSPNIPYVYIRHQGEVQ | VGKSPNIPYMYIRHQGEVQ | SEQ ID NO: 141 YMYIRHQGEV | 42 | high |
| hg19_knownGene_uc002hue.3, hg19_knownGene_uc010cwt.1 | CASC3 | ch217 | 38325584 | C | T | 0 | HLYPNTQAPSQVYGGVTYY | HLYPNTQAPLQVYGGVTYY | SEQ ID NO: 142 HLYPNTQAPL | 45 | high |
| hg19_knownGene_uc003sys.3 | HOXA7 | chr7 | 27194754 | G | A | 0 | KEHFNRYLTRRRIEIAH | KEHFNRYLMRRRRIEIAH | SEQ ID NO: 143 YLMRRRRIEI | 48 | high |
| hg19_knownGene_uc002viv.3, hg19_knownGene_uc002viu.3 | STK36 | chr2 | 219558685 | G | A | 0 | LYFLSLLVFRLQNLPCGME | LYFLSLLVFQLQNLPCGME | SEQ ID NO: 144 SLLVFQLQNL | 48 | high |
| hg19_knownGene_uc010dfa.1, hg19_knownGene_uc010dfb.1 | ABCA10 | chr17 | 67178331 | G | A | 0 | NALMGIFNFTELIQMESTS | NALMGIFNFMELIQMESTS | SEQ ID NO: 145 LMGIFNFMEL | 56 | high |
| hg19_knownGene_uc002xwa.4, hg19_known_Gene_uc002xwb.3 | KCNG1 | chr20 | 49626482 | G | A | 0 | AFGTILTFLRAGKLRLLRE | AFGTILTFLCAGKLRLLRE | SEQ ID NO: 146 FLCAGKLRLL | 60 | high |
| hg19_knownGene_uc002bxi3, hg19_knownGene_uc002bxh.3, hg19_knownGene_uc002bxj.3 | TM2D3 | chr15 | 10282749 | G | A | 0 | FSFGGLGIWTLIDVLLIGV | FSFGGLGIWMLIDVLLIGV | SEQ ID NO: 147 GLGIWMLIDV | 62 | high |

TABLE 6-continued

Neoepitopes (10-mer) with high binding affinity for HLA-A0201

| transcript | gene | chr | pos | ref | alt | expr (RPKM) | WT_AA | MT_AA | MTpep | MT_ic50 | Score level |
|---|---|---|---|---|---|---|---|---|---|---|---|
| hg19_knownGene_uc002qwx.3, hg19_knownGene_uc002qww.3, hg19_knownGene_uc010yio.2, hg19_knownGene_uc002qwr.3, hg19_knownGene_uc002qwu.3, hg19_knownGene_uc010yip.2 | TPO | chr2 | 1497732 | T | C | 0 | VWLGGLAENFLPRARTGPL | VWLGGLAENLLPRARTGPL | SEQ ID NO: 148 GLAENLLPRA | 65 | high |
| hg19_knownGene_uc001bnm.4, hg19_knownGene_uc001bnn.3 | SLC9A1 | chr1 | 27436202 | C | T | 0 | HVGIVDIFLGFLSFFVVAL | HVGIVDIFLSFLSFFVVAL | SEQ ID NO: 149 IFLSFLSFFV | 67 | high |
| hg19_knownGene_uc002jig.2, hg19_knownGene_uc002jid.2, hg19_knownGene_uc002jib.2, hg19_knownGene_uc002jic.2, hg19_knownGene_uc002jif.2 | ABCA5 | chr17 | 67257396 | G | A | 0 | FWSFIYSVAALACIAITEI | FWSFIYSVAVACIAITEI | SEQ ID NO: 150 VLACIAITEI | 68 | high |
| hg19_knownGene_uc001vot.3, hg19_knownGene_uc010tja.2, hg19_knownGene_uc001vou.3 | TMTC4 | chr13 | 101277794 | G | A | 0 | YPDCYYNLGRLYADLNRHV | YPDCYYNLGCLYADLNRHV | SEQ ID NO: 151 CLYADLNRHV | 68 | high |
| hg19_knownGene_uc002kdu.3 | FASN | chr17 | 80049217 | G | A | 0 | AFLSMLNDIAAVPATAMPF | AFLSMLNDIVAVPATAMPF | SEQ ID NO: 152 FLSMLNDIVA | 71 | high |
| hg19_knownGene_uc003ah1.3, hg19_knownGene_uc021wnt.1 | SF3A1 | chr22 | 30730630 | C | T | 0 | LAYYNMANGAVIHLALKER | LAYYNMANGTVIHLALKER | SEQ ID NO: 153 NMANGTVIHL | 76 | high |

TABLE 6-continued

Neoepitopes (10-mer) with high binding affinity for HLA-A0201

| transcript | gene | chr | pos | ref | alt | expr (RPKM) | WT_AA | MT_AA | MTpep | MT_ic50 | Score level |
|---|---|---|---|---|---|---|---|---|---|---|---|
| hg19_knownGene_uc010bid.2, hg19_knownGene_uc002arr.2, hg19_knownGene_uc002ars.2, hg19_knownGene_uc002arq.2, hg19_knownGene_uc010bie.2, hg19_knownGene_uc002arp.2 | NOX5 | chr15 | 69329504 | G | A | 0 | EKAIGLAVSRMAAVCIMEV | EKAIGLAVSHMAAVCIMEV | SEQ ID NO: 154 | GLAVSHMAAV | 77 | high |
| hg19_knownGene_uc001ouu.2 | C2CD3 | chr11 | 73811600 | A | C | 0 | QDKLLGLVKLPLHQFYMSF | QDKLLGLVKRPLHQFYMSF | SEQ ID NO: 155 | KLLGLVKRPL | 86 | high |
| hg19_knownGene_uc002xjc.3 | SLC32A1 | chr20 | 37357184 | G | A | 0 | LLWHQVFFDVAIFVIGGIC | LLWHQVFFDIAIFVIGGIC | SEQ ID NO: 156 | QVFFDIAIFV | 87 | high |
| hg19_knownGene_uc021qya.1, hg19_knownGene_uc001rzn.3, hg19_knownGene_uc010snn.2, hg19_knownGene_uc001rzm.3, hg19_knownGene_uc001rzl.3 | ACVR1B | chr12 | 52374774 | G | A | 0 | GSGLPLFVQRTVARTIVLQ | GSGLPLFVQHTVARTIVLQ | SEQ ID NO: 157 | GLPLFVQHTV | 89 | high |
| hg19_knownGene_uc001qsr.3, hg19_knownGene_uc001qss.3 | CLSTN3 | chr12 | 7288865 | G | A | 0 | GSLALFPGIRLETCDEPLW | GSLALFPGIHLETCDEPLW | SEQ ID NO: 158 | ALFPGIHLET | 89 | high |
| hg19_knownGene_uc003ysr.3 | GSDMC | chr8 | 130789814 | C | T | 0 | MPSMLERISKNLVKEI | MPSMLEHISKNLVKEI | SEQ ID NO: 159 | SMLEHISKNL | 89 | high |
| hg19_knownGene_uc003pue.3, hg19_knownGene_uc003.puf.3 | SLC22A16 | chr6 | 110746270 | C | T | 0 | IPQLFVGTMALLSGVLTLK | IPQLFVGTMTLLSGVLTLK | SEQ ID NO: 160 | QLFVGTMTLL | 95 | high |
| hg19_knownGene_uc0021gk.1, hg19_knownGene_uc0021gl.1 | WDR7 | chr18 | 54603098 | G | A | 0 | RHALSLIATARPPAFITTI | RHALSLIATRPPAFITTI | SEQ ID NO: 161 | SLIATTRPPA | 97 | medium |

TABLE 6-continued

Neoepitopes (10-mer) with high binding affinity for HLA-A0201

| transcript | gene | chr | pos | ref | alt | expr (RPKM) | WT_AA | MT_AA | MTpep | | MT_ic50 | Score level |
|---|---|---|---|---|---|---|---|---|---|---|---|---|
| hg19_knownGene_uc001fsd.3, hg19_knownGene_uc010pid.2, hg19_knownGene_uc001fsf.3, hg19_knownGene_uc001frz.3, hg19_knownGene_uc001fsj.3 hg19_knownGene_uc001fse.3, hg19_knownGene_uc001fsk.3, hg19_knownGene_uc001fry.3 | CD1E | chr1 | 158324361 | T | G | 0 | FLKPWSHGNFSKQELKNLQ | FLKPWSHGNVSKQELKNLQ | SEQ ID NO: 162 | FLKPWSHGNV | 98 | high |
| hg19_knownGene_uc002ehx.3, hg19_knownGene_uc002ehy.3 | IRX6 | chr16 | 55363164 | C | T | 0 | ALQGLPLNCAPCPRRSEPV | ALQGLPLNCVPCPRRSEPV | SEQ ID NO: 163 | ALQGLPLNCV | 98 | high |
| hg19_knownGene_uc001lcl.4 | PNLIPRP3 | chr10 | 118236283 | A | C | 0 | KHLFEDSQNKLGAEMVINT | KHLFEDSQNTLGAEMVINT | SEQ ID NO: 164 | HLFEDSQNTL | 99 | high |
| hg19_knownGene_uc010wek.2 | ERBB2 | chr17 | 37868208 | C | T | 0 | DNYLSTDVGSCTLVCPLHN | DNYLSTDVGFCTLVCPLHN | SEQ ID NO: 165 | YLSTDVGFCT | 106 | high |
| hg19_knownGene_uc002hso.3, hg19_knownGene_uc010cwa.3, hg19_knownGene_uc002hsl.3, hg19_knownGene_uc002hsn.1, hg19_knownGene_uc002hsp.3, hg19_knownGene_uc010cwb.3, hg19_knownGene_uc002hsm.3 | ERBB2 | chr17 | 37868208 | C | T | 0 | YNYLSTDVGSCTLVCPLHN | YNYLSTDVGFCTLVCPLHN | SEQ ID NO: 166 | YLSTDVGFCT | 106 | high |

TABLE 6-continued

Neoepitopes (10-mer) with high binding affinity for HLA-A0201

| transcript | gene | chr | pos | ref | alt | expr (RPKM) | WT_AA | MT_AA | MTpep | | MT_ic50 | Score level |
|---|---|---|---|---|---|---|---|---|---|---|---|---|
| hg19_knownGene_uc002emk.3, hg19_knownGene_uc002emi.3, hg19_knownGene_uc002emj.3 | CCDC135 | chr16 | 57760055 | G | A | 0 | DVAERVFLVAEERIQLRYH | DVAERVFLVTEERIQLRYH | SEQ ID NO: 167 | FLVTEERIQL | 107 | high |
| hg19_knownGene_uc002kft.3 | RAB40B | chr17 | 80616484 | C | T | 0 | AQAYAERLGVTFFEVSLPC | AQAYAERLGMTFFEVSPLC | SEQ ID NO: 168 | GMTFFEVSPL | 108 | high |
| hg19_knownGene_uc001qsr.3, hg19_knownGene_uc001qss.3 | CLSTN3 | chr12 | 7288865 | G | A | 0 | GSLALFPGIRLETCDEPLW | GSLALFPGIHLETCDEPLW | SEQ ID NO: 169 | SLALFPGIHL | 111 | high |
| hg19_knownGene_uc001mmd3, hg19_knownGene_uc001mmf.3 | SOX6 | chr11 | 16077437 | G | A | 0 | SPLQLQQLYAAQLASMQVS | SPLQLQQLYVAQLASMQVS | SEQ ID NO: 170 | YVAQLASMQV | 115 | high |
| hg19_knownGene_uc001mmg.3, hg19_knownGene_uc001mme.3 | SOX6 | chr11 | 16077437 | G | A | 0 | NHKQIEQLYAAQLASMQVS | NHKQIEQLYVAQLASMQVS | SEQ ID NO: 171 | YVAQLASMQV | 115 | high |
| hg19_knownGene_uc002hhp.1, hg19_knownGene_uc002hho.1, hg19_knownGene_uc010wcb.2 | MYO1D | chr17 | 31087632 | C | T | 0 | DAFAKAIYERLFCWIVTRI | DAFAKAIYEHLFCWIVTRI | SEQ ID NO: 172 | AIYEHLFCWI | 118 | high |
| hg19_knownGene_uc010nzv.1, hg19_knownGene_uc001aok.4, hg19_knownGene_uc001aoi.3, hg19_knownGene_uc001aoj.3 | CAMTA1 | chr1 | 7797322 | C | T | 0 | HFSCTPLMWACALGHLEAA | HFSCTPLMWVCALGHLEAA | SEQ ID NO: 173 | LMWVCALGHL | 120 | high |
| hg19_knownGene_uc001bnm.4, hg19_knownGene_uc001bnn.3 | SLC9A1 | chr1 | 27436202 | C | T | 0 | HVGIVDIFLGFLSFFVVAL | HVGIVDIFLSFLSFFVVAL | SEQ ID NO: 174 | GIVDIFLSFL | 125 | high |

TABLE 6-continued

Neoepitopes (10-mer) with high binding affinity for HLA-A0201

| transcript | gene | chr | pos | ref | alt | expr (RPKM) | WT_AA | MT_AA | MTpep | | MT_ic50 | Score level |
|---|---|---|---|---|---|---|---|---|---|---|---|---|
| hg19_knownGene_uc011dzr.2, hg19_knownGene_uc011dzt.2, hg19_knownGene_uc011dzt.2, hg19_knownGene_uc010kbz.3, hg19_knownGene_uc010kca.3, hg19_knownGene_uc003pmq.4, hg19_knownGene_uc011dzs.2, hg19_knownGene_uc021zco.1 | CNR1 | chr6 | 88853864 | G | A | 0 | FGKMNKLIKTVFAFCSMLC | FGKMNKLIKMVFAFCSMLC | SEQ ID NO: 175 | KMVFAFCSML | 127 | high |
| hg19_knownGene_uc003vsp.2 | WDR91 | chr7 | 134894422 | C | T | 0 | LRDYWSYLERRLFSRLEDI | LRDYWSYLEHRLFSRLEDI | SEQ ID NO: 176 | YLEHRLFSRL | 143 | medium |
| hg19_knownGene_uc011eao.2, hg19_knownGene_uc003pss.4 | ARMC2 | chr6 | 109286202 | G | T | 0 | IKKLVDCLRDLGPTDWQLA | IKKLVDCLRYLGPTDWQLA | SEQ ID NO: 177 | YLGPTDWQLA | 157 | high |
| hg19_knownGene_uc002gio.3, hg19_knownGene_uc010cng.2, hg19_knownGene_uc002gim.3, hg19_knownknownGene_uc010cni.2, hg19_knownGene_uc031qyq.1, hg19_knownGene_uc010cnf.2 hg19_knownGene_uc002gin.3, hg19_knownGene_uc010cnh.2, hg19_knownGene_uc002gig.1, hg19_knownGene_uc002gih.3, hg19_knownGene_uc002gij.3, hg19_knownGene_uc002gii.2 | TP53 | chr17 | 7577539 | G | A | 0 | NSSCMGGMNRRPILTIITL | NSSCMGGMNWRPILTIITL | SEQ ID NO: 178 | GMNWRPILTI | 163 | high |

TABLE 6-continued

Neoepitopes (10-mer) with high binding affinity for HLA-A0201

| transcript | gene | chr | pos | ref | alt | expr (RPKM) | WT_AA | MT_AA | MTpep | MT_ic50 | Score level |
|---|---|---|---|---|---|---|---|---|---|---|---|
| hg19_knownGene_uc003jml.2, hg19_knownGene_uc003jmk.3 | C6 | chr5 | 41149516 | T | G | 0 | NDYFTSPACKFLAEKCLNN | NDYFTSPACTFLAEKCLNN | SEQ ID NO: 179 | FTSPACTFLA | 176 | high |
| hg19_knownGene_uc003bve.1 | IRAK2 | chr3 | 10264468 | C | T | 0 | AAYLPEDFIRVGQLTKRVD | AAYLPEDFIWVGQLTKRVD | SEQ ID NO: 180 | YLPEDFIWVG | 179 | high |
| hg19_knownGene_uc011kis.2, hg19_knownGene_uc003upp.3, hg19_knownGene_uc003upr.3 | TRRAP | chr7 | 98519385 | C | T | 0 | RAELMQALWRTLRNPADSI | RAELMQALWCTLRNPADSI | SEQ ID NO: 181 | ELMQALWCTL | 190 | high |
| hg19_knownGene_uc001gut.2, hg19_knownGene_uc001gur.2 | PTPRC | chr1 | 198711490 | A | C | 0 | LRRQRCLMVQVEAQYILIH | LRRQRCLMVHVEAQYILIH | SEQ ID NO: 182 | LMVHVEAQYI | 194 | high |
| hg19_knownGene_uc003yhw.3, hg19_knownGene_uc010mbe.2 | CPQ | chr8 | 97797433 | T | G | 0 | NLQQDGLEKVHLEPVRIPH | NLQQDGLEKGHLEPVRIPH | SEQ ID NO: 183 | GLEKGHLEPV | 194 | medium |
| hg19_knownGene_uc011bai.2, hg19_knownGene_uc011baj.2 | SLC6A20 | chr3 | 45817323 | G | A | 0 | ENGGVQWEPALCLLLAWLV | ENGGVQWEPVCLLLLAWLV | SEQ ID NO: 184 | VQWEPVLCLL | 195 | high |
| hg19_knownGene_uc002viv.3, hg19_knownGene_uc002viu.3 | STK36 | chr2 | 219558685 | G | A | 0 | LYFLSLLVFRLQNLPCGME | LYFLSLLVFQLQNLPCGME | SEQ ID NO: 185 | YFLSLLVFQL | 195 | high |
| hg19_knownGene_uc001vpa.2, hg19_knownGene_uc001voz.2, hg19_knownGene_uc001vox.1 | NALCN | chr13 | 102029355 | C | T | 0 | DQMSPWGMLRIPRPLIMIR | DQMSPWGMLQIPRPLIMIR | SEQ ID NO: 186 | GMLQIPRPLI | 197 | medium |
| hg19_knownGene_uc010tkh.2, hg19_knownGene_uc001vuh.3 | TMEM255B | chr13 | 114469097 | C | T | 0 | GLLDPAEGLSRRKKTSLWF | GLLDPAEGLLRRKKTSLWF | SEQ ID NO: 187 | GLLDPAEGLL | 213 | high |

TABLE 6-continued

Neoepitopes (10-mer) with high binding affinity for HLA-A0201

| transcript | gene | chr | pos | ref | alt | expr (RPKM) | WT_AA | MT_AA | MTpep | MT_ic50 | Score level |
|---|---|---|---|---|---|---|---|---|---|---|---|
| hg19_knownGene_uc011kis.2, hg19_knownGene_uc003upp.3, hg19_knownGene_uc003upr.3 | TRRAP | chr7 | 98519385 | C | T | 0 | RAELMQALWRTLRNPADSI | RAELMQALWCTLRNPADSI | SEQ ID NO: 188 | ALWCTLRNPA | 225 | medium |
| hg19_knownGene_uc002xxm.1, hg19_knownGene_uc002xxn.1, hg19_knownGene_uc002xxl.1 | CSTF1 | chr20 | 54978601 | G | A | 0 | HTEDYVLLPDERTISLCCW | HTEDYVLLPNERTISLCCW | SEQ ID NO: 189 | LLPNERTISL | 235 | high |
| hg19_knownGene_uc003fjk.3 | PIK3CA | chr3 | 178916891 | G | A | 0 | DETRRLCDLRLFQPFLKVI | DETRRLCDLQLFQPFLKVI | SEQ ID NO: 190 | LQLFQPFLKV | 238 | high |
| hg19_knownGene_uc009yrn.1 | ADRBK1 | chr11 | 67051736 | C | T | 0 | RNFPLTISERWQQEVAETV | RNFPLTISEWWQQEVAETV | SEQ ID NO: 191 | TISEWWQQEV | 239 | high |
| hg19_knownGene_uc010hiq.3, hg19_knownGene_uc003cnx.4 | KIF15 | chr3 | 44828026 | C | T | 0 | IKKGVFVVGAVEQVVTSAA | IKKGVFVVGVVEQVVTSAA | SEQ ID NO: 192 | FVVGVVEQVV | 248 | high |
| hg19_knownGene_uc002dli.3 | HS3ST2 | chr16 | 22926539 | G | A | 0 | WNAIRIGMYVLHLESWLQY | WNAIRIGMYMLHLESWLQY | SEQ ID NO: 193 | YMLHLESWLQ | 253 | high |
| hg19_knownGene_uc001mco.3 | CNGA4 | chr11 | 6265440 | A | C | 0 | DQQLDDLQTKFARLLAELE | DQQLDDLQTTFARLLAELE | SEQ ID NO: 194 | QLDDLQTTFA | 254 | medium |
| hg19_knownGene_uc001rgq.1, hg19_knownGene_uc001rgp.1 | KRAS | chr12 | 25398285 | C | T | 0 | EYKLVVVGAGGVGKSALTI | EYKLVVVGASGVGKSALTI | SEQ ID NO: 195 | KLVVVGASGV | 256 | high |
| hg19_knownGene_uc002hue.3, hg19_knownGene_uc010cwt.1 | CASC3 | chr17 | 38324639 | C | T | 0 | PYAPGALPPPPPPHLYPNT | PYAPGALPPLPPPHLYPNT | SEQ ID NO: 196 | ALPPLPPPHL | 260 | medium |
| hg19_knownGene_uc001vpa.2, hg19_knownGene_uc001voz.2, hg19_knownGene_uc001vox.1 | NALCN | chr13 | 102029355 | C | T | 0 | DQMSPWGMLRIPRPLIMIR | DQMSPWGMLQIPRPLIMIR | SEQ ID NO: 197 | QMSPWGMLQI | 266 | medium |

TABLE 6-continued

Neoepitopes (10-mer) with high binding affinity for HLA-A0201

| transcript | gene | chr | pos | ref | alt | expr (RPKM) | WT_AA | MT_AA | MTpep | MT_ic50 | Score level |
|---|---|---|---|---|---|---|---|---|---|---|---|
| hg19_knownGene_uc001szy.4, hg19_knownGene_uc001szv.4 | SLC6A15 | chr12 | 85279797 | G | A | 0 | ILLMVIGIPLFFLELSVGQ | ILLMVIGIPFFFLELSVGQ | SEQ ID NO: 198 | LLMVIGIPFF | 267 | high |
| hg19_knownGene_uc003zqw.4, hg19_knownGene_uc003zqx.4, hg19_knownGene_uc010mjh.1 | ACO1 | chr9 | 32418455 | G | A | 0 | DGYYYPDSLVGTDSHTTMI | DGYYYPDSLMGTDSHTTMI | SEQ ID NO: 199 | SLMGTDSHTT | 286 | medium |
| hg19_knownGene_uc021ozl.1, hg19_knownGene_uc001fau.3 | IVL | chr1 | 152882716 | A | C | 0 | VKRDEQLGMKKEQLLELPE | VKRDEQLGMTKEQLLELPE | SEQ ID NO: 200 | GMTKEQLLEL | 295 | medium |
| hg19_knownGene_uc001vkp.1, hg19_knownGene_vkq.1, hg19_knownGene_uc001vko.2, hg19_knownGene_uc010aez.1 | EDNRB | chr13 | 78492668 | G | A | 0 | PSLCGRALVALVLACGLSR | PSLCGRALVVLVLACGLSR | SEQ ID NO: 201 | SLCGRALVVL | 309 | medium |
| hg19_knownGene_uc002viv.3, hg19_knownGene_uc002viu.3 | STK36 | chr2 | 219558685 | G | A | 0 | LYFLSLLVFRLQNLPCGME | LYFLSLLVFQLQNLPCGME | SEQ ID NO: 202 | FQLQNLPCGM | 315 | high |
| hg19_knownGene_uc002bxi.3, hg19_knownGene_uc002bxh.3, hg19_knownGene_uc002bxj.3 | TM2D3 | chr15 | 102182749 | G | A | 0 | FSFGGLGIWTLIDVLLIGV | FSFGGLGIWMLIDVLLIGV | SEQ ID NO: 203 | GIWMLIDVLL | 330 | medium |
| hg19_knownGene_uc022azb.1, hg19_knownGene_uc003yin.3 | KCNS2 | chr8 | 99441361 | C | T | 0 | GYGDVVPGTTAGKLTASAC | GYGDVVPGTMAGKLTASAC | SEQ ID NO: 204 | TMAGKLTASA | 345 | medium |
| hg19_knownGene_uc003lmh.4, hg19_knownGene_uc010jgh.3, hg19_knownGene_uc003lmf.4, hg19_knownGene_uc003lmg.4 | GNPDA1 | chr5 | 141384531 | G | A | 0 | LTKVPTMALTVGVGTVMDA | LTKVPTMALMVGVGTVMDA | SEQ ID NO: 205 | ALMVGVGTVM | 363 | high |

TABLE 6-continued

Neoepitopes (10-mer) with high binding affinity for HLA-A0201

| transcript | gene | chr | pos | ref | alt | expr (RPKM) | WT_AA | MT_AA | MTpep | MT_ic50 | Score level |
|---|---|---|---|---|---|---|---|---|---|---|---|
| hg19_knownGene_uc003xrh.1, hg19_knownGene_uc022aup.1, hg19_knownGene_uc010lyc.1, hg19_knownGene_uc003xri.1 | OPRK1 | chr8 | 54142147 | C | T | 0 | VLVVVAVFVVCWTPIHIFI | VLVVVAVFVICWTPIHIFI | SEQ ID NO: 206 | VLVVVAVFVI | 372 | high |
| hg19_knownGene_uc001mmd.3, hg19_knownGene_uc001mmf.3 | SOX6 | chr11 | 16077437 | G | A | 0 | SPLQLQQLYAAQLASMQVS | SPLQLQQLYVAQLASMQVS | SEQ ID NO: 207 | QLYVAQLASM | 384 | medium |
| hg19_knownGene_uc001mmg.3, hg19_knownGene_uc001mme.3 | SOX6 | chr11 | 16077437 | G | A | 0 | NHKQIEQLYAAQLASMQVS | NHKQIEQLYVAQLASMQVS | SEQ ID NO: 208 | QLYVAQLASM | 384 | medium |
| hg19_knownGene_uc002lkw.3, hg19_knownGene_uc002lky.2 | NETO1 | chr18 | 70451000 | G | A | 0 | STVANDVMLRTGLGVIRMW | STVAMDVMLCTGLGVIRMW | SEQ ID NO: 209 | VMLCTGLGVI | 401 | medium |
| hg19_knownGene_xuj.3, hg19_knownGene_uc001xul.3, hg19_knownGene_uc001xui.3 | ADCK1 | chr14 | 78397931 | G | A | 0 | ISHLLNHVPRQMLLILKTN | ISHLLNHVPHQMLLILKTN | SEQ ID NO: 210 | HLLNHVPHQM | 403 | medium |
| hg19_knownGene_uc003pue.3, hg19_knownGene_uc003puf.3 | SLC22A16 | chr6 | 110746270 | C | T | 0 | IPQLFVGTMALLSGVLTLK | IPQLFVGTMTLLSGVLTLK | SEQ ID NO: 211 | MTLLSGVLTL | 434 | medium |
| hg19_knownGene_uc001szy.4, hg19_knownGene_uc001szv.4 | SLC6A15 | chr12 | 85279797 | G | A | 0 | ILLMVIGIPLFFLELSVGQ | ILLMVIGIPFFFLELSVGQ | SEQ ID NO: 212 | LMVIGIPFFF | 447 | medium |
| hg19_knownGene_uc003xrh.1, hg19_knownGene_uc022aup.1, hg19_knownGene_uc010lyc.1, hg19_knownGene_uc003xri.1 | OPRK1 | chr8 | 54142147 | C | T | 0 | VLVVVAVFVVCWTPIHIFI | VLVVVAVFVICWTPIHIFI | SEQ ID NO: 213 | AVFVICWTPI | 448 | medium |

TABLE 6-continued

Neoepitopes (10-mer) with high binding affinity for HLA-A0201

| transcript | gene | chr | pos | ref | alt | expr (RPKM) | WT_AA | MT_AA | MTpep | | MT_ic50 | Score level |
|---|---|---|---|---|---|---|---|---|---|---|---|---|
| hg19_knownGene_uc002hbi.3, hg19_knownGene_uc002hbh.3, hg19_knownGene_uc010wal.1, hg19_knownGene_uc010wam.2, hg19_knownGene_uc010wan.2 | SLC13A2 | chr17 | 26817568 | G | A | 0 | EHWNLHKRIALRVLLIVGV | EHWNLHKRITLRVLLIVGV | SEQ ID NO: 214 | TLRVLLIVGV | 457 | medium |

As shown in Tables 1 to 3 above, the following neoepitopes with high binding affinity for HLA-A2402 were selected through in silico prediction: AYNSISSEVI (SEQ ID NO: 45) ($IC_{50}$=274 nM), TYQNDNKPEF (SEQ ID NO: 42) ($IC_{50}$=187 nM), FFYPCHPDVF (SEQ ID NO 49) ($IC_{50}$=436 nM), VYNMPSTPSF (SEQ ID NO 32) ($IC_{50}$=38 nM), RYLGPTDWQL (SEQ ID NO 41) ($IC_{50}$=159 nM), LMVIGIPFFF (SEQ ID NO: 48) ($IC_{50}$=404 nM).

In addition, as shown in Tables 4 to 6, the following neoepitopes with high binding affinity for HLA-A0201 were selected: MLIDVLLIGV (SEQ ID NO: 122) ($IC_{50}$=4 nM), MMDRQMLPPV (SEQ ID NO: 123) ($IC_{50}$=6 nM), LMWVCALGHL (SEQ ID NO: 173) ($IC_{50}$=120 nM), GIVDIFLSFL (SEQ ID NO: 174) ($IC_{50}$=125 nM), AVFVICWTPI (SEQ ID NO: 213) ($IC_{50}$=448 nM), TLRVLLIVGV (SEQ ID NO: 214) ($IC_{50}$=457 nM).

The neoepitopes selected as above were synthesized into prepared MHC-peptide multimers (8-, 9-, 10-mer) for the following experiments. Using these multimers, cells capable of recognizing the same were extracted from patient-derived T cells, and then EBV-negative gastric cancer cell antigen-specific autologous memory T cells were produced.

2. ELISPOT Results for T Cells Activated by Dendritic Cells Loaded with Selected Neoepitope PBMCs extracted from healthy human blood were separated into monocytes and leukocytes through flow cytometry, and the monocytes were cultured for 2 days in a culture supplemented with cytokines GM-CSF and IL-4 to differentiate into dendritic cells. In addition, the leukocytes were cultured with anti-CD3/CD28 antibody for 3 days, and then cultured in a culture supplemented with cytokine IL-2. The neoepitope peptide selected as above was transferred to the monocyte-differentiated dendritic cells using electroporation. Subsequently, culture was performed for 5 days to identify that the neoepitope has been expressed on the surface of the dendritic cells. Then, the dendritic cells were co-cultured with the leukocytes, which were cultured in a culture supplemented with anti-CD3/CD28 antibody, at a ratio of 1:20 (dendritic cells:leukocytes). In a case of the co-culture, the culture was mixed with a cytokine cocktail containing both cytokine IL-4 that increases the antigen-presenting function of dendritic cells, and cytokines IL-2 and IL-7 that function to help conversion of T cells into memory cells, and culture was performed. After 16 hours, expression levels of IFN-γ in the T cells thus activated were measured with ELISPOT, and the results are illustrated in FIGS. 1 to 4. In order to select memory T cells to which an antigen had been presented through the dendritic cells after co-culture for 72 hours, a magnetic-activated cell sorter (MACS) capable of extracting T cells secreting cytokine IFN-γ was used to extract EBV antigen-specific memory T cells. The extracted memory T cells were cultured in a culture supplemented with cytokines IL-2, IL-7, and IL-15 to maintain their memory function and increase the number of cells, in which the culture was performed until the memory T cells reach the number of cells that can be injected into mice. Here, as a control, cells to which an unstimulated EBV-positive gastric cancer peptide (HLA-A3101) had been delivered were used.

As a result, it was found that the T-cells cultured with dendritic cells loaded with a neoepitope peptide, which has been predicted through Neopepsee, secrete much more IFN-γ than the control regardless of binding affinity of the peptide for HLA.

From these results, it was found that in the present invention, cytotoxic T lymphocytes (CTLs) can be activated by the dendritic cells loaded with each of neoepitopes, which have high binding affinity for HLA-A2402 and HLA-A0201 in Tables 1 to 6 above, and the thus activated T cells have antigen specificity which enables recognition of the neoepitope that is a neoantigen.

Although specific parts of the present invention have been described in detail as above, it is obvious to those skilled in the art that such a specific description is merely a preferred embodiment, and the scope of the present invention is not limited thereto. Therefore, the substantial scope of the present invention will be defined by the appended claims and equivalents thereof.

INDUSTRIAL APPLICABILITY

The present invention relates to a cancer-specific tumor antigen neoepitope, an antigen-presenting cell loaded with the neoepitope, and a method for activating T cells for cancer treatment using the antigen-presenting cell.

The invention claimed is:

1. A method for preventing or treating cancer, the method comprising a step of administering to a target individual an antigen-presenting cell loaded with an Epstein-Barr virus (EBV)-negative cancer-specific tumor antigen neoepitope comprising any one of SEQ ID NOs: 4, 7-9, 11, 14-15, 100, 121, 122, 186 and 214.

2. The method according to claim 1, wherein the antigen-presenting cell is a dendritic cell, a B cell, or a macrophage.

3. The method according to claim 1, wherein the antigen-presenting cell promotes proliferation or differentiation of T cells.

4. The method according claim 1, wherein the Epstein-Barr virus (EBV)-negative cancer-specific tumor antigen neoepitope exhibits binding affinity with at least one of HLA-A, HLA-B, HLA-C, HLA-E, HLA-F, HLA-G, β2-microglobulin, HLA-DPA1, HLA-DPB1, HLA-DQA1, HLA-DQB1, HLA-DRA1, HLA-DRB1, HLA-DRB3, HLA-DRB4, HLA-DRB5, HLA-DM, HLA-DOA, and HLA-DOB loci.

5. The method according claim 1, wherein the Epstein-Barr virus (EBV)-negative cancer-specific tumor antigen neoepitope exhibits binding affinity with at least one of HLA-A*2402 and HLA-A*A0201.

6. The method according to claim 1, wherein the cancer is Epstein-Barr virus (EBV)-negative cancer.

7. The method according to claim 1, wherein the cancer is colorectal cancer, pancreatic cancer, gastric cancer, liver cancer, breast cancer, cervical cancer, thyroid cancer, parathyroid cancer, lung cancer, non-small cell lung cancer, prostate cancer, gallbladder cancer, biliary tract cancer, non-Hodgkin lymphoma, Hodgkin lymphoma, blood cancer, bladder cancer, kidney cancer, ovarian cancer, melanoma, colon cancer, bone cancer, skin cancer, head cancer, uterine cancer, rectal cancer, brain tumor, perianal cancer, fallopian tube carcinoma, endometrial carcinoma, vaginal cancer, vulvar carcinoma, esophageal cancer, small intestine cancer, endocrine adenocarcinoma, adrenal cancer, soft tissue sarcoma, urethral cancer, penile cancer, ureteral cancer, renal cell carcinoma, renal pelvic carcinoma, central nervous system (CNS) tumor, primary CNS lymphoma, spinal cord tumor, brain stem glioma, or pituitary adenoma.

* * * * *

SEQUENCE LISTING

<160> NUMBER OF SEQ ID NOS: 215

<210> SEQ ID NO 1
<211> LENGTH: 8
<212> TYPE: PRT
<213> ORGANISM: Artificial Sequence
<220> FEATURE:
<223> OTHER INFORMATION: synthetic peptide

<400> SEQUENCE: 1

Ile Tyr Glu His Leu Phe Cys Trp
1               5

<210> SEQ ID NO 2
<211> LENGTH: 9
<212> TYPE: PRT
<213> ORGANISM: Artificial Sequence
<220> FEATURE:
<223> OTHER INFORMATION: Synthetic peptide

<400> SEQUENCE: 2

Ile Tyr Gln Lys Val Cys His Arg Met
1               5

<210> SEQ ID NO 3
<211> LENGTH: 9
<212> TYPE: PRT
<213> ORGANISM: Artificial Sequence
<220> FEATURE:
<223> OTHER INFORMATION: Synthetic peptide

<400> SEQUENCE: 3

Leu Trp His Gln Val Phe Phe Asp Ile
1               5

<210> SEQ ID NO 4
<211> LENGTH: 9
<212> TYPE: PRT
<213> ORGANISM: Artificial Sequence
<220> FEATURE:
<223> OTHER INFORMATION: Synthetic peptide

<400> SEQUENCE: 4

Lys His Pro Glu Pro Phe Phe Thr Leu
1               5

<210> SEQ ID NO 5
<211> LENGTH: 9
<212> TYPE: PRT
<213> ORGANISM: Artificial Sequence
<220> FEATURE:
<223> OTHER INFORMATION: Synthetic peptide

<400> SEQUENCE: 5

Ser Tyr Leu Glu Asp Val Arg Leu Ile
1               5

<210> SEQ ID NO 6
<211> LENGTH: 9
<212> TYPE: PRT
<213> ORGANISM: Artificial Sequence
<220> FEATURE:
<223> OTHER INFORMATION: Synthetic peptide

<400> SEQUENCE: 6

Leu Tyr Pro Asn Thr Gln Ala Pro Leu
1               5

```
<210> SEQ ID NO 7
<211> LENGTH: 9
<212> TYPE: PRT
<213> ORGANISM: Artificial Sequence
<220> FEATURE:
<223> OTHER INFORMATION: Synthetic peptide

<400> SEQUENCE: 7

Ile Trp Met Leu Ile Asp Val Leu Leu
1               5

<210> SEQ ID NO 8
<211> LENGTH: 9
<212> TYPE: PRT
<213> ORGANISM: Artificial Sequence
<220> FEATURE:
<223> OTHER INFORMATION: Synthetic peptide

<400> SEQUENCE: 8

Asn Phe Ser Ser His Phe Asn His Phe
1               5

<210> SEQ ID NO 9
<211> LENGTH: 9
<212> TYPE: PRT
<213> ORGANISM: Artificial Sequence
<220> FEATURE:
<223> OTHER INFORMATION: Synthetic peptide

<400> SEQUENCE: 9

His Phe Gln Pro Phe His Gly Leu Phe
1               5

<210> SEQ ID NO 10
<211> LENGTH: 9
<212> TYPE: PRT
<213> ORGANISM: Artificial Sequence
<220> FEATURE:
<223> OTHER INFORMATION: Synthetic peptide

<400> SEQUENCE: 10

Ile Trp Leu Arg Lys Ala Leu Asp Phe
1               5

<210> SEQ ID NO 11
<211> LENGTH: 9
<212> TYPE: PRT
<213> ORGANISM: Artificial Sequence
<220> FEATURE:
<223> OTHER INFORMATION: Synthetic peptide

<400> SEQUENCE: 11

Tyr Tyr Arg Cys Pro Leu Gln Val Leu
1               5

<210> SEQ ID NO 12
<211> LENGTH: 9
<212> TYPE: PRT
<213> ORGANISM: Artificial Sequence
<220> FEATURE:
<223> OTHER INFORMATION: Synthetic peptide

<400> SEQUENCE: 12

Tyr Phe Thr Ser Pro Ala Cys Thr Phe
1               5
```

```
<210> SEQ ID NO 13
<211> LENGTH: 9
<212> TYPE: PRT
<213> ORGANISM: Artificial Sequence
<220> FEATURE:
<223> OTHER INFORMATION: Synthetic peptide

<400> SEQUENCE: 13

Ala Phe Leu Leu Trp Lys Lys Arg Phe
1               5

<210> SEQ ID NO 14
<211> LENGTH: 9
<212> TYPE: PRT
<213> ORGANISM: Artificial Sequence
<220> FEATURE:
<223> OTHER INFORMATION: Synthetic peptide

<400> SEQUENCE: 14

Trp Tyr Ala Asn Gly Ala Ala His Leu
1               5

<210> SEQ ID NO 15
<211> LENGTH: 9
<212> TYPE: PRT
<213> ORGANISM: Artificial Sequence
<220> FEATURE:
<223> OTHER INFORMATION: Synthetic peptide

<400> SEQUENCE: 15

Ser Tyr Leu Ala His His Trp Arg Ile
1               5

<210> SEQ ID NO 16
<211> LENGTH: 9
<212> TYPE: PRT
<213> ORGANISM: Artificial Sequence
<220> FEATURE:
<223> OTHER INFORMATION: Synthetic peptide

<400> SEQUENCE: 16

Ile Phe Leu Ser Phe Leu Ser Phe Phe
1               5

<210> SEQ ID NO 17
<211> LENGTH: 9
<212> TYPE: PRT
<213> ORGANISM: Artificial Sequence
<220> FEATURE:
<223> OTHER INFORMATION: Synthetic peptide

<400> SEQUENCE: 17

Met Val Ile Gly Ile Pro Phe Phe Phe
1               5

<210> SEQ ID NO 18
<211> LENGTH: 9
<212> TYPE: PRT
<213> ORGANISM: Artificial Sequence
<220> FEATURE:
<223> OTHER INFORMATION: Synthetic peptide

<400> SEQUENCE: 18

Met Val Ile Gly Ile Pro Phe Phe Phe
1               5
```

```
<210> SEQ ID NO 19
<211> LENGTH: 9
<212> TYPE: PRT
<213> ORGANISM: Artificial Sequence
<220> FEATURE:
<223> OTHER INFORMATION: Synthetic peptide

<400> SEQUENCE: 19

Val Tyr Gly Val Glu Ser His Val Leu
1               5

<210> SEQ ID NO 20
<211> LENGTH: 9
<212> TYPE: PRT
<213> ORGANISM: Artificial Sequence
<220> FEATURE:
<223> OTHER INFORMATION: Synthetic peptide

<400> SEQUENCE: 20

Val Tyr Gly Val Glu Ser His Val Leu
1               5

<210> SEQ ID NO 21
<211> LENGTH: 9
<212> TYPE: PRT
<213> ORGANISM: Artificial Sequence
<220> FEATURE:
<223> OTHER INFORMATION: Synthetic peptide

<400> SEQUENCE: 21

Val Phe Val Ile Cys Trp Thr Pro Ile
1               5

<210> SEQ ID NO 22
<211> LENGTH: 9
<212> TYPE: PRT
<213> ORGANISM: Artificial Sequence
<220> FEATURE:
<223> OTHER INFORMATION: Synthetic peptide

<400> SEQUENCE: 22

Ile Tyr Glu His Leu Phe Cys Trp Ile
1               5

<210> SEQ ID NO 23
<211> LENGTH: 9
<212> TYPE: PRT
<213> ORGANISM: Artificial Sequence
<220> FEATURE:
<223> OTHER INFORMATION: Synthetic peptide

<400> SEQUENCE: 23

Ser Gln Pro Trp Gln Val Ala Leu Phe
1               5

<210> SEQ ID NO 24
<211> LENGTH: 9
<212> TYPE: PRT
<213> ORGANISM: Artificial Sequence
<220> FEATURE:
<223> OTHER INFORMATION: Synthetic peptide

<400> SEQUENCE: 24

Ala Tyr Leu Pro Glu Asp Phe Ile Trp
1               5

<210> SEQ ID NO 25
```

```
<211> LENGTH: 9
<212> TYPE: PRT
<213> ORGANISM: Artificial Sequence
<220> FEATURE:
<223> OTHER INFORMATION: Synthetic peptide

<400> SEQUENCE: 25

Met Tyr Met Leu His Leu Glu Ser Trp
1               5

<210> SEQ ID NO 26
<211> LENGTH: 9
<212> TYPE: PRT
<213> ORGANISM: Artificial Sequence
<220> FEATURE:
<223> OTHER INFORMATION: Synthetic peptide

<400> SEQUENCE: 26

Arg Tyr Leu Met Arg Arg Arg Arg Ile
1               5

<210> SEQ ID NO 27
<211> LENGTH: 9
<212> TYPE: PRT
<213> ORGANISM: Artificial Sequence
<220> FEATURE:
<223> OTHER INFORMATION: Synthetic peptide

<400> SEQUENCE: 27

Thr Phe Ile Ser Glu Asn His Leu Ile
1               5

<210> SEQ ID NO 28
<211> LENGTH: 9
<212> TYPE: PRT
<213> ORGANISM: Artificial Sequence
<220> FEATURE:
<223> OTHER INFORMATION: Synthetic peptide

<400> SEQUENCE: 28

Lys Leu Ile Lys Met Val Phe Ala Phe
1               5

<210> SEQ ID NO 29
<211> LENGTH: 9
<212> TYPE: PRT
<213> ORGANISM: Artificial Sequence
<220> FEATURE:
<223> OTHER INFORMATION: Synthetic peptide

<400> SEQUENCE: 29

Cys Leu Ser Arg Ala Ser Phe Leu Phe
1               5

<210> SEQ ID NO 30
<211> LENGTH: 9
<212> TYPE: PRT
<213> ORGANISM: Artificial Sequence
<220> FEATURE:
<223> OTHER INFORMATION: Synthetic peptide

<400> SEQUENCE: 30

Phe Tyr Pro Cys His Pro Asp Val Phe
1               5

<210> SEQ ID NO 31
<211> LENGTH: 10
```

```
<212> TYPE: PRT
<213> ORGANISM: Artificial Sequence
<220> FEATURE:
<223> OTHER INFORMATION: Synthetic peptide

<400> SEQUENCE: 31

Ala Tyr Ala Glu Arg Leu Gly Met Thr Phe
1               5                   10

<210> SEQ ID NO 32
<211> LENGTH: 10
<212> TYPE: PRT
<213> ORGANISM: Artificial Sequence
<220> FEATURE:
<223> OTHER INFORMATION: Synthetic peptide

<400> SEQUENCE: 32

Val Tyr Asn Met Pro Ser Thr Pro Ser Phe
1               5                   10

<210> SEQ ID NO 33
<211> LENGTH: 10
<212> TYPE: PRT
<213> ORGANISM: Artificial Sequence
<220> FEATURE:
<223> OTHER INFORMATION: Synthetic peptide

<400> SEQUENCE: 33

Tyr Trp Ser Tyr Leu Glu His Arg Leu Phe
1               5                   10

<210> SEQ ID NO 34
<211> LENGTH: 10
<212> TYPE: PRT
<213> ORGANISM: Artificial Sequence
<220> FEATURE:
<223> OTHER INFORMATION: Synthetic peptide

<400> SEQUENCE: 34

Ile Trp Met Leu Ile Asp Val Leu Leu Ile
1               5                   10

<210> SEQ ID NO 35
<211> LENGTH: 10
<212> TYPE: PRT
<213> ORGANISM: Artificial Sequence
<220> FEATURE:
<223> OTHER INFORMATION: Synthetic peptide

<400> SEQUENCE: 35

Asp Tyr Phe Thr Ser Pro Ala Cys Thr Phe
1               5                   10

<210> SEQ ID NO 36
<211> LENGTH: 10
<212> TYPE: PRT
<213> ORGANISM: Artificial Sequence
<220> FEATURE:
<223> OTHER INFORMATION: Synthetic peptide

<400> SEQUENCE: 36

Ile Tyr Ser Val Ala Val Leu Ala Cys Ile
1               5                   10

<210> SEQ ID NO 37
<211> LENGTH: 10
<212> TYPE: PRT
```

<213> ORGANISM: Artificial Sequence
<220> FEATURE:
<223> OTHER INFORMATION: Synthetic peptide

<400> SEQUENCE: 37

Tyr Tyr Asn Met Ala Asn Gly Thr Val Ile
1               5                   10

<210> SEQ ID NO 38
<211> LENGTH: 10
<212> TYPE: PRT
<213> ORGANISM: Artificial Sequence
<220> FEATURE:
<223> OTHER INFORMATION: Synthetic peptide

<400> SEQUENCE: 38

Val Trp Gly Pro Gln Leu Gly Arg Leu Phe
1               5                   10

<210> SEQ ID NO 39
<211> LENGTH: 10
<212> TYPE: PRT
<213> ORGANISM: Artificial Sequence
<220> FEATURE:
<223> OTHER INFORMATION: Synthetic peptide

<400> SEQUENCE: 39

Phe Tyr Pro Cys His Pro Asp Val Phe Ile
1               5                   10

<210> SEQ ID NO 40
<211> LENGTH: 10
<212> TYPE: PRT
<213> ORGANISM: Artificial Sequence
<220> FEATURE:
<223> OTHER INFORMATION: Synthetic peptide

<400> SEQUENCE: 40

Ser Tyr Ile Pro Lys Cys Gly Lys Lys Phe
1               5                   10

<210> SEQ ID NO 41
<211> LENGTH: 10
<212> TYPE: PRT
<213> ORGANISM: Artificial Sequence
<220> FEATURE:
<223> OTHER INFORMATION: Synthetic peptide

<400> SEQUENCE: 41

Arg Tyr Leu Gly Pro Thr Asp Trp Gln Leu
1               5                   10

<210> SEQ ID NO 42
<211> LENGTH: 10
<212> TYPE: PRT
<213> ORGANISM: Artificial Sequence
<220> FEATURE:
<223> OTHER INFORMATION: Synthetic peptide

<400> SEQUENCE: 42

Thr Tyr Gln Asn Asp Asn Lys Pro Glu Phe
1               5                   10

<210> SEQ ID NO 43
<211> LENGTH: 10
<212> TYPE: PRT
<213> ORGANISM: Artificial Sequence

```
<220> FEATURE:
<223> OTHER INFORMATION: Synthetic peptide

<400> SEQUENCE: 43

Met Tyr Met Leu His Leu Glu Ser Trp Leu
1               5                   10

<210> SEQ ID NO 44
<211> LENGTH: 10
<212> TYPE: PRT
<213> ORGANISM: Artificial Sequence
<220> FEATURE:
<223> OTHER INFORMATION: Synthetic peptide

<400> SEQUENCE: 44

Val Phe Phe Asp Ile Ala Ile Phe Val Ile
1               5                   10

<210> SEQ ID NO 45
<211> LENGTH: 10
<212> TYPE: PRT
<213> ORGANISM: Artificial Sequence
<220> FEATURE:
<223> OTHER INFORMATION: Synthetic peptide

<400> SEQUENCE: 45

Ala Tyr Asn Ser Ile Ser Ser Glu Val Ile
1               5                   10

<210> SEQ ID NO 46
<211> LENGTH: 10
<212> TYPE: PRT
<213> ORGANISM: Artificial Sequence
<220> FEATURE:
<223> OTHER INFORMATION: Synthetic peptide

<400> SEQUENCE: 46

Cys Phe Leu Arg Cys Cys Ser Cys Val Phe
1               5                   10

<210> SEQ ID NO 47
<211> LENGTH: 10
<212> TYPE: PRT
<213> ORGANISM: Artificial Sequence
<220> FEATURE:
<223> OTHER INFORMATION: Synthetic peptide

<400> SEQUENCE: 47

Glu Tyr Tyr Arg Cys Pro Leu Gln Val Leu
1               5                   10

<210> SEQ ID NO 48
<211> LENGTH: 10
<212> TYPE: PRT
<213> ORGANISM: Artificial Sequence
<220> FEATURE:
<223> OTHER INFORMATION: Synthetic peptide

<400> SEQUENCE: 48

Leu Met Val Ile Gly Ile Pro Phe Phe Phe
1               5                   10

<210> SEQ ID NO 49
<211> LENGTH: 10
<212> TYPE: PRT
<213> ORGANISM: Artificial Sequence
<220> FEATURE:
```

-continued

<223> OTHER INFORMATION: Synthetic peptide

<400> SEQUENCE: 49

Phe Phe Tyr Pro Cys His Pro Asp Val Phe
1               5                   10

<210> SEQ ID NO 50
<211> LENGTH: 8
<212> TYPE: PRT
<213> ORGANISM: Artificial Sequence
<220> FEATURE:
<223> OTHER INFORMATION: Synthetic peptide

<400> SEQUENCE: 50

Met Leu Ile Asp Val Leu Leu Ile
1               5

<210> SEQ ID NO 51
<211> LENGTH: 8
<212> TYPE: PRT
<213> ORGANISM: Artificial Sequence
<220> FEATURE:
<223> OTHER INFORMATION: Synthetic peptide

<400> SEQUENCE: 51

Met Leu Asn Asp Ile Val Ala Val
1               5

<210> SEQ ID NO 52
<211> LENGTH: 8
<212> TYPE: PRT
<213> ORGANISM: Artificial Sequence
<220> FEATURE:
<223> OTHER INFORMATION: Synthetic peptide

<400> SEQUENCE: 52

Ser Leu Gly Lys Val Tyr Gly Val
1               5

<210> SEQ ID NO 53
<211> LENGTH: 8
<212> TYPE: PRT
<213> ORGANISM: Artificial Sequence
<220> FEATURE:
<223> OTHER INFORMATION: Synthetic peptide

<400> SEQUENCE: 53

Ser Leu Gly Lys Val Tyr Gly Val
1               5

<210> SEQ ID NO 54
<211> LENGTH: 8
<212> TYPE: PRT
<213> ORGANISM: Artificial Sequence
<220> FEATURE:
<223> OTHER INFORMATION: Synthetic peptide

<400> SEQUENCE: 54

His Leu Leu Gly Phe Leu Gln Ile
1               5

<210> SEQ ID NO 55
<211> LENGTH: 8
<212> TYPE: PRT
<213> ORGANISM: Artificial Sequence
<220> FEATURE:
<223> OTHER INFORMATION: Synthetic peptide

```
<400> SEQUENCE: 55

Met Leu Cys Thr Gly Leu Gly Val
1               5

<210> SEQ ID NO 56
<211> LENGTH: 8
<212> TYPE: PRT
<213> ORGANISM: Artificial Sequence
<220> FEATURE:
<223> OTHER INFORMATION: Synthetic peptide

<400> SEQUENCE: 56

Gly Leu Gly Ile Trp Met Leu Ile
1               5

<210> SEQ ID NO 57
<211> LENGTH: 9
<212> TYPE: PRT
<213> ORGANISM: Artificial Sequence
<220> FEATURE:
<223> OTHER INFORMATION: Synthetic peptide

<400> SEQUENCE: 57

Phe Leu Ser Phe Leu Ser Phe Phe Val
1               5

<210> SEQ ID NO 58
<211> LENGTH: 9
<212> TYPE: PRT
<213> ORGANISM: Artificial Sequence
<220> FEATURE:
<223> OTHER INFORMATION: Synthetic peptide

<400> SEQUENCE: 58

Tyr Leu Pro Glu Asp Phe Ile Trp Val
1               5

<210> SEQ ID NO 59
<211> LENGTH: 9
<212> TYPE: PRT
<213> ORGANISM: Artificial Sequence
<220> FEATURE:
<223> OTHER INFORMATION: Synthetic peptide

<400> SEQUENCE: 59

Ser Met Leu Asn Asp Ile Val Ala Val
1               5

<210> SEQ ID NO 60
<211> LENGTH: 9
<212> TYPE: PRT
<213> ORGANISM: Artificial Sequence
<220> FEATURE:
<223> OTHER INFORMATION: Synthetic peptide

<400> SEQUENCE: 60

Tyr Leu Asn Ser Arg Gln Phe Pro Met
1               5

<210> SEQ ID NO 61
<211> LENGTH: 9
<212> TYPE: PRT
<213> ORGANISM: Artificial Sequence
<220> FEATURE:
<223> OTHER INFORMATION: Synthetic peptide
```

```
<400> SEQUENCE: 61

Phe Leu Ser Leu Leu Val Phe Gln Leu
1               5

<210> SEQ ID NO 62
<211> LENGTH: 9
<212> TYPE: PRT
<213> ORGANISM: Artificial Sequence
<220> FEATURE:
<223> OTHER INFORMATION: Synthetic peptide

<400> SEQUENCE: 62

Tyr Met Leu His Leu Glu Ser Trp Leu
1               5

<210> SEQ ID NO 63
<211> LENGTH: 9
<212> TYPE: PRT
<213> ORGANISM: Artificial Sequence
<220> FEATURE:
<223> OTHER INFORMATION: Synthetic peptide

<400> SEQUENCE: 63

Lys Leu Val Asp Cys Leu Arg Tyr Leu
1               5

<210> SEQ ID NO 64
<211> LENGTH: 9
<212> TYPE: PRT
<213> ORGANISM: Artificial Sequence
<220> FEATURE:
<223> OTHER INFORMATION: Synthetic peptide

<400> SEQUENCE: 64

Ser Met Asp Gln Leu Glu Phe Thr Val
1               5

<210> SEQ ID NO 65
<211> LENGTH: 9
<212> TYPE: PRT
<213> ORGANISM: Artificial Sequence
<220> FEATURE:
<223> OTHER INFORMATION: Synthetic peptide

<400> SEQUENCE: 65

Arg Leu Gly Met Thr Phe Phe Glu Val
1               5

<210> SEQ ID NO 66
<211> LENGTH: 9
<212> TYPE: PRT
<213> ORGANISM: Artificial Sequence
<220> FEATURE:
<223> OTHER INFORMATION: Synthetic peptide

<400> SEQUENCE: 66

Tyr Leu Gly Pro Thr Asp Trp Gln Leu
1               5

<210> SEQ ID NO 67
<211> LENGTH: 9
<212> TYPE: PRT
<213> ORGANISM: Artificial Sequence
<220> FEATURE:
<223> OTHER INFORMATION: Synthetic peptide

<400> SEQUENCE: 67
```

```
Ala Leu Met Gly Ile Phe Asn Phe Met
1               5

<210> SEQ ID NO 68
<211> LENGTH: 9
<212> TYPE: PRT
<213> ORGANISM: Artificial Sequence
<220> FEATURE:
<223> OTHER INFORMATION: Synthetic peptide

<400> SEQUENCE: 68

Arg Leu Ile Pro Ala Val Leu Ser Ile
1               5

<210> SEQ ID NO 69
<211> LENGTH: 9
<212> TYPE: PRT
<213> ORGANISM: Artificial Sequence
<220> FEATURE:
<223> OTHER INFORMATION: Synthetic peptide

<400> SEQUENCE: 69

Thr Leu Leu Ser Gly Val Leu Thr Leu
1               5

<210> SEQ ID NO 70
<211> LENGTH: 9
<212> TYPE: PRT
<213> ORGANISM: Artificial Sequence
<220> FEATURE:
<223> OTHER INFORMATION: Synthetic peptide

<400> SEQUENCE: 70

Phe Leu Ser Met Leu Asn Asp Ile Val
1               5

<210> SEQ ID NO 71
<211> LENGTH: 9
<212> TYPE: PRT
<213> ORGANISM: Artificial Sequence
<220> FEATURE:
<223> OTHER INFORMATION: Synthetic peptide

<400> SEQUENCE: 71

Thr Leu Phe Ser Cys Val Ser Ser Ala
1               5

<210> SEQ ID NO 72
<211> LENGTH: 9
<212> TYPE: PRT
<213> ORGANISM: Artificial Sequence
<220> FEATURE:
<223> OTHER INFORMATION: Synthetic peptide

<400> SEQUENCE: 72

Val Met Leu Cys Thr Gly Leu Gly Val
1               5

<210> SEQ ID NO 73
<211> LENGTH: 9
<212> TYPE: PRT
<213> ORGANISM: Artificial Sequence
<220> FEATURE:
<223> OTHER INFORMATION: Synthetic peptide

<400> SEQUENCE: 73
```

Phe Val Gly Val Val Glu Gln Val
1               5

<210> SEQ ID NO 74
<211> LENGTH: 9
<212> TYPE: PRT
<213> ORGANISM: Artificial Sequence
<220> FEATURE:
<223> OTHER INFORMATION: Synthetic peptide

<400> SEQUENCE: 74

Ala Leu Asn Ser Gly Thr Ser Tyr Ile
1               5

<210> SEQ ID NO 75
<211> LENGTH: 9
<212> TYPE: PRT
<213> ORGANISM: Artificial Sequence
<220> FEATURE:
<223> OTHER INFORMATION: Synthetic peptide

<400> SEQUENCE: 75

Ser Leu Leu Asn Ala Ile Asp Thr Leu
1               5

<210> SEQ ID NO 76
<211> LENGTH: 9
<212> TYPE: PRT
<213> ORGANISM: Artificial Sequence
<220> FEATURE:
<223> OTHER INFORMATION: Synthetic peptide

<400> SEQUENCE: 76

Ser Leu Ser Phe Ser Glu Val Ser Val
1               5

<210> SEQ ID NO 77
<211> LENGTH: 9
<212> TYPE: PRT
<213> ORGANISM: Artificial Sequence
<220> FEATURE:
<223> OTHER INFORMATION: Synthetic peptide

<400> SEQUENCE: 77

Ala Leu Met Val Gly Val Gly Thr Val
1               5

<210> SEQ ID NO 78
<211> LENGTH: 9
<212> TYPE: PRT
<213> ORGANISM: Artificial Sequence
<220> FEATURE:
<223> OTHER INFORMATION: Synthetic peptide

<400> SEQUENCE: 78

Phe Ile Tyr Ser Val Ala Val Leu Ala
1               5

<210> SEQ ID NO 79
<211> LENGTH: 9
<212> TYPE: PRT
<213> ORGANISM: Artificial Sequence
<220> FEATURE:
<223> OTHER INFORMATION: Synthetic peptide

<400> SEQUENCE: 79

Trp Met Leu Ile Asp Val Leu Leu Ile

```
1               5

<210> SEQ ID NO 80
<211> LENGTH: 9
<212> TYPE: PRT
<213> ORGANISM: Artificial Sequence
<220> FEATURE:
<223> OTHER INFORMATION: Synthetic peptide

<400> SEQUENCE: 80

Lys Gln Ile Glu Gln Leu Tyr Val Ala
1               5

<210> SEQ ID NO 81
<211> LENGTH: 9
<212> TYPE: PRT
<213> ORGANISM: Artificial Sequence
<220> FEATURE:
<223> OTHER INFORMATION: Synthetic peptide

<400> SEQUENCE: 81

Leu Leu Asn Tyr Leu Ser Ser Arg Val
1               5

<210> SEQ ID NO 82
<211> LENGTH: 9
<212> TYPE: PRT
<213> ORGANISM: Artificial Sequence
<220> FEATURE:
<223> OTHER INFORMATION: Synthetic peptide

<400> SEQUENCE: 82

Gly Thr Met Thr Leu Leu Ser Gly Val
1               5

<210> SEQ ID NO 83
<211> LENGTH: 9
<212> TYPE: PRT
<213> ORGANISM: Artificial Sequence
<220> FEATURE:
<223> OTHER INFORMATION: Synthetic peptide

<400> SEQUENCE: 83

Met Val Phe Ala Phe Cys Ser Met Leu
1               5

<210> SEQ ID NO 84
<211> LENGTH: 9
<212> TYPE: PRT
<213> ORGANISM: Artificial Sequence
<220> FEATURE:
<223> OTHER INFORMATION: Synthetic peptide

<400> SEQUENCE: 84

Leu Met Gln Ala Leu Trp Cys Thr Leu
1               5

<210> SEQ ID NO 85
<211> LENGTH: 9
<212> TYPE: PRT
<213> ORGANISM: Artificial Sequence
<220> FEATURE:
<223> OTHER INFORMATION: Synthetic peptide

<400> SEQUENCE: 85

Met Ser Leu Gly Lys Val Tyr Gly Val
1               5
```

<210> SEQ ID NO 86
<211> LENGTH: 9
<212> TYPE: PRT
<213> ORGANISM: Artificial Sequence
<220> FEATURE:
<223> OTHER INFORMATION: Synthetic peptide

<400> SEQUENCE: 86

Met Ser Leu Gly Lys Val Tyr Gly Val
1               5

<210> SEQ ID NO 87
<211> LENGTH: 9
<212> TYPE: PRT
<213> ORGANISM: Artificial Sequence
<220> FEATURE:
<223> OTHER INFORMATION: Synthetic peptide

<400> SEQUENCE: 87

Leu Leu Gly Phe Leu Gln Ile Phe Leu
1               5

<210> SEQ ID NO 88
<211> LENGTH: 9
<212> TYPE: PRT
<213> ORGANISM: Artificial Sequence
<220> FEATURE:
<223> OTHER INFORMATION: Synthetic peptide

<400> SEQUENCE: 88

Gly Leu Tyr Pro Pro Leu Val Ser Met
1               5

<210> SEQ ID NO 89
<211> LENGTH: 9
<212> TYPE: PRT
<213> ORGANISM: Artificial Sequence
<220> FEATURE:
<223> OTHER INFORMATION: Synthetic peptide

<400> SEQUENCE: 89

Met Thr Phe Phe Glu Val Ser Pro Leu
1               5

<210> SEQ ID NO 90
<211> LENGTH: 9
<212> TYPE: PRT
<213> ORGANISM: Artificial Sequence
<220> FEATURE:
<223> OTHER INFORMATION: Synthetic peptide

<400> SEQUENCE: 90

Phe Leu Cys Ala Gly Lys Leu Arg Leu
1               5

<210> SEQ ID NO 91
<211> LENGTH: 9
<212> TYPE: PRT
<213> ORGANISM: Artificial Sequence
<220> FEATURE:
<223> OTHER INFORMATION: Synthetic peptide

<400> SEQUENCE: 91

Lys Met Asn Lys Leu Ile Lys Met Val
1               5

<210> SEQ ID NO 92
<211> LENGTH: 9
<212> TYPE: PRT
<213> ORGANISM: Artificial Sequence
<220> FEATURE:
<223> OTHER INFORMATION: Synthetic peptide

<400> SEQUENCE: 92

Gln Leu Phe Val Gly Thr Met Thr Leu
1               5

<210> SEQ ID NO 93
<211> LENGTH: 9
<212> TYPE: PRT
<213> ORGANISM: Artificial Sequence
<220> FEATURE:
<223> OTHER INFORMATION: Synthetic peptide

<400> SEQUENCE: 93

Gln Leu Phe Gln Pro Phe Leu Lys Val
1               5

<210> SEQ ID NO 94
<211> LENGTH: 9
<212> TYPE: PRT
<213> ORGANISM: Artificial Sequence
<220> FEATURE:
<223> OTHER INFORMATION: Synthetic peptide

<400> SEQUENCE: 94

Tyr Ala Pro Gly Ala Leu Pro Pro Leu
1               5

<210> SEQ ID NO 95
<211> LENGTH: 9
<212> TYPE: PRT
<213> ORGANISM: Artificial Sequence
<220> FEATURE:
<223> OTHER INFORMATION: Synthetic peptide

<400> SEQUENCE: 95

Val Gln Trp Glu Pro Val Leu Cys Leu
1               5

<210> SEQ ID NO 96
<211> LENGTH: 9
<212> TYPE: PRT
<213> ORGANISM: Artificial Sequence
<220> FEATURE:
<223> OTHER INFORMATION: Synthetic peptide

<400> SEQUENCE: 96

Gly Ile Phe Asn Phe Met Glu Leu Ile
1               5

<210> SEQ ID NO 97
<211> LENGTH: 9
<212> TYPE: PRT
<213> ORGANISM: Artificial Sequence
<220> FEATURE:
<223> OTHER INFORMATION: Synthetic peptide

<400> SEQUENCE: 97

Ala Leu Asp Met Glu Leu Arg Leu Val
1               5

```
<210> SEQ ID NO 98
<211> LENGTH: 9
<212> TYPE: PRT
<213> ORGANISM: Artificial Sequence
<220> FEATURE:
<223> OTHER INFORMATION: Synthetic peptide

<400> SEQUENCE: 98

Cys Leu Val Ser Ala Gly Cys Pro Val
1               5

<210> SEQ ID NO 99
<211> LENGTH: 9
<212> TYPE: PRT
<213> ORGANISM: Artificial Sequence
<220> FEATURE:
<223> OTHER INFORMATION: Synthetic peptide

<400> SEQUENCE: 99

Arg Leu Ile Ile Gly Gln Asn Gly Val
1               5

<210> SEQ ID NO 100
<211> LENGTH: 9
<212> TYPE: PRT
<213> ORGANISM: Artificial Sequence
<220> FEATURE:
<223> OTHER INFORMATION: Synthetic peptide

<400> SEQUENCE: 100

Gly Met Leu Gln Ile Pro Arg Pro Leu
1               5

<210> SEQ ID NO 101
<211> LENGTH: 9
<212> TYPE: PRT
<213> ORGANISM: Artificial Sequence
<220> FEATURE:
<223> OTHER INFORMATION: Synthetic peptide

<400> SEQUENCE: 101

Lys Leu Asp Val Val Ala Ile Glu Ala
1               5

<210> SEQ ID NO 102
<211> LENGTH: 9
<212> TYPE: PRT
<213> ORGANISM: Artificial Sequence
<220> FEATURE:
<223> OTHER INFORMATION: Synthetic peptide

<400> SEQUENCE: 102

Lys Val Tyr Gly Val Glu Ser His Val
1               5

<210> SEQ ID NO 103
<211> LENGTH: 9
<212> TYPE: PRT
<213> ORGANISM: Artificial Sequence
<220> FEATURE:
<223> OTHER INFORMATION: Synthetic peptide

<400> SEQUENCE: 103

Lys Val Tyr Gly Val Glu Ser His Val
1               5

<210> SEQ ID NO 104
```

```
<211> LENGTH: 9
<212> TYPE: PRT
<213> ORGANISM: Artificial Sequence
<220> FEATURE:
<223> OTHER INFORMATION: Synthetic peptide

<400> SEQUENCE: 104

Arg Ile Pro Leu Tyr Tyr Pro Asn Val
1               5

<210> SEQ ID NO 105
<211> LENGTH: 9
<212> TYPE: PRT
<213> ORGANISM: Artificial Sequence
<220> FEATURE:
<223> OTHER INFORMATION: Synthetic peptide

<400> SEQUENCE: 105

Leu Ile Ile Asp Ala Tyr Asn Ser Ile
1               5

<210> SEQ ID NO 106
<211> LENGTH: 9
<212> TYPE: PRT
<213> ORGANISM: Artificial Sequence
<220> FEATURE:
<223> OTHER INFORMATION: Synthetic peptide

<400> SEQUENCE: 106

Met Val Leu Asn Lys Ile Asp Leu Leu
1               5

<210> SEQ ID NO 107
<211> LENGTH: 9
<212> TYPE: PRT
<213> ORGANISM: Artificial Sequence
<220> FEATURE:
<223> OTHER INFORMATION: Synthetic peptide

<400> SEQUENCE: 107

Leu Leu Val Phe Gln Leu Gln Asn Leu
1               5

<210> SEQ ID NO 108
<211> LENGTH: 9
<212> TYPE: PRT
<213> ORGANISM: Artificial Sequence
<220> FEATURE:
<223> OTHER INFORMATION: Synthetic peptide

<400> SEQUENCE: 108

Val Leu Cys Leu Leu Leu Ala Trp Leu
1               5

<210> SEQ ID NO 109
<211> LENGTH: 9
<212> TYPE: PRT
<213> ORGANISM: Artificial Sequence
<220> FEATURE:
<223> OTHER INFORMATION: Synthetic peptide

<400> SEQUENCE: 109

Phe Thr Ser Pro Ala Cys Thr Phe Leu
1               5

<210> SEQ ID NO 110
<211> LENGTH: 9
```

```
<212> TYPE: PRT
<213> ORGANISM: Artificial Sequence
<220> FEATURE:
<223> OTHER INFORMATION: Synthetic peptide

<400> SEQUENCE: 110

Lys Leu Val Met Val Leu Asn Lys Ile
1               5

<210> SEQ ID NO 111
<211> LENGTH: 9
<212> TYPE: PRT
<213> ORGANISM: Artificial Sequence
<220> FEATURE:
<223> OTHER INFORMATION: Synthetic peptide

<400> SEQUENCE: 111

Val Phe Phe Asp Ile Ala Ile Phe Val
1               5

<210> SEQ ID NO 112
<211> LENGTH: 9
<212> TYPE: PRT
<213> ORGANISM: Artificial Sequence
<220> FEATURE:
<223> OTHER INFORMATION: Synthetic peptide

<400> SEQUENCE: 112

Ala Leu Arg Lys Asp Ile Glu Glu Val
1               5

<210> SEQ ID NO 113
<211> LENGTH: 9
<212> TYPE: PRT
<213> ORGANISM: Artificial Sequence
<220> FEATURE:
<223> OTHER INFORMATION: Synthetic peptide

<400> SEQUENCE: 113

Glu Leu Leu Glu Trp Ile His Arg Thr
1               5

<210> SEQ ID NO 114
<211> LENGTH: 9
<212> TYPE: PRT
<213> ORGANISM: Artificial Sequence
<220> FEATURE:
<223> OTHER INFORMATION: Synthetic peptide

<400> SEQUENCE: 114

Ala Ile Asp Thr Leu Phe Ser Cys Val
1               5

<210> SEQ ID NO 115
<211> LENGTH: 9
<212> TYPE: PRT
<213> ORGANISM: Artificial Sequence
<220> FEATURE:
<223> OTHER INFORMATION: Synthetic peptide

<400> SEQUENCE: 115

Lys Leu Asp Ile Thr Pro Lys Ser Val
1               5

<210> SEQ ID NO 116
<211> LENGTH: 9
<212> TYPE: PRT
```

```
<213> ORGANISM: Artificial Sequence
<220> FEATURE:
<223> OTHER INFORMATION: Synthetic peptide

<400> SEQUENCE: 116

Ile Val Asp Ile Phe Leu Ser Phe Leu
1               5

<210> SEQ ID NO 117
<211> LENGTH: 9
<212> TYPE: PRT
<213> ORGANISM: Artificial Sequence
<220> FEATURE:
<223> OTHER INFORMATION: Synthetic peptide

<400> SEQUENCE: 117

Ile Thr Leu Arg Val Leu Leu Ile Val
1               5

<210> SEQ ID NO 118
<211> LENGTH: 9
<212> TYPE: PRT
<213> ORGANISM: Artificial Sequence
<220> FEATURE:
<223> OTHER INFORMATION: Synthetic peptide

<400> SEQUENCE: 118

Lys Leu Ile Lys Met Val Phe Ala Phe
1               5

<210> SEQ ID NO 119
<211> LENGTH: 9
<212> TYPE: PRT
<213> ORGANISM: Artificial Sequence
<220> FEATURE:
<223> OTHER INFORMATION: Synthetic peptide

<400> SEQUENCE: 119

Lys Met Val Phe Ala Phe Cys Ser Met
1               5

<210> SEQ ID NO 120
<211> LENGTH: 9
<212> TYPE: PRT
<213> ORGANISM: Artificial Sequence
<220> FEATURE:
<223> OTHER INFORMATION: Synthetic peptide

<400> SEQUENCE: 120

Ser Leu Cys Gly Arg Ala Leu Val Val
1               5

<210> SEQ ID NO 121
<211> LENGTH: 9
<212> TYPE: PRT
<213> ORGANISM: Artificial Sequence
<220> FEATURE:
<223> OTHER INFORMATION: Synthetic peptide

<400> SEQUENCE: 121

Met Leu Ile Asp Val Leu Leu Ile Gly
1               5

<210> SEQ ID NO 122
<211> LENGTH: 10
<212> TYPE: PRT
<213> ORGANISM: Artificial Sequence
```

<220> FEATURE:
<223> OTHER INFORMATION: Synthetic peptide

<400> SEQUENCE: 122

Met Leu Ile Asp Val Leu Leu Ile Gly Val
1               5                   10

<210> SEQ ID NO 123
<211> LENGTH: 10
<212> TYPE: PRT
<213> ORGANISM: Artificial Sequence
<220> FEATURE:
<223> OTHER INFORMATION: Synthetic peptide

<400> SEQUENCE: 123

Met Met Asp Arg Gln Met Leu Pro Pro Val
1               5                   10

<210> SEQ ID NO 124
<211> LENGTH: 10
<212> TYPE: PRT
<213> ORGANISM: Artificial Sequence
<220> FEATURE:
<223> OTHER INFORMATION: Synthetic peptide

<400> SEQUENCE: 124

Phe Leu Ser Phe Leu Ser Phe Phe Val Val
1               5                   10

<210> SEQ ID NO 125
<211> LENGTH: 10
<212> TYPE: PRT
<213> ORGANISM: Artificial Sequence
<220> FEATURE:
<223> OTHER INFORMATION: Synthetic peptide

<400> SEQUENCE: 125

Ser Leu Ile Glu Thr Leu Leu Asn Tyr Leu
1               5                   10

<210> SEQ ID NO 126
<211> LENGTH: 10
<212> TYPE: PRT
<213> ORGANISM: Artificial Sequence
<220> FEATURE:
<223> OTHER INFORMATION: Synthetic peptide

<400> SEQUENCE: 126

His Met Ala Ala Val Cys Ile Met Glu Val
1               5                   10

<210> SEQ ID NO 127
<211> LENGTH: 10
<212> TYPE: PRT
<213> ORGANISM: Artificial Sequence
<220> FEATURE:
<223> OTHER INFORMATION: Synthetic peptide

<400> SEQUENCE: 127

Thr Leu Leu Asn Tyr Leu Ser Ser Arg Val
1               5                   10

<210> SEQ ID NO 128
<211> LENGTH: 10
<212> TYPE: PRT
<213> ORGANISM: Artificial Sequence
<220> FEATURE:

<223> OTHER INFORMATION: Synthetic peptide

<400> SEQUENCE: 128

His Leu Leu Gly Phe Leu Gln Ile Phe Leu
1               5                   10

<210> SEQ ID NO 129
<211> LENGTH: 10
<212> TYPE: PRT
<213> ORGANISM: Artificial Sequence
<220> FEATURE:
<223> OTHER INFORMATION: Synthetic peptide

<400> SEQUENCE: 129

Leu Leu Ser Ala Ala Thr Phe Phe Gln Leu
1               5                   10

<210> SEQ ID NO 130
<211> LENGTH: 10
<212> TYPE: PRT
<213> ORGANISM: Artificial Sequence
<220> FEATURE:
<223> OTHER INFORMATION: Synthetic peptide

<400> SEQUENCE: 130

Leu Met Ser Leu Gly Lys Val Tyr Gly Val
1               5                   10

<210> SEQ ID NO 131
<211> LENGTH: 10
<212> TYPE: PRT
<213> ORGANISM: Artificial Sequence
<220> FEATURE:
<223> OTHER INFORMATION: Synthetic peptide

<400> SEQUENCE: 131

Met Val Ile Gly Ile Pro Phe Phe Phe Leu
1               5                   10

<210> SEQ ID NO 132
<211> LENGTH: 10
<212> TYPE: PRT
<213> ORGANISM: Artificial Sequence
<220> FEATURE:
<223> OTHER INFORMATION: Synthetic peptide

<400> SEQUENCE: 132

Met Val Ile Gly Ile Pro Phe Phe Phe Leu
1               5                   10

<210> SEQ ID NO 133
<211> LENGTH: 10
<212> TYPE: PRT
<213> ORGANISM: Artificial Sequence
<220> FEATURE:
<223> OTHER INFORMATION: Synthetic peptide

<400> SEQUENCE: 133

Phe Val Ile Cys Trp Thr Pro Ile His Ile
1               5                   10

<210> SEQ ID NO 134
<211> LENGTH: 10
<212> TYPE: PRT
<213> ORGANISM: Artificial Sequence
<220> FEATURE:
<223> OTHER INFORMATION: Synthetic peptide

```
<400> SEQUENCE: 134

Met Leu Asn Asp Ile Val Ala Val Pro Ala
1               5                   10

<210> SEQ ID NO 135
<211> LENGTH: 10
<212> TYPE: PRT
<213> ORGANISM: Artificial Sequence
<220> FEATURE:
<223> OTHER INFORMATION: Synthetic peptide

<400> SEQUENCE: 135

Leu Leu Trp His Gln Val Phe Phe Asp Ile
1               5                   10

<210> SEQ ID NO 136
<211> LENGTH: 10
<212> TYPE: PRT
<213> ORGANISM: Artificial Sequence
<220> FEATURE:
<223> OTHER INFORMATION: Synthetic peptide

<400> SEQUENCE: 136

Trp Met Ala Gly Gly Leu Val Ala His Leu
1               5                   10

<210> SEQ ID NO 137
<211> LENGTH: 10
<212> TYPE: PRT
<213> ORGANISM: Artificial Sequence
<220> FEATURE:
<223> OTHER INFORMATION: Synthetic peptide

<400> SEQUENCE: 137

Glu Leu Pro Asn Gly Cys Val Tyr Tyr Val
1               5                   10

<210> SEQ ID NO 138
<211> LENGTH: 10
<212> TYPE: PRT
<213> ORGANISM: Artificial Sequence
<220> FEATURE:
<223> OTHER INFORMATION: Synthetic peptide

<400> SEQUENCE: 138

His Leu Phe Cys Trp Ile Val Thr Arg Ile
1               5                   10

<210> SEQ ID NO 139
<211> LENGTH: 10
<212> TYPE: PRT
<213> ORGANISM: Artificial Sequence
<220> FEATURE:
<223> OTHER INFORMATION: Synthetic peptide

<400> SEQUENCE: 139

Val Leu Cys Leu Leu Leu Ala Trp Leu Val
1               5                   10

<210> SEQ ID NO 140
<211> LENGTH: 10
<212> TYPE: PRT
<213> ORGANISM: Artificial Sequence
<220> FEATURE:
<223> OTHER INFORMATION: Synthetic peptide
```

```
<400> SEQUENCE: 140

Lys Leu Gln Glu Ser Gly Asp Val Pro Val
1               5                   10

<210> SEQ ID NO 141
<211> LENGTH: 10
<212> TYPE: PRT
<213> ORGANISM: Artificial Sequence
<220> FEATURE:
<223> OTHER INFORMATION: Synthetic peptide

<400> SEQUENCE: 141

Tyr Met Tyr Ile Arg His Gln Gly Glu Val
1               5                   10

<210> SEQ ID NO 142
<211> LENGTH: 10
<212> TYPE: PRT
<213> ORGANISM: Artificial Sequence
<220> FEATURE:
<223> OTHER INFORMATION: Synthetic peptide

<400> SEQUENCE: 142

His Leu Tyr Pro Asn Thr Gln Ala Pro Leu
1               5                   10

<210> SEQ ID NO 143
<211> LENGTH: 10
<212> TYPE: PRT
<213> ORGANISM: Artificial Sequence
<220> FEATURE:
<223> OTHER INFORMATION: Synthetic peptide

<400> SEQUENCE: 143

Tyr Leu Met Arg Arg Arg Arg Ile Glu Ile
1               5                   10

<210> SEQ ID NO 144
<211> LENGTH: 10
<212> TYPE: PRT
<213> ORGANISM: Artificial Sequence
<220> FEATURE:
<223> OTHER INFORMATION: Synthetic peptide

<400> SEQUENCE: 144

Ser Leu Leu Val Phe Gln Leu Gln Asn Leu
1               5                   10

<210> SEQ ID NO 145
<211> LENGTH: 10
<212> TYPE: PRT
<213> ORGANISM: Artificial Sequence
<220> FEATURE:
<223> OTHER INFORMATION: Synthetic peptide

<400> SEQUENCE: 145

Leu Met Gly Ile Phe Asn Phe Met Glu Leu
1               5                   10

<210> SEQ ID NO 146
<211> LENGTH: 10
<212> TYPE: PRT
<213> ORGANISM: Artificial Sequence
<220> FEATURE:
<223> OTHER INFORMATION: Synthetic peptide

<400> SEQUENCE: 146
```

```
Phe Leu Cys Ala Gly Lys Leu Arg Leu Leu
1               5                   10

<210> SEQ ID NO 147
<211> LENGTH: 10
<212> TYPE: PRT
<213> ORGANISM: Artificial Sequence
<220> FEATURE:
<223> OTHER INFORMATION: Synthetic peptide

<400> SEQUENCE: 147

Gly Leu Gly Ile Trp Met Leu Ile Asp Val
1               5                   10

<210> SEQ ID NO 148
<211> LENGTH: 10
<212> TYPE: PRT
<213> ORGANISM: Artificial Sequence
<220> FEATURE:
<223> OTHER INFORMATION: Synthetic peptide

<400> SEQUENCE: 148

Gly Leu Ala Glu Asn Leu Leu Pro Arg Ala
1               5                   10

<210> SEQ ID NO 149
<211> LENGTH: 10
<212> TYPE: PRT
<213> ORGANISM: Artificial Sequence
<220> FEATURE:
<223> OTHER INFORMATION: Synthetic peptide

<400> SEQUENCE: 149

Ile Phe Leu Ser Phe Leu Ser Phe Phe Val
1               5                   10

<210> SEQ ID NO 150
<211> LENGTH: 10
<212> TYPE: PRT
<213> ORGANISM: Artificial Sequence
<220> FEATURE:
<223> OTHER INFORMATION: Synthetic peptide

<400> SEQUENCE: 150

Val Leu Ala Cys Ile Ala Ile Thr Glu Ile
1               5                   10

<210> SEQ ID NO 151
<211> LENGTH: 10
<212> TYPE: PRT
<213> ORGANISM: Artificial Sequence
<220> FEATURE:
<223> OTHER INFORMATION: Synthetic peptide

<400> SEQUENCE: 151

Cys Leu Tyr Ala Asp Leu Asn Arg His Val
1               5                   10

<210> SEQ ID NO 152
<211> LENGTH: 10
<212> TYPE: PRT
<213> ORGANISM: Artificial Sequence
<220> FEATURE:
<223> OTHER INFORMATION: Synthetic peptide

<400> SEQUENCE: 152
```

```
Phe Leu Ser Met Leu Asn Asp Ile Val Ala
1               5                   10
```

<210> SEQ ID NO 153
<211> LENGTH: 10
<212> TYPE: PRT
<213> ORGANISM: Artificial Sequence
<220> FEATURE:
<223> OTHER INFORMATION: Synthetic peptide

<400> SEQUENCE: 153

```
Asn Met Ala Asn Gly Thr Val Ile His Leu
1               5                   10
```

<210> SEQ ID NO 154
<211> LENGTH: 10
<212> TYPE: PRT
<213> ORGANISM: Artificial Sequence
<220> FEATURE:
<223> OTHER INFORMATION: Synthetic peptide

<400> SEQUENCE: 154

```
Gly Leu Ala Val Ser His Met Ala Ala Val
1               5                   10
```

<210> SEQ ID NO 155
<211> LENGTH: 10
<212> TYPE: PRT
<213> ORGANISM: Artificial Sequence
<220> FEATURE:
<223> OTHER INFORMATION: Synthetic peptide

<400> SEQUENCE: 155

```
Lys Leu Leu Gly Leu Val Lys Arg Pro Leu
1               5                   10
```

<210> SEQ ID NO 156
<211> LENGTH: 10
<212> TYPE: PRT
<213> ORGANISM: Artificial Sequence
<220> FEATURE:
<223> OTHER INFORMATION: Synthetic peptide

<400> SEQUENCE: 156

```
Gln Val Phe Phe Asp Ile Ala Ile Phe Val
1               5                   10
```

<210> SEQ ID NO 157
<211> LENGTH: 10
<212> TYPE: PRT
<213> ORGANISM: Artificial Sequence
<220> FEATURE:
<223> OTHER INFORMATION: Synthetic peptide

<400> SEQUENCE: 157

```
Gly Leu Pro Leu Phe Val Gln His Thr Val
1               5                   10
```

<210> SEQ ID NO 158
<211> LENGTH: 10
<212> TYPE: PRT
<213> ORGANISM: Artificial Sequence
<220> FEATURE:
<223> OTHER INFORMATION: Synthetic peptide

<400> SEQUENCE: 158

```
Ala Leu Phe Pro Gly Ile His Leu Glu Thr
```

```
1               5                   10
```

<210> SEQ ID NO 159
<211> LENGTH: 10
<212> TYPE: PRT
<213> ORGANISM: Artificial Sequence
<220> FEATURE:
<223> OTHER INFORMATION: Synthetic peptide

<400> SEQUENCE: 159

```
Ser Met Leu Glu His Ile Ser Lys Asn Leu
1               5                   10
```

<210> SEQ ID NO 160
<211> LENGTH: 10
<212> TYPE: PRT
<213> ORGANISM: Artificial Sequence
<220> FEATURE:
<223> OTHER INFORMATION: Synthetic peptide

<400> SEQUENCE: 160

```
Gln Leu Phe Val Gly Thr Met Thr Leu Leu
1               5                   10
```

<210> SEQ ID NO 161
<211> LENGTH: 10
<212> TYPE: PRT
<213> ORGANISM: Artificial Sequence
<220> FEATURE:
<223> OTHER INFORMATION: Synthetic peptide

<400> SEQUENCE: 161

```
Ser Leu Ile Ala Thr Thr Arg Pro Pro Ala
1               5                   10
```

<210> SEQ ID NO 162
<211> LENGTH: 10
<212> TYPE: PRT
<213> ORGANISM: Artificial Sequence
<220> FEATURE:
<223> OTHER INFORMATION: Synthetic peptide

<400> SEQUENCE: 162

```
Phe Leu Lys Pro Trp Ser His Gly Asn Val
1               5                   10
```

<210> SEQ ID NO 163
<211> LENGTH: 10
<212> TYPE: PRT
<213> ORGANISM: Artificial Sequence
<220> FEATURE:
<223> OTHER INFORMATION: Synthetic peptide

<400> SEQUENCE: 163

```
Ala Leu Gln Gly Leu Pro Leu Asn Cys Val
1               5                   10
```

<210> SEQ ID NO 164
<211> LENGTH: 10
<212> TYPE: PRT
<213> ORGANISM: Artificial Sequence
<220> FEATURE:
<223> OTHER INFORMATION: Synthetic peptide

<400> SEQUENCE: 164

```
His Leu Phe Glu Asp Ser Gln Asn Thr Leu
1               5                   10
```

<210> SEQ ID NO 165
<211> LENGTH: 10
<212> TYPE: PRT
<213> ORGANISM: Artificial Sequence
<220> FEATURE:
<223> OTHER INFORMATION: Synthetic peptide

<400> SEQUENCE: 165

Tyr Leu Ser Thr Asp Val Gly Phe Cys Thr
1               5                   10

<210> SEQ ID NO 166
<211> LENGTH: 10
<212> TYPE: PRT
<213> ORGANISM: Artificial Sequence
<220> FEATURE:
<223> OTHER INFORMATION: Synthetic peptide

<400> SEQUENCE: 166

Tyr Leu Ser Thr Asp Val Gly Phe Cys Thr
1               5                   10

<210> SEQ ID NO 167
<211> LENGTH: 10
<212> TYPE: PRT
<213> ORGANISM: Artificial Sequence
<220> FEATURE:
<223> OTHER INFORMATION: Synthetic peptide

<400> SEQUENCE: 167

Phe Leu Val Thr Glu Glu Arg Ile Gln Leu
1               5                   10

<210> SEQ ID NO 168
<211> LENGTH: 10
<212> TYPE: PRT
<213> ORGANISM: Artificial Sequence
<220> FEATURE:
<223> OTHER INFORMATION: Synthetic peptide

<400> SEQUENCE: 168

Gly Met Thr Phe Phe Glu Val Ser Pro Leu
1               5                   10

<210> SEQ ID NO 169
<211> LENGTH: 10
<212> TYPE: PRT
<213> ORGANISM: Artificial Sequence
<220> FEATURE:
<223> OTHER INFORMATION: Synthetic peptide

<400> SEQUENCE: 169

Ser Leu Ala Leu Phe Pro Gly Ile His Leu
1               5                   10

<210> SEQ ID NO 170
<211> LENGTH: 10
<212> TYPE: PRT
<213> ORGANISM: Artificial Sequence
<220> FEATURE:
<223> OTHER INFORMATION: Synthetic peptide

<400> SEQUENCE: 170

Tyr Val Ala Gln Leu Ala Ser Met Gln Val
1               5                   10

```
<210> SEQ ID NO 171
<211> LENGTH: 10
<212> TYPE: PRT
<213> ORGANISM: Artificial Sequence
<220> FEATURE:
<223> OTHER INFORMATION: Synthetic peptide

<400> SEQUENCE: 171

Tyr Val Ala Gln Leu Ala Ser Met Gln Val
1               5                   10

<210> SEQ ID NO 172
<211> LENGTH: 10
<212> TYPE: PRT
<213> ORGANISM: Artificial Sequence
<220> FEATURE:
<223> OTHER INFORMATION: Synthetic peptide

<400> SEQUENCE: 172

Ala Ile Tyr Glu His Leu Phe Cys Trp Ile
1               5                   10

<210> SEQ ID NO 173
<211> LENGTH: 10
<212> TYPE: PRT
<213> ORGANISM: Artificial Sequence
<220> FEATURE:
<223> OTHER INFORMATION: Synthetic peptide

<400> SEQUENCE: 173

Leu Met Trp Val Cys Ala Leu Gly His Leu
1               5                   10

<210> SEQ ID NO 174
<211> LENGTH: 10
<212> TYPE: PRT
<213> ORGANISM: Artificial Sequence
<220> FEATURE:
<223> OTHER INFORMATION: Synthetic peptide

<400> SEQUENCE: 174

Gly Ile Val Asp Ile Phe Leu Ser Phe Leu
1               5                   10

<210> SEQ ID NO 175
<211> LENGTH: 10
<212> TYPE: PRT
<213> ORGANISM: Artificial Sequence
<220> FEATURE:
<223> OTHER INFORMATION: Synthetic peptide

<400> SEQUENCE: 175

Lys Met Val Phe Ala Phe Cys Ser Met Leu
1               5                   10

<210> SEQ ID NO 176
<211> LENGTH: 10
<212> TYPE: PRT
<213> ORGANISM: Artificial Sequence
<220> FEATURE:
<223> OTHER INFORMATION: Synthetic peptide

<400> SEQUENCE: 176

Tyr Leu Glu His Arg Leu Phe Ser Arg Leu
1               5                   10
```

<210> SEQ ID NO 177
<211> LENGTH: 10
<212> TYPE: PRT
<213> ORGANISM: Artificial Sequence
<220> FEATURE:
<223> OTHER INFORMATION: Synthetic peptide

<400> SEQUENCE: 177

Tyr Leu Gly Pro Thr Asp Trp Gln Leu Ala
1               5                   10

<210> SEQ ID NO 178
<211> LENGTH: 10
<212> TYPE: PRT
<213> ORGANISM: Artificial Sequence
<220> FEATURE:
<223> OTHER INFORMATION: Synthetic peptide

<400> SEQUENCE: 178

Gly Met Asn Trp Arg Pro Ile Leu Thr Ile
1               5                   10

<210> SEQ ID NO 179
<211> LENGTH: 10
<212> TYPE: PRT
<213> ORGANISM: Artificial Sequence
<220> FEATURE:
<223> OTHER INFORMATION: Synthetic peptide

<400> SEQUENCE: 179

Phe Thr Ser Pro Ala Cys Thr Phe Leu Ala
1               5                   10

<210> SEQ ID NO 180
<211> LENGTH: 10
<212> TYPE: PRT
<213> ORGANISM: Artificial Sequence
<220> FEATURE:
<223> OTHER INFORMATION: Synthetic peptide

<400> SEQUENCE: 180

Tyr Leu Pro Glu Asp Phe Ile Trp Val Gly
1               5                   10

<210> SEQ ID NO 181
<211> LENGTH: 10
<212> TYPE: PRT
<213> ORGANISM: Artificial Sequence
<220> FEATURE:
<223> OTHER INFORMATION: Synthetic peptide

<400> SEQUENCE: 181

Glu Leu Met Gln Ala Leu Trp Cys Thr Leu
1               5                   10

<210> SEQ ID NO 182
<211> LENGTH: 10
<212> TYPE: PRT
<213> ORGANISM: Artificial Sequence
<220> FEATURE:
<223> OTHER INFORMATION: Synthetic peptide

<400> SEQUENCE: 182

Leu Met Val His Val Glu Ala Gln Tyr Ile
1               5                   10

<210> SEQ ID NO 183

<211> LENGTH: 10
<212> TYPE: PRT
<213> ORGANISM: Artificial Sequence
<220> FEATURE:
<223> OTHER INFORMATION: Synthetic peptide

<400> SEQUENCE: 183

Gly Leu Glu Lys Gly His Leu Glu Pro Val
1               5                   10

<210> SEQ ID NO 184
<211> LENGTH: 10
<212> TYPE: PRT
<213> ORGANISM: Artificial Sequence
<220> FEATURE:
<223> OTHER INFORMATION: Synthetic peptide

<400> SEQUENCE: 184

Val Gln Trp Glu Pro Val Leu Cys Leu Leu
1               5                   10

<210> SEQ ID NO 185
<211> LENGTH: 10
<212> TYPE: PRT
<213> ORGANISM: Artificial Sequence
<220> FEATURE:
<223> OTHER INFORMATION: Synthetic peptide

<400> SEQUENCE: 185

Tyr Phe Leu Ser Leu Leu Val Phe Gln Leu
1               5                   10

<210> SEQ ID NO 186
<211> LENGTH: 10
<212> TYPE: PRT
<213> ORGANISM: Artificial Sequence
<220> FEATURE:
<223> OTHER INFORMATION: Synthetic peptide

<400> SEQUENCE: 186

Gly Met Leu Gln Ile Pro Arg Pro Leu Ile
1               5                   10

<210> SEQ ID NO 187
<211> LENGTH: 10
<212> TYPE: PRT
<213> ORGANISM: Artificial Sequence
<220> FEATURE:
<223> OTHER INFORMATION: Synthetic peptide

<400> SEQUENCE: 187

Gly Leu Leu Asp Pro Ala Glu Gly Leu Leu
1               5                   10

<210> SEQ ID NO 188
<211> LENGTH: 10
<212> TYPE: PRT
<213> ORGANISM: Artificial Sequence
<220> FEATURE:
<223> OTHER INFORMATION: Synthetic peptide

<400> SEQUENCE: 188

Ala Leu Trp Cys Thr Leu Arg Asn Pro Ala
1               5                   10

<210> SEQ ID NO 189
<211> LENGTH: 10

```
<212> TYPE: PRT
<213> ORGANISM: Artificial Sequence
<220> FEATURE:
<223> OTHER INFORMATION: Synthetic peptide

<400> SEQUENCE: 189

Leu Leu Pro Asn Glu Arg Thr Ile Ser Leu
1               5                   10

<210> SEQ ID NO 190
<211> LENGTH: 10
<212> TYPE: PRT
<213> ORGANISM: Artificial Sequence
<220> FEATURE:
<223> OTHER INFORMATION: Synthetic peptide

<400> SEQUENCE: 190

Leu Gln Leu Phe Gln Pro Phe Leu Lys Val
1               5                   10

<210> SEQ ID NO 191
<211> LENGTH: 10
<212> TYPE: PRT
<213> ORGANISM: Artificial Sequence
<220> FEATURE:
<223> OTHER INFORMATION: Synthetic peptide

<400> SEQUENCE: 191

Thr Ile Ser Glu Trp Trp Gln Gln Glu Val
1               5                   10

<210> SEQ ID NO 192
<211> LENGTH: 10
<212> TYPE: PRT
<213> ORGANISM: Artificial Sequence
<220> FEATURE:
<223> OTHER INFORMATION: Synthetic peptide

<400> SEQUENCE: 192

Phe Val Val Gly Val Val Glu Gln Val Val
1               5                   10

<210> SEQ ID NO 193
<211> LENGTH: 10
<212> TYPE: PRT
<213> ORGANISM: Artificial Sequence
<220> FEATURE:
<223> OTHER INFORMATION: Synthetic peptide

<400> SEQUENCE: 193

Tyr Met Leu His Leu Glu Ser Trp Leu Gln
1               5                   10

<210> SEQ ID NO 194
<211> LENGTH: 10
<212> TYPE: PRT
<213> ORGANISM: Artificial Sequence
<220> FEATURE:
<223> OTHER INFORMATION: Synthetic peptide

<400> SEQUENCE: 194

Gln Leu Asp Asp Leu Gln Thr Thr Phe Ala
1               5                   10

<210> SEQ ID NO 195
<211> LENGTH: 10
<212> TYPE: PRT
```

<213> ORGANISM: Artificial Sequence
<220> FEATURE:
<223> OTHER INFORMATION: Synthetic peptide

<400> SEQUENCE: 195

Lys Leu Val Val Val Gly Ala Ser Gly Val
1               5                   10

<210> SEQ ID NO 196
<211> LENGTH: 10
<212> TYPE: PRT
<213> ORGANISM: Artificial Sequence
<220> FEATURE:
<223> OTHER INFORMATION: Synthetic peptide

<400> SEQUENCE: 196

Ala Leu Pro Pro Leu Pro Pro Pro His Leu
1               5                   10

<210> SEQ ID NO 197
<211> LENGTH: 10
<212> TYPE: PRT
<213> ORGANISM: Artificial Sequence
<220> FEATURE:
<223> OTHER INFORMATION: Synthetic peptide

<400> SEQUENCE: 197

Gln Met Ser Pro Trp Gly Met Leu Gln Ile
1               5                   10

<210> SEQ ID NO 198
<211> LENGTH: 10
<212> TYPE: PRT
<213> ORGANISM: Artificial Sequence
<220> FEATURE:
<223> OTHER INFORMATION: Synthetic peptide

<400> SEQUENCE: 198

Leu Leu Met Val Ile Gly Ile Pro Phe Phe
1               5                   10

<210> SEQ ID NO 199
<211> LENGTH: 10
<212> TYPE: PRT
<213> ORGANISM: Artificial Sequence
<220> FEATURE:
<223> OTHER INFORMATION: Synthetic peptide

<400> SEQUENCE: 199

Ser Leu Met Gly Thr Asp Ser His Thr Thr
1               5                   10

<210> SEQ ID NO 200
<211> LENGTH: 10
<212> TYPE: PRT
<213> ORGANISM: Artificial Sequence
<220> FEATURE:
<223> OTHER INFORMATION: Synthetic peptide

<400> SEQUENCE: 200

Gly Met Thr Lys Glu Gln Leu Leu Glu Leu
1               5                   10

<210> SEQ ID NO 201
<211> LENGTH: 10
<212> TYPE: PRT
<213> ORGANISM: Artificial Sequence

```
<220> FEATURE:
<223> OTHER INFORMATION: Synthetic peptide

<400> SEQUENCE: 201

Ser Leu Cys Gly Arg Ala Leu Val Val Leu
1               5                   10

<210> SEQ ID NO 202
<211> LENGTH: 10
<212> TYPE: PRT
<213> ORGANISM: Artificial Sequence
<220> FEATURE:
<223> OTHER INFORMATION: Synthetic peptide

<400> SEQUENCE: 202

Phe Gln Leu Gln Asn Leu Pro Cys Gly Met
1               5                   10

<210> SEQ ID NO 203
<211> LENGTH: 10
<212> TYPE: PRT
<213> ORGANISM: Artificial Sequence
<220> FEATURE:
<223> OTHER INFORMATION: Synthetic peptide

<400> SEQUENCE: 203

Gly Ile Trp Met Leu Ile Asp Val Leu Leu
1               5                   10

<210> SEQ ID NO 204
<211> LENGTH: 10
<212> TYPE: PRT
<213> ORGANISM: Artificial Sequence
<220> FEATURE:
<223> OTHER INFORMATION: Synthetic peptide

<400> SEQUENCE: 204

Thr Met Ala Gly Lys Leu Thr Ala Ser Ala
1               5                   10

<210> SEQ ID NO 205
<211> LENGTH: 10
<212> TYPE: PRT
<213> ORGANISM: Artificial Sequence
<220> FEATURE:
<223> OTHER INFORMATION: Synthetic peptide

<400> SEQUENCE: 205

Ala Leu Met Val Gly Val Gly Thr Val Met
1               5                   10

<210> SEQ ID NO 206
<211> LENGTH: 10
<212> TYPE: PRT
<213> ORGANISM: Artificial Sequence
<220> FEATURE:
<223> OTHER INFORMATION: Synthetic peptide

<400> SEQUENCE: 206

Val Leu Val Val Val Ala Val Phe Val Ile
1               5                   10

<210> SEQ ID NO 207
<211> LENGTH: 10
<212> TYPE: PRT
<213> ORGANISM: Artificial Sequence
<220> FEATURE:
```

```
<223> OTHER INFORMATION: Synthetic peptide

<400> SEQUENCE: 207

Gln Leu Tyr Val Ala Gln Leu Ala Ser Met
1               5                   10

<210> SEQ ID NO 208
<211> LENGTH: 10
<212> TYPE: PRT
<213> ORGANISM: Artificial Sequence
<220> FEATURE:
<223> OTHER INFORMATION: Synthetic peptide

<400> SEQUENCE: 208

Gln Leu Tyr Val Ala Gln Leu Ala Ser Met
1               5                   10

<210> SEQ ID NO 209
<211> LENGTH: 10
<212> TYPE: PRT
<213> ORGANISM: Artificial Sequence
<220> FEATURE:
<223> OTHER INFORMATION: Synthetic peptide

<400> SEQUENCE: 209

Val Met Leu Cys Thr Gly Leu Gly Val Ile
1               5                   10

<210> SEQ ID NO 210
<211> LENGTH: 10
<212> TYPE: PRT
<213> ORGANISM: Artificial Sequence
<220> FEATURE:
<223> OTHER INFORMATION: Synthetic peptide

<400> SEQUENCE: 210

His Leu Leu Asn His Val Pro His Gln Met
1               5                   10

<210> SEQ ID NO 211
<211> LENGTH: 10
<212> TYPE: PRT
<213> ORGANISM: Artificial Sequence
<220> FEATURE:
<223> OTHER INFORMATION: Synthetic peptide

<400> SEQUENCE: 211

Met Thr Leu Leu Ser Gly Val Leu Thr Leu
1               5                   10

<210> SEQ ID NO 212
<211> LENGTH: 10
<212> TYPE: PRT
<213> ORGANISM: Artificial Sequence
<220> FEATURE:
<223> OTHER INFORMATION: Synthetic peptide

<400> SEQUENCE: 212

Leu Met Val Ile Gly Ile Pro Phe Phe Phe
1               5                   10

<210> SEQ ID NO 213
<211> LENGTH: 10
<212> TYPE: PRT
<213> ORGANISM: Artificial Sequence
<220> FEATURE:
<223> OTHER INFORMATION: Synthetic peptide
```

```
<400> SEQUENCE: 213

Ala Val Phe Val Ile Cys Trp Thr Pro Ile
1               5                   10

<210> SEQ ID NO 214
<211> LENGTH: 10
<212> TYPE: PRT
<213> ORGANISM: Artificial Sequence
<220> FEATURE:
<223> OTHER INFORMATION: Synthetic peptide

<400> SEQUENCE: 214

Thr Leu Arg Val Leu Leu Ile Val Gly Val
1               5                   10

<210> SEQ ID NO 215
<211> LENGTH: 10
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(10)
<223> OTHER INFORMATION: Control

<400> SEQUENCE: 215

Lys Thr Ser Leu Tyr Asn Leu Arg Arg Gly
1               5                   10
```